(12) United States Patent
Konofagou et al.

(10) Patent No.: US 11,273,329 B2
(45) Date of Patent: *Mar. 15, 2022

(54) SYSTEMS AND METHODS FOR OPENING OF A TISSUE BARRIER IN PRIMATES

(71) Applicant: THE TRUSTEES OF COLUMBIA UNIVERSITY IN THE CITY OF NEW YORK, New York, NY (US)

(72) Inventors: Elisa E. Konofagou, New York, NY (US); Fabrice Marquet, New York, NY (US); Yao-Sheng Tung, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 321 days.

This patent is subject to a terminal disclaimer.

(21) Appl. No.: 16/575,044

(22) Filed: Sep. 18, 2019

(65) Prior Publication Data

US 2020/0086146 A1   Mar. 19, 2020

Related U.S. Application Data

(63) Continuation of application No. 14/091,010, filed on Nov. 26, 2013, now Pat. No. 10,441,820, which is a
(Continued)

(51) Int. Cl.
*A61N 7/00* (2006.01)
*A61B 17/225* (2006.01)
(Continued)

(52) U.S. Cl.
CPC .............. *A61N 7/00* (2013.01); *A61B 8/0808* (2013.01); *A61B 8/481* (2013.01);
(Continued)

(58) Field of Classification Search
CPC .............. A61N 7/00; A61N 2007/0039; A61B 17/2258; A61B 8/481; A61B 8/0808;
(Continued)

(56) References Cited

U.S. PATENT DOCUMENTS 3,598,111 A   8/1971   Kahn
4,463,608 A   8/1984   Takeuchi et al.
(Continued)

FOREIGN PATENT DOCUMENTS

EP   0 221 409 A2   5/1987
EP   0 627 206 A2   12/1994
(Continued)

OTHER PUBLICATIONS

U.S. Appl. No. 11/433,510 (U.S. Pat. No. 2007/0049824), filed May 12, 2006 (Mar. 1, 2007).
(Continued)

*Primary Examiner* — Hien N Nguyen
(74) *Attorney, Agent, or Firm* — Baker Botts L.L.P.

(57) ABSTRACT

Systems and methods for cavitation-guided opening of a targeted region of tissue within a primate skull are provided. In one example, a method includes delivering one or more microbubbles to proximate the targeted region, applying an ultrasound beam, using a transducer, through the skull of the primate to the targeted region to open the tissue, transcranially acquiring acoustic emissions produced from an interaction between the one or more microbubbles and the tissue, and determining a cavitation spectrum from the acquired acoustic emissions.

10 Claims, 30 Drawing Sheets

Related U.S. Application Data continuation-in-part of application No. PCT/US2012/039708, filed on May 25, 2012.

(60) Provisional application No. 61/490,440, filed on May 26, 2011.

(51) Int. Cl.
| | |
|---|---|
| *A61B 8/08* | (2006.01) |
| *A61B 17/00* | (2006.01) |
| *A61B 17/22* | (2006.01) |
| *A61B 90/10* | (2016.01) |
| *A61B 90/00* | (2016.01) |

(52) U.S. Cl.
CPC .......... *A61B 17/2258* (2013.01); *A61B 90/10* (2016.02); *A61B 2017/00106* (2013.01); *A61B 2017/22008* (2013.01); *A61B 2017/22089* (2013.01); *A61B 2090/378* (2016.02); *A61B 2503/40* (2013.01); *A61N 2007/0039* (2013.01)

(58) Field of Classification Search
CPC ........... A61B 2017/00106; A61B 2017/22008; A61B 2017/22089; A61B 2503/40; A61B 90/10; A61B 2090/378
See application file for complete search history.

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,882,679 A | 11/1989 | Tuy et al. |
| 4,926,675 A | 5/1990 | Schohl et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Iinuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,718,241 A | 2/1998 | Ben-haim et al. |
| 5,722,411 A | 3/1998 | Suzuki et al. |
| 5,741,522 A | 4/1998 | Violante et al. |
| 5,752,515 A | 5/1998 | Jolesz et al. |
| 5,769,790 A | 6/1998 | Watkins et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plews |
| 6,259,943 B1 | 7/2001 | Cosman et al. |
| 6,270,459 B1 | 8/2001 | Konofagou et al. |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,865 B1 | 7/2002 | Salcudean et al. |
| 6,425,867 B1 | 7/2002 | Vaezy et al. |
| 6,447,450 B1 | 9/2002 | Oldstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,514,221 B2 | 2/2003 | Hynynen et al. |
| 6,529,770 B1 | 3/2003 | Grimblatov |
| 6,537,217 B1 | 3/2003 | Bjærum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu |
| 6,770,033 B1 | 8/2004 | Fink et al. |
| 6,775,400 B1 | 8/2004 | Zhao et al. |
| 6,875,176 B2 | 4/2005 | Mourad et al. |
| 6,936,151 B1 | 8/2005 | Lock et al. |
| 6,994,673 B2 | 2/2006 | Lysansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson et al. |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,208,709 B2 | 6/2012 | Ding et al. |
| 8,257,338 B2 | 9/2012 | Keenan et al. |
| 9,063,220 B2 | 6/2015 | Yoda et al. |
| 9,358,023 B2 | 6/2016 | Konofagou et al. |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0169484 A1 | 11/2002 | Mathis et al. |
| 2002/0193784 A1 | 12/2002 | McHale et al. |
| 2003/0040675 A1 | 2/2003 | Sharrock |
| 2003/0097068 A1 | 5/2003 | Hossack et al. |
| 2003/0125621 A1 | 7/2003 | Drukker et al. |
| 2003/0135124 A1 | 7/2003 | Russell |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2003/0236466 A1 | 12/2003 | Tarjan et al. |
| 2004/0006266 A1 | 1/2004 | Ustuner et al. |
| 2004/0049134 A1 | 3/2004 | Tosaya et al. |
| 2004/0049232 A1 | 3/2004 | Ideker et al. |
| 2004/0054357 A1 | 3/2004 | O'Donnell |
| 2004/0059220 A1 | 3/2004 | Mourad et al. |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0116812 A1 | 6/2004 | Selzer et al. |
| 2004/0122320 A1 | 6/2004 | Murashita |
| 2004/0143189 A1 | 7/2004 | Lysyansky et al. |
| 2004/0167403 A1 | 8/2004 | Nightingale et al. |
| 2004/0172081 A1 | 9/2004 | Wang |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0249580 A1 | 12/2004 | Pourcelot et al. |
| 2004/0258760 A1 | 12/2004 | Wheatley et al. |
| 2005/0004466 A1 | 1/2005 | Hynenen et al. |
| 2005/0026262 A1 | 2/2005 | Yoshitani et al. |
| 2005/0054930 A1 | 3/2005 | Rickets et al. |
| 2005/0059876 A1 | 3/2005 | Krishnan |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1 | 6/2005 | Weitzel et al. |
| 2005/0175541 A1 | 8/2005 | Lanza et al. |
| 2005/0201942 A1 | 9/2005 | Dugstad et al. |

(56) References Cited

U.S. PATENT DOCUMENTS

| | | |
|---|---|---|
| 2005/0203395 A1 | 9/2005 | Sui et al. |
| 2005/0233399 A1 | 9/2005 | Vaezy et al. |
| 2005/0259864 A1 | 11/2005 | Dickinson et al. |
| 2005/0267695 A1 | 12/2005 | German |
| 2005/0277824 A1 | 12/2005 | Aubry et al. |
| 2005/0277835 A1 | 12/2005 | Angel et al. |
| 2006/0034904 A1 | 2/2006 | Weimann |
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241462 A1* | 10/2006 | Chou ................. A61B 8/0808 600/455 |
| 2006/0241529 A1* | 10/2006 | Hynynen ............ A61B 8/0816 601/2 |
| 2007/0049824 A1 | 3/2007 | Konofagou et al. |
| 2007/0055179 A1 | 3/2007 | Deem et al. |
| 2007/0059247 A1 | 3/2007 | Lindner et al. |
| 2007/0071683 A1 | 3/2007 | Dayton et al. |
| 2007/0129652 A1 | 6/2007 | Nita |
| 2007/0207194 A1 | 9/2007 | Grayburn et al. |
| 2007/0219447 A1 | 9/2007 | Kanai et al. |
| 2007/0232962 A1 | 10/2007 | Zumeris et al. |
| 2007/0239001 A1 | 10/2007 | Mehi et al. |
| 2007/0276242 A1 | 11/2007 | Konofagou et al. |
| 2007/0276245 A1 | 11/2007 | Konofagou et al. |
| 2007/0276254 A1 | 11/2007 | Konofagou |
| 2008/0089848 A1 | 4/2008 | DiMauro |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0143241 A1 | 6/2010 | Johnson et al. |
| 2010/0286527 A1 | 11/2010 | Cannon et al. |
| 2011/0028854 A1 | 2/2011 | Addison et al. |
| 2011/0098562 A1 | 4/2011 | Salgo et al. |
| 2011/0177005 A1 | 7/2011 | Rapoport et al. |
| 2011/0208038 A1 | 8/2011 | Konofagou et al. |
| 2011/0295105 A1 | 12/2011 | Konofagou et al. |
| 2011/0313328 A1 | 12/2011 | Nita |
| 2012/0004693 A1 | 1/2012 | Lo et al. |
| 2012/0179073 A1 | 7/2012 | Nita |
| 2013/0038479 A1 | 2/2013 | Eldar et al. |
| 2013/0046229 A1 | 2/2013 | Konofagou et al. |
| 2013/0066211 A1 | 3/2013 | Konofagou et al. |
| 2013/0131495 A1 | 5/2013 | Konofagou et al. |
| 2013/0195313 A1 | 8/2013 | Gauthier et al. |
| 2013/0204166 A1 | 8/2013 | Villanueva et al. |
| 2013/0289398 A1 | 10/2013 | Borden et al. |
| 2013/0304407 A1 | 11/2013 | George et al. |
| 2013/0315491 A1 | 11/2013 | Konofagou et al. |
| 2014/0114216 A1 | 4/2014 | Konofagou et al. |
| 2016/0107002 A1 | 4/2016 | Nita |

FOREIGN PATENT DOCUMENTS

| | | |
|---|---|---|
| WO | WO 1999/037938 A1 | 7/1999 |
| WO | WO 2005/030171 A1 | 4/2005 |
| WO | WO 2007/0148279 A1 | 12/2007 |
| WO | WO 2008/015012 A1 | 2/2008 |
| WO | WO 2008/027520 A2 | 3/2008 |
| WO | WO 2008/062342 A2 | 5/2008 |
| WO | WO 2008/131217 A1 | 10/2008 |
| WO | WO 2008/131302 A2 | 10/2008 |
| WO | WO 2008/157422 A1 | 12/2008 |
| WO | WO 2010/030819 A1 | 3/2010 |
| WO | WO 2010/044385 A1 | 4/2010 |
| WO | WO 2010/063951 A1 | 6/2010 |
| WO | WO 2011/028690 A1 | 3/2011 |
| WO | WO 2011/035312 A1 | 3/2011 |

OTHER PUBLICATIONS

U.S. Appl. No. 11/697,573 (Abandoned), filed Apr. 6, 2007.
U.S. Appl. No. 11/697,579 (Abandoned), filed Apr. 6, 2007.
U.S. Appl. No. 11/899,004 (U.S. Pat. No. 8,150,128), filed Aug. 30, 2007 (Apr. 3, 2012).
U.S. Appl. No. 12/077,612 (U.S. Pat. No. 2009/0005711), filed Mar. 19, 2008 (Jan. 1, 2009).
U.S. Appl. No. 12/096,254 (U.S. Pat. No. 2009/0221916), filed Nov. 26, 2008 (Sep. 3, 2009).
U.S. Appl. No. 13/019,029 (U.S. Pat. No. 8,428,687), filed Feb. 1, 2011 (Apr. 23, 2013).
U.S. Appl. No. 13/045,070 (U.S. Pat. No. 9,302,124), filed Mar. 10, 2011 (Apr. 5, 2016).
U.S. Appl. No. 13/353,148 (U.S. Pat. No. 2013/0066211), filed Jan. 18, 2012 (Mar. 14, 2013).
U.S. Appl. No. 13/426,400 (U.S. Pat. No. 9,358,023), filed Mar. 21, 2012 (Jun. 7, 2016).
U.S. Appl. No. 13/529,239 (U.S. Pat. No. 2013/0131495), filed Jun. 21, 2012 (May 23, 2013).
U.S. Appl. No. 13/848,436 (U.S. Pat. No. 9,514,358), filed Mar. 21, 2013 (Dec. 6, 2016).
U.S. Appl. No. 14/091,010 (U.S. Pat. No. 10,441,820), filed Nov. 26, 2013 (Oct. 15, 2019).
U.S. Appl. No. 14/300,106 (U.S. Pat. No. 9,247,921), filed Jun. 9, 2014 (Feb. 2, 2016).
U.S. Appl. No. 14/449,820 (U.S. Pat. No. 2014/0343424), filed Aug. 1, 2014 (Nov. 20, 2014).
U.S. Appl. No. 14/457,023 (U.S. Pat. No. 10,322,178), filed Aug. 11, 2014 (Jun. 18, 2019).
U.S. Appl. No. 14/476,543 (U.S. Pat. No. 10,028,723), filed Sep. 3, 2014 (Jul. 24, 2018).
U.S. Appl. No. 14/682,980 (U.S. Pat. No. 10,517,564), filed Apr. 9, 2015 (Dec. 31, 2019).
U.S. Appl. No. 14/695,674 (U.S. Pat. No. 2015/0297188), filed Apr. 24, 2015 (Oct. 22, 2015).
U.S. Appl. No. 14/695,674 (U.S. Pat. No. 2016/0074678), filed Nov. 23, 2015 (Mar. 17, 2016).
U.S. Appl. No. 15/048,761 (U.S. Pat. No. 2016/0249880), filed Feb. 19, 2016 (Sep. 1, 2016).
U.S. Appl. No. 15/165,942 (U.S. Pat. No. 10,166,379), filed May 26, 2016 (Jan. 1, 2019).
U.S. Appl. No. 15/368,366 (U.S. Pat. No. 2017/0148163), filed Dec. 2, 2016 (May 25, 2017).
U.S. Appl. No. 11/433,510, filed Apr. 7, 2014 Applicant Initiated Interview Summary.
U.S. Appl. No. 11/433,510, filed Apr. 4, 2014 Response to Non-Final Office Action.
U.S. Appl. No. 11/433,510, filed Jul. 23, 2014 Issue Fee Payment.
U.S. Appl. No. 11/433,510, filed Apr. 23, 2014 Notice of Allowance.
U.S. Appl. No. 11/433,510, filed Oct. 4, 2013 Non-Final Office Action.
U.S. Appl. No. 11/433,510, filed Mar. 30, 2012 Request for Continued Examination (RCE).
U.S. Appl. No. 11/433,510, filed Mar. 28, 2012 Advisory Action
U.S. Appl. No. 11/433,510, filed Dec. 29, 2011 Response to Final Office Action.
U.S. Appl. No. 11/433,510, filed Sep. 30, 2011 Final Office Action.
U.S. Appl. No. 11/433,510, filed May 23, 2011 Response to Non-Final Office Action.
U.S. Appl. No. 11/433,510, filed Jan. 21, 2011 Non-Final Office Action.

(56) References Cited

OTHER PUBLICATIONS

U.S. Appl. No. 11/433,510, filed Oct. 28, 2010 Response to Non-Final Office Action.
U.S. Appl. No. 11/433,510, filed Apr. 28, 2010 Non-Final Office Action.
U.S. Appl. No. 11/433,510, filed Apr. 13, 2010 Amendment and Request for Contiuned Examination (RCE).
U.S. Appl. No. 11/433,510, filed Nov. 12, 2009 Final Office Action.
U.S. Appl. No. 11/433,510, filed Aug. 6, 2009 Response to Non-Final Office Action.
U.S. Appl. No. 11/433,510, filed Mar. 17, 2009 Non-Final Office Action.
U.S. Appl. No. 11/697,573, filed Jan. 12, 2015 Notice of Abandonment.
U.S. Appl. No. 11/697,573, filed Jun. 16, 2014 Non-Final Office Action.
U.S. Appl. No. 11/697,573, filed Oct. 17, 2013 Final Office Action.
U.S. Appl. No. 11/697,573, filed Sep. 4, 2013 Response to Non-Final Office Action.
U.S. Appl. No. 11/697,573, filed May 10, 2013 Non-Final Office Action.
U.S. Appl. No. 11/697,573, filed Jan. 18, 2013 Amendment and Request for Continued Examination (RCE).
U.S. Appl. No. 11/697,573, filed Jul. 18, 2012 Final Office Action.
U.S. Appl. No. 11/697,573, filed Jun. 27, 2012 Response to Non-Final Office Action.
U.S. Appl. No. 11/697,573, filed Jan. 26, 2012 Non-Final Office Action.
U.S. Appl. No. 11/697,573, filed Aug. 18, 2011 Amendment and Request for Contiuned Examination (RCE).
U.S. Appl. No. 11/697,573, filed Mar. 18, 2011 Final Office Action.
U.S. Appl. No. 11/697,573, filed Dec. 22, 2010 Response to Non-Final Office Action.
U.S. Appl. No. 11/697,573, filed Jun. 23, 2010 Non-Final Office Action.
U.S. Appl. No. 11/697,579, filed Nov. 28, 2011 Notice of Abandonment.
U.S. Appl. No. 11/697,579, filed Apr. 29, 2011 Final Office Action.
U.S. Appl. No. 11/697,579, filed Feb. 7, 2011 Response to Non-Final Office Action.
U.S. Appl. No. 11/697,579, filed Aug. 6, 2010 Non-Final Office Action.
U.S. Appl. No. 11/697,579, filed May 17, 2010 Response to Non-Final Office Action.
U.S. Appl. No. 11/697,579, filed Nov. 17, 2009 Non-Final Office Action.
U.S. Appl. No. 11/697,579, filed Oct. 15, 2009 Amendment and Request for Continued Examination (RCE).
U.S. Appl. No. 11/697,579, filed Jul. 15, 2009 Response to Final Office Action.
U.S. Appl. No. 11/697,579, filed Apr. 15, 2009 Final Office Action.
U.S. Appl. No. 11/697,579, filed Jan. 16, 2009 Response to Non-Final Office Action.
U.S. Appl. No. 11/697,579, filed Jul. 18, 2008 Non-Final Office Action.
U.S. Appl. No. 11/899,004, filed Nov. 3, 2011 Decision on Petition.
U.S. Appl. No. 11/899,004, filed Oct. 4, 2011 Petition and Amendment after Notice of Allowance.
U.S. Appl. No. 11/899,004, filed Oct. 3, 2011 Notice of Allowance.
U.S. Appl. No. 11/899,004, filed Sep. 19, 2011 Decision on Petition.
U.S. Appl. No. 11/899,004, filed Jan. 3, 2012 Issue Fee payment.
U.S. Appl. No. 11/899,004, filed Oct. 4, 2012 Amendment after Allowance.
U.S. Appl. No. 11/899,004, filed Oct. 3, 2012 Notice of Allowance.
U.S. Appl. No. 11/899,004, 9/223/2011 Amendment and Request for Continued Examination (RCE).
U.S. Appl. No. 11/899,004, filed Jul. 18, 2011 Notice of Allowance.
U.S. Appl. No. 11/899,004, filed May 10, 2011 Response to Non-Final Office Action.
U.S. Appl. No. 11/899,004, filed Feb. 8, 2011 Non-Final Office Action.
U.S. Appl. No. 12/077,612, filed Oct. 29, 2015 Notice of Abandonment.
U.S. Appl. No. 12/077,612, filed Apr. 9, 2015 Non-Final Office Action.
U.S. Appl. No. 12/077,612, filed Sep. 22, 2014 Amendment and Request for Contiuned Examination (RCE).
U.S. Appl. No. 12/077,612, filed Jan. 2, 2014 Applicant Initiated Interview Summary.
U.S. Appl. No. 12/077,612, filed Mar. 21, 2014 Final Office Action.
U.S. Appl. No. 12/077,612, filed Sep. 22, 2014 Amendment and Request for Continued Examination (RCE).
U.S. Appl. No. 12/077,612, filed Jan. 30, 2014 Response to Non-Final Office Action.
U.S. Appl. No. 12/077,612, filed Aug. 30, 2013 Non-Final Office Action.
U.S. Appl. No. 12/077,612, filed Oct. 26, 2011 Amendment and Request for Continued Examination (RCE).
U.S. Appl. No. 12/077,612, filed May 26, 2011 Final Office Action.
U.S. Appl. No. 12/077,612, filed Mar. 23, 2011 Response to Non-Final Office Action.
U.S. Appl. No. 12/077,612, filed Nov. 16, 2010 Non-Final Office Action.
U.S. Appl. No. 12/096,254, filed Sep. 28, 2015 Notice of Abandonment.
U.S. Appl. No. 12/096,254, filed Feb. 27, 2015 Non-Final Office Action.
U.S. Appl. No. 12/096,254, filed Sep. 22, 2014 Amendment and Request for Continued Examination (RCE).
U.S. Appl. No. 12/096,254, filed Mar. 21, 2014 Final Office Action.
U.S. Appl. No. 12/096,254, filed Dec. 23, 2013 Response to Non-Final Office Action.
U.S. Appl. No. 12/096,254, filed Dec. 17, 2013 Applicant Initiated Interview Summary.
U.S. Appl. No. 12/096,254, filed Aug. 23, 2013 Non-Final Office Action.
U.S. Appl. No. 12/096,254, filed Nov. 30, 2012 Amendment and Request for Contiuned Examination (RCE).
U.S. Appl. No. 12/096,254, filed May 31, 2012 Final Office Action.
U.S. Appl. No. 12/096,254, filed Apr. 4, 2012 Response to Non-Final Office Action.
U.S. Appl. No. 12/096,254, filed Oct. 5, 2011 Non-Final Office Action.
U.S. Appl. No. 13/019,029, filed Mar. 21, 2013 Issue Fee payment.
U.S. Appl. No. 13/019,029, filed Dec. 26, 2012 Notice of Allowance.
U.S. Appl. No. 13/045,070, filed Nov. 17, 2015 Response after Final Action.
U.S. Appl. No. 13/045,070, filed Jul. 7, 2015 Final Office Action.
U.S. Appl. No. 13/045,070, filed May 18, 2015 Applicant Initiated Interview Summary.
U.S. Appl. No. 13/045,070, filed May 15, 2015 Response to Non-Final Office Action.
U.S. Appl. No. 13/045,070, filed Jan. 16, 2015 Non-Final Office Action.
U.S. Appl. No. 13/045,070, filed Nov. 7, 2013 Amendement and request for Continued Examination (RCE).
U.S. Appl. No. 13/045,070, filed May 9, 2013 Final Office Action.
U.S. Appl. No. 13/045,070, filed Dec. 21, 2012 Response to Non-Final Office Action.
U.S. Appl. No. 13/045,070, filed Jun. 22, 2012 Non-Final Office Action.
U.S. Appl. No. 13/045,070, filed Jan. 15, 2016 Notice of Allowance.
U.S. Appl. No. 13/045,070, filed Jan. 15, 2016 Applicant Initiated Interview Summary.
U.S. Appl. No. 13/045,070, filed Jan. 7, 2016 Notice of Appeal Filed.
U.S. Appl. No. 13/045,070, filed Feb. 24, 2016 Issue Fee Payment.
U.S. Appl. No. 13/353,148, filed Aug. 12, 2015 Non-Final Office Action.
U.S. Appl. No. 13/353,148, filed Jul. 6, 2015 Amendment and Request for Continued Examination (RCE).

(56) References Cited

OTHER PUBLICATIONS

U.S. Appl. No. 13/353,148, filed Mar. 3, 2015 Final Office Action.
U.S. Appl. No. 13/353,148, filed Oct. 24, 2014 Response to Non-Final Office Action.
U.S. Appl. No. 13/353,148, filed Oct. 14, 2014 Applicant Initiated Interview Summary.
U.S. Appl. No. 13/353,148, filed Apr. 24, 2014 Non-Final Office Action.
U.S. Appl. No. 13/353,148, filed Apr. 17, 2014 Amendment and Request for Continued Examination (RCE).
U.S. Appl. No. 13/353,148, filed Feb. 25, 2014 Applicant Initiated Interview Summary.
U.S. Appl. No. 13/353,148, filed Oct. 17, 2013 Final Office Action.
U.S. Appl. No. 13/353,148, filed Sep. 11, 2013 Response to Non-Final Office Action.
U.S. Appl. No. 13/353,148, filed Jun. 20, 2013 Non-Final Office Action.
U.S. Appl. No. 13/353,148, filed Feb. 26, 2016 Notice of Abandonment.
U.S. Appl. No. 13/426,400, filed Dec. 4, 2015 Applicant Initiated Interview Summary.
U.S. Appl. No. 13/426,400, filed Dec. 4, 2015 Response to Non-Final Office Action.
U.S. Appl. No. 13/426,400, filed Jul. 2, 2015 Non-Final Office Action.
U.S. Appl. No. 13/426,400, filed Mar. 23, 2015 Amendment and Request for Continued Examination (RCE).
U.S. Appl. No. 13/426,400, filed Dec. 23, 2014 Final Office Action.
U.S. Appl. No. 13/426,400, filed Oct. 2, 2014 Response to Non-Final Office Action.
U.S. Appl. No. 13/426,400, filed May 5, 2014 Non-Final Office Action.
U.S. Appl. No. 13/426,400, filed Feb. 5, 2016 Notice of Allowance.
U.S. Appl. No. 13/426,400, filed May 5, 2016 Issue Fee Payment.
U.S. Appl. No. 13/426,400, filed May 13, 2016 Notice of Allowance.
U.S. Appl. No. 13/529,239, filed Jun. 4, 2015 Final Office Action.
U.S. Appl. No. 13/529,239, filed Mar. 5, 2015 Applicant Initiated Interview Summary.
U.S. Appl. No. 13/529,239, filed Mar. 3, 2015 Response to Non-Final Office Action.
U.S. Appl. No. 13/529,239, filed Sep. 3, 2014 Non-Final Office Action.
U.S. Appl. No. 13/529,239, filed Jun. 30, 2014 Amendment and Request for Continued Examination (RCE).
U.S. Appl. No. 13/529,239, filed May 1, 2014 Applicant Initiated Interview Summary.
U.S. Appl. No. 13/529,239, filed Nov. 18, 2013 Applicant Initiated Interview Summary.
U.S. Appl. No. 13/529,239, filed Dec. 31, 2013 Final Office Action.
U.S. Appl. No. 13/529,239, filed Dec. 3, 2013 Response to Non-Final Office Action.
U.S. Appl. No. 13/529,239, filed Jul. 5, 2013 Non-Final Office Action.
U.S. Appl. No. 13/529,239, filed Jan. 8, 2016 Notice of Abandonment.
U.S. Appl. No. 13/848,436, filed Jan. 21, 2016 Non-Final Office Action.
U.S. Appl. No. 13/848,436, filed Dec. 21, 2015 Response to Restriction Requirement.
U.S. Appl. No. 13/848,436, filed Jul. 22, 2015 Restriction Requirement Filed.
U.S. Appl. No. 13/848,436, filed Nov. 1, 2016 Issue Fee Payment.
U.S. Appl. No. 13/848,436, filed Aug. 2, 2016 Notice of Allowance.
U.S. Appl. No. 13/848,436, filed Jun. 21, 2016 Response to Non-Final Office Action.
U.S. Appl. No. 14/091,010, filed Sep. 4, 2019 Issue Fee Payment.
U.S. Appl. No. 14/091,010, filed Jul. 17, 2019 Notice of Allowance.
U.S. Appl. No. 14/091,010, filed Jun. 6, 2019 Notice of Allowance.
U.S. Appl. No. 14/091,010, filed Jan. 3, 2019 Amendment and Request for Continued Examination (RCE).
U.S. Appl. No. 14/091,010, filed Jul. 3, 2018 Final Office Action.
U.S. Appl. No. 14/091,010, filed Jun. 1, 2018 Response to Non-Final Office Action.
U.S. Appl. No. 14/091,010, filed Dec. 1, 2017 Non-Final Office Action.
U.S. Appl. No. 14/091,010, filed Oct. 18, 2017 Amendment and Request for Continued Examination (RCE).
U.S. Appl. No. 14/091,010, filed Apr. 20, 2017 Final Office Action.
U.S. Appl. No. 14/091,010, filed Mar. 13, 2017 Response to Non-Final Office Action.
U.S. Appl. No. 14/091,010, filed Sep. 12, 2016 Non-Final Office Action.
U.S. Appl. No. 14/300,106, filed Sep. 24, 2015 Notice of Allowance.
U.S. Appl. No. 14/300,106, filed Dec. 22, 2015 Issue Fee Payment.
U.S. Appl. No. 14/449,820, filed Jul. 23, 2018 Final Office Action.
U.S. Appl. No. 14/449,820, filed Nov. 29, 2017 Response to Non-Final Office Action.
U.S. Appl. No. 14/449,820, filed Mar. 2, 2017 Non-Final Office Action.
U.S. Appl. No. 14/449,820, filed Jul. 8, 2019 Non-Final Office Action.
U.S. Appl. No. 14/457,023, filed Mar. 2, 2016 Non-Final Office Action.
U.S. Appl. No. 14/457,023, filed Jun. 30, 2016 Response to Non-Final Office Action.
U.S. Appl. No. 14/457,023, filed Sep. 9, 2016 Final Office Action.
U.S. Appl. No. 14/457,023, filed Nov. 2, 2018 Notice of Appeal Filed.
U.S. Appl. No. 14/457,023, filed May 2, 2018 Final Office Action.
U.S. Appl. No. 14/457,023, filed Dec. 26, 2017 Response to Non-Final Office Action.
U.S. Appl. No. 14/457,023, filed Jun. 23, 2017 Non-Final Office Action.
U.S. Appl. No. 14/457,023, filed Mar. 9, 2017 Amendment and Request for Continued Examination (RCE).
U.S. Appl. No. 14/476,543, filed Sep. 22, 2016 Non-Final Office Action.
U.S. Appl. No. 14/476,543, filed Jun. 22, 2018 Issue Fee Payment.
U.S. Appl. No. 14/476,543, filed Mar. 22, 2018 Notice of Allowance.
U.S. Appl. No. 14/476,543, filed Jan. 17, 2018 Amendment and Request for Continued Examination (RCE).
U.S. Appl. No. 14/476,543, filed Jul. 17, 2017 Final Office Action.
U.S. Appl. No. 14/476,543, filed Mar. 22, 2017 Response to Non-Final Office Action.
U.S. Appl. No. 14/695,674, filed Oct. 30, 2018 Non-Final Office Action.
U.S. Appl. No. 14/695,674, filed Sep. 13, 2018 Amendment and Request for Continued Examination (RCE).
U.S. Appl. No. 14/695,674, filed Mar. 15, 2018 Final Office Action.
U.S. Appl. No. 14/695,674, filed Feb. 2, 2018 Response to Non-Final Office Action.
U.S. Appl. No. 14/695,674, filed Nov. 3, 2017 Non-Final Office Action.
U.S. Appl. No. 14/949,000, filed Dec. 13, 2018 Response to Non-Final Office Action.
U.S. Appl. No. 14/949,000, filed Aug. 28, 2018 Response to Non-Final Office Action.
U.S. Appl. No. 14/949,000, filed Feb. 28, 2018 Non-Final Office Action.
U.S. Appl. No. 14/949,000, filed Jan. 29, 2018 Amendment and Request for Contiuned Examination (RCE).
U.S. Appl. No. 14/949,000, filed Jul. 28, 2017 Final Office Action.
U.S. Appl. No. 15/165,942, filed Nov. 9, 2018 Issue Fee Payment.
U.S. Appl. No. 15/165,942, filed Aug. 13, 2018 Notice of Allowance.
U.S. Appl. No. 15/165,942, filed Jul. 25, 2018 Request for Continued Examination (RCE).
U.S. Appl. No. 15/165,942, filed May 21, 2018 Notice of Allowance.

(56) References Cited

OTHER PUBLICATIONS

U.S. Appl. No. 15/165,942, filed Feb. 8, 2018 Response to Non-Final Office Action.
U.S. Appl. No. 15/165,942, filed Aug. 9, 2017 Non-Final Office Action.
"Vial", Retrieved from http://en.wikipedia.org/w/index.php?title=Vial&oldid=603936258 [Downloaded on May 20, 2014].
Abbott, et al., "Astrocyte-Endothelial Interactions At The Blood-Brain Barrier", *Nat. Rev. Neurosci.*, 7(1):41-53 (2006).
Alam et al., "An Adaptive Strain Estimator for Elastography," IEEE Transactions on Ultrasonics, Ferroelectrics, and Frequency Control, vol. 45, No. 2, Mar. 1998, pp. 461-472.
Amin et al., "Therapy planning and monitoring of tissue ablation by high intensity focused ultrasound (HIFU) using imaging and simulation", Conf Proc IEEE Eng Med Biol Soc. 2008, 4471.
Ammi, et al., "Ultrasonic contrast agent shell rupture detected by inertial cavitation and rebound signals", *IEEE Transactions*, 53(1):126-136 (2006).
Ashikaga, et al., "Transmural Dispersion Of Myofiber Mechanics: Implications For Electrical Heterogeneity In Vivo", *Journal of the American College of Cardiology*, 49(8):909-916 (2007).
Aubry, et al., "Experimental Demonstration Of Noninvasive Transskull Adaptive Focusing Based On Prior Computed Tomography Scans", *The Journal of the Acoustical Society of America*, 113:84 (2003).
Avolio, et al., "Effects of aging on changing arterial compliance and left ventricular load in a northern Chinese urban community", *Circulation*, 68(1):50-58 (1983).
Azuma, et al., "Bubble Generation By Standing Wave In Water Surrounded By Cranium With Transcranial Ultrasonic Beam", *Japanese Journal of Applied Physics*, 44:4625-4630 (2005).
Badke, et al., "Effects Of Ventricular Pacing On Regional Left Ventricular Performance In The Dog", *Am J Physiol Heart Circ Physiol.*, 238:H858-867 (1980).
Baron, et al., "Simulation Of Intracranial Acoustic Fields In Clinical Trials Of Sonothrombolysis", *Ultrasound Med. Biol.*, 35(7):1148-1158 (2009).
Baseri, et al., "Multi-Modality Safety Assessment Of Blood-Brain Barrier Opening Using Focused Ultrasound And Definity Microbubbles: A Short-Term Study", *Ultrasound Med. Biol.*, 6(9):1445-1459 (2010).
Behrens, et al., "Low-Frequency, Low-Intensity Ultrasound Accelerates Thrombolysis Through The Skull", *Ultrasound in Medicine & Biology*, 25:269-273 (1999).
Bercoff, et al., "Supersonic Shear Imaging: A New Technique for Soft Tissue Elasticity Mapping", *IEEE Transactions on Ultrasonics Ferroelectrics and Frequency Control*, 51:396-409 (2004).
Berger, et al., "Single-Beat Noninvasive Imaging Of Cardiac Electrophysiology Of Ventricular Pre-Excitation", *Journal of the American College of Cardiology*, 48:2045-2052 (2006).
Bers, "Cardiac Excitation-Contraction Coupling", *Nature*, 415:198-205 (2002).
Bonnefous, et al, "Time Domain Formulation of Pulse-Doppler Ultrasound and Blood Velocity Estimation by Cross Correlation", *Ultrason Imaging*, 8(2):73-85 (1986).
Borden et al., "Ultrasound Radiation Force Modulates Ligand Availability on Target Contrast Agents", Mol. Imaging, 5:139-147 (2006).
Brekke, et al., "Tissue Doppler Gated (TDOG) Dynamic Three-Dimensional Ultrasound Imaging of the Fetal Heart", *Ultrasound Obstet Gynecol.*, 24(2):192-198 (2004).
Brooks, et al., "Electrical Imaging of the Heart", *IEEE Signal Processing Magazine*, 14:24-42 (1997).
Brundin, et al., "Restorative Therapies in Parkinson's Disease", *Springer Verlag* (2006).
Campbell, et al., "Mechanisms Of Transmurally Varying Myocyte Electromechanics In An Integrated Computational Model", *Philos Transact A Math Phys Eng Sci.*, 366:3361-3380 (2008).
Carman, et al., "Adenosine receptor signaling modulates permeability of the blood-brain barrier", The Journal of Neuroscience, 31(37):13272-13280 (2011).
Caskey, et al., "Direct Observations Of Ultrasound Microbubble Contrast Agent Interaction With The Microvessel Wall", *J. Acoust. Soc. Amer.*, 122(2):1191-1200 (2007).
Caskey, et al., "Microbubble Oscillation In Tubes With Diameters Of 12, 25, And 195 Microns", *Appl. Phys. Lett.*, 88(3):033902-1-033902-3 (2006).
Cavaglia, et al., "Regional Variation In Brain Capillary Density And Vascular Response To Ischemia", *Brain Res.*, 910(1-2):81-93 (2001).
Chan, "Transgenic Nonhuman Primates For Neurodegenerative Diseases", *Reproductive Biology and Endocrinology*, 2:39 (2004).
Chang, et al., "3-D US Frame Positioning Using Speckle Decorrelation and Image Registration", *Ultrasound in Medicine and Biology*, pp. 801-812 (2003).
Chen, et al., "The size of blood-brain barrier opening induced by focused ultrasound is dictated by the acoustic pressure", J. Cereb. Blood Flow Metab., 34:1197-1204 (2014).
Chen, et al., "Architectural Acoustics and Noise: Advancements and Best Practices in Instrumentation for Architectural Acoustics and Noise", *J. Acoust. Soc. Am.; 164th Meeting: Acoustical Society of America*, 132(3, Pt. 2):1977-2018 (Sep. 2012).
Chen, et al., "Engineering Acoustics and ASA Committee on Standards: Sound Intensity Measurements", *J. Acoust. Soc. Am.; 164th Meeting: Acoustical Society of America*, 132(3, Pt. 2):1984 (Sep. 2012).
Chen, et al., "Estimation of Displacement Vectors and Strain Tensors in Elastography Using Angular Insonifications", *IEEE Transactions on Medical Imaging*, 23(12):1479-1489 (2004).
Chen, et al., "Optimization Of Ultrasound Parameters For Cardiac Gene Delivery Of Adenoviral Or Plasmid Deoxyribonucleic Acid By Ultrasound-Targeted Microbubble Destruction", *J. Amer. Coll. Cardiol.*, 42(2):301-308 (2003).
Choi, et al., "Noninvasive, Transcranial And Localized Opening Of The Blood-Brain Barrier Using Focused Ultrasound In Mice", *Ultrasound in Medicine & Biology*, 33(1):95-104 (2007).
Choi, et al., "Spatio-Temporal Analysis Of Molecular Delivery Through The Blood-Brain Barrier Using Focused Ultrasound", *Physics in Medicine and Biology*, 52:5509-5530, (2007).
Choi, et al., "Delivery of pharmacologically-relevant sized molecules through the ultrasound-induced blood-brain barrier opening in vivo", *Neuroscience*, Chicago, IL, USA, Oct. 17-21, 2009.
Choi, et al., "Feasibility Of Transcranial, Localized Drug-Delivery In The Brain Of Alzheimer's-Model Mice Using Focused Ultrasound," *2005 IEEE Ultrasonics Symposium*, pp. 988-991 (Sep. 18-21, 2005).
Choi, et al., "Focused Ultrasound-Induced Molecular Delivery Through The Blood-Brain Barrier", Presented at the IEEE Symp. Ultrason. Ferroelect. Freq. Control, New York, NY, pp. 1192-1195 (2007).
Choi, et al., "Microbubble-size dependence of focused ultrasound-induced blood-brain barrier opening in mice in vivo," *IEEE transactions on Biomedical Engineering*, 57(1):145-154 (2010).
Choi, et al., "Molecules Of Various Pharmacologically-Relevant Sizes Can Cross The Ultrasound-Induced Blood-Brain Barrier Opening In Vivo," *Ultrasound in Medicine & Biology*, 36(1):58-67 (2009).
Choi, et al., "Noninvasive and Transient Blood-Brain Barrier Opening in the Hippocampus of Alzheimer's Double Transgenic Mice Using Pulsed Focused Ultrasound", *Ultrasonic Imaging*, pp. 189-200 (2008).
Choi, et al., "Optimization of Blood-Brain Barrier Opening in Mice using Focused Ultrasound", *2006 IEEE Ultrasounics Symposium* [online], Jun. 2007.
Chomas, et al., "Threshold Of Fragmentation For Ultrasonic Contrast Agents", *J. Biomed. Opt.*, 6(2):141-150 (2001).
Clement, et al., "A Hemisphere Array For Non-Invasive Ultrasound Brain Therapy And Surgery", *Phys Med Biol.*, 45:3707-3719 (2000).
Cobbold, R.S.C., "Foundations of biomedical ultrasound", Biomedical engineering series, Oxford University Press, pp. 422-423 (2006).
Connor, "Simulation Methods And Tissue Property Models For Non-Invasive Transcranial Focused Ultrasound Surgery", *Ph.D. Thesis* (2005).

(56) References Cited

OTHER PUBLICATIONS

Connor, et al., "A Unified Model For The Speed Of Sound In Cranial Bone Based On Genetic Algorithm Optimization", *Physics in Medicine and Biology*, 47:3925-3944 (2002).
Cordeiro, et al., "Transmural Heterogeneity Of Calcium Activity And Mechanical Function In The Canine Left Ventricle", *Am J Physiol. Heart Circ. Physiol.*, 286:H1471-1479 (2004).
Coyle, "Arterial Patterns Of The Rat Rhinencephalon And Related Structures", *Exp. Neurol.*, 49(3): 671-690 (1975).
Coyle, "Spatial Features Of The Rat Hippocampal Vascular System", *Exp. Neurol.*, 58(3): 549-561 (1978).
Coyle, "Vascular Patterns Of The Rat Hippocampal Formation", *Exp. Neurol.*, 52(3): 447-458 (1976).
Crum, et al., "Bjerknes Forces On Bubbles In A Stationary Sound Field", *The Journal of the Acoustical Society of America*, 57(6): 1363-1370 (1975).
Cutnell, et al., (1998). Physics, Fourth Edition. New York. Table of Contents.
Daffertshofer, et al., "Transcranial Low-Frequency Ultrasound-Mediated Thrombolysis In Brain Ischemia: Increased Risk Of Hemorrhage With Combined Ultrasound And Tissue Plasminogen Activator: Results Of A Phase II Clinical Trial", *Stroke*, 36:1441-146 (2005).
Damianou, et al., "Dependence of ultrasonic attenuation and absorption in dog soft tissues on temperature and thermal dose", *J Acoust Soc Am*, 102(1):628-634 (1997).
Datta, et al., "Correlation Of Cavitation With Ultrasound Enhancement Of Thrombolysis", *Ultrasound in Medicine & Biology*, 32(8): 1257-1267 (2006).
De Craene, et al., "Temporal diffeomorphic free-form deformation: Application to motion and strain estimation from 3D echocardiography", Medical Image Analysis, 16(2):427-450 (2012).
Declerck, et al., "Left ventricular motion reconstruction from planar tagged MR images: a comparison", *Phys Med Biol.*, 45(6): 1611-1632 (2000).
Deffieux, et al., "Transcranial Focused Ultrasound For Blood-Brain Barrier Opening—Numerical Simulations With In Vitro Validation In Human And Monkey Skulls", Title page and Table of Contents for the AIUM Annual Convention, San Diego, CA, (2010).
Definition of "spatial filter" retrieved from http://ww.onelook.com/ on May 26, 2015.
DeLong, "Primate Models Of Movement Disorders Of Basal Ganglia Origin", *Trends Neurosci.*, 13(7): 281-285 (1990).
DuBose, et al., "Confusion and Direction in Diagnostic Doppler Sonography", Journal of Diagnostic Medical Sonography, 25(3):173-177 (2009).
Duck, "Physical Properties Of Tissue: A Comprehensive Reference Book", *Academic Press*, London, UK, 1990.
Duerinckx, et al., "In vivo acoustic attenuation in liver: correlations with blood tests and histology", *Ultrasound Imaging*, 14(5):405-413 (1988).
Durrer, et al., "Total Excitation Of The Isolated Human Heart", *Circulation*, 41:899-912 (1970).
Edwards, et al., "Effects of Ischemia on Left-Ventricular Regional Function in the Conscious Dog", *American Journal of Physiology*, 240, H413-H420 (1981).
EPO Search Report and Opinion and Office Action for EP0684017.2 dated Dec. 7, 2009 and Mar. 8, 2010.
Epstein-Barasg, et al., A microcomposite hydrogel for repeated on-demand ultrasound-triggered drug delivery, Biomaterials, 31(19):5208-5217 (2010).
Erpelding, et al., "Bubble-Based Acoustic Radiation Force Using Chirp Insonation To Reduce Standing Wave Effects", *Ultrasound in Medicine & Biology*, 33(2):263-269 (2007).
European Search Report for EP Application No. 10838238, dated May 6, 2014.
Everbach, et al., "Cavitational Mechanisms In Ultrasound-Accelerated Thrombolysis At 1 Mhz", *Ultrasound In Medicine & Biology*, 26(7): 1153-1160 (2000).

Extended European Search Report dated Jan. 23, 2017 in EP Application No. 10818027.
Faris, et al., "Novel Technique For Cardiac Electromechanical Mapping With Magnetic Resonance Imaging Tagging And An Epicardial Electrode Sock", *Ann Biomed Eng.*, 31:430-440 (2003).
Farook, et al., "Preparation Of Microbubble Suspensions By Co-Axial Electrohydrodynamic Atomization", *Med. Eng. Phys.*, 29(7): 749-754 (2007).
Fenster, et al., "Three-dimensional ultrasound imaging", *Phys Med Biol*, 46(5):R67-R99 (2001).
Feshitan et al., "Microbubble Size Isolation by Differential Centrifugation", *Journal of Colloid and Interface Science*, 329: 316-324 (2009).
Fiske, et al., "Special Focus Section: Gene Therapy For Parkinson's Disease", *Experimental Neurology*, 209:28-29 (2008).
Fry, "Transkull Transmission Of An Intense Focused Ultrasonic Beam", *Ultrasound in Medicine & Biology*, 3, p. 179 (1977).
Fry, et al., "A Focused Ultrasound System For Tissue Volume Ablation In Deep Seated Brain Sites", *IEEE 1986 Ultrasonics Symposium*, pp. 1001-1004 (1986).
Fujii, et al., "A new method for attenuation coefficient measurement in the liver", *Journal of Ultrasound Medicine*, 21(7):783-788 (2002).
Fung, (1993). Biomechanics—Mechanical Properties of Living Tissues. New York. Table of Contents.
Ganan-Calvo, et al., "Perfectly Monodisperse Microbubbling By Capillary Flow Focusing", *Phys. Rev. Lett.*, 87(27) Pt 1: 274501-1-274501-4 (2001).
Gaud et al., "Acoustic Characterization of Single Ultrasound Contrast Agent Microbubbles", *The Journal of the Acoustic Society of America*, 124(6): 4091 (2008).
Ghosh, et al., "Cardiac Memory In Patients With Wolff-Parkinson-White Syndrome: Noninvasive Imaging Of Activation And Repolarization Before And After Catheter Ablation", *Circulation*, 118:907-915 (2008).
Giacobini, "Alzheimer Disease, From Molecular Biology To Therapy", *Advances in Experimental Medicine and Biology*, 429:235-245 (1997).
Ginat, et al., "High-resolution ultrasound elastography of articular cartilage in vitro", Proceedings of the 28th IEEE Embs Annual International Conference, New York City, USApp. 6644-6647 (Aug. 30-Sep. 3, 2006).
Greenstein, et al., "Mechanisms Of Excitation-Contraction Coupling In An Integrative Model Of The Cardiac Ventricular Myocyte", *Biophysical Journal*, 90:77-91 (2006).
Greenwald, "Pulse Pressure and Arterial Elasticity", *Qjm-an International Journal of Medicine*, 95(2): 107-112 (2002).
Gupta, et al., "Changes in Passive Mechanical Stiffness of Myocardial Tissue with Aneurysm Formation", *Circulation*, 89:2315-2326 (1994).
Gurev, et al., "Distribution Of Electromechanical Delay In The Heart: Insights From A Three-Dimensional Electromechanical Model", *Biophysical Journal*, 99:745-754 (2010).
Gurev, et al., "In Silico Characterization Of Ventricular Activation Pattern By Electromechanical Wave Imaging", *Supplement to Heart Rhythm.*, 6:S357 (2009).
Heimdal, et al., "Real-time Strain Rate Imaging of the Left Ventricle by Ultrasound", *J Am Soc EchocardioG.*, 11(11): 1013-1019 (1998).
Henderson, et al., "Series Elasticity of Heart Muscle During Hypoxia", *Cardiovascular Research*, 5:10-14 (1971).
Housden, et al., "Ultrasonic imaging of 3D displacement vectors using a simulated 2D array and beamsteering", *Ultrasonics*, 53(2):615-621 (2013).
Hsu, et al., "Noninvasive and targeted gene delivery into the brain using microbubble-facilitated focused ultrasound", PLoS One 8(2): e57682 (Feb. 2013).
Huang, et al. "Watershed Segmentation for Breast Tumor in 2-D Sonography", *Ultrasound in Medicine and Biology*, pp. 625-632 (2004).
Hynynen et al., "Local and reversible blood-brain barrier disruption by noninvasive focused ultrasound at frequencies suitable for transskull sonications" NeuroImage 24 (2005) 12-20.

(56) References Cited

OTHER PUBLICATIONS

Hynynen, et al., "Demonstration Of Potential Noninvasive Ultrasound Brain Therapy Through An Intact Skull", *Ultrasound in Medicine & Biology*, 24(2): 275-283 (1998).
Hynynen, et al., "Noninvasive MR Imaging—Guided Focal Opening Of The Blood-Brain Barrier In Rabbits", *Radiology*, 220(3): 640-646 (2001).
Hynynen, et al., "Trans-Skull Ultrasound Therapy: The Feasibility Of Using Image-Derived Skull Thickness Information To Correct The Phase Distortion", *IEEE Transactions on Ultrasonics, Ferroelectrics and Frequency Control*, 46(3): 752-755, (1999).
Hynynen, et al., "Focal Disruption Of The Blood-Brain Barrier Due To 260-Khz Ultrasound Bursts: A Method For Molecular Imaging And Targeted Drug Delivery", *J. Neurosurg.*, 105(3): 445-454 (2006).
International Preliminary Report on Patentability, dated Apr. 17, 2007 and Written Opinion for PCT/US2005/037669, dated Jun. 13, 2006.
International Preliminary Report on Patentability, dated Apr. 17, 2007 and Written Opinion for PCT/US2005/037670, dated Nov. 22, 2006..
International Preliminary Report on Patentability, dated Jun. 11, 2008 and Written Opinion for PCT/US2006/061809, dated Oct. 4, 2007.
International Preliminary Report on Patentability, dated Nov. 14, 2007 and Written Opinion for PCT/US2006/018454, dated Aug. 9, 2007.
International Search Report and Written Opinion dated Jul. 17, 2012 in International Application No. PCT/US12/34136.
International Search Report and Written Opinion dated Oct. 18, 2012 in International Application No. PCT/US12/35685.
International Search Report and Written Opinion for PCT/US2006/036460, dated Sep. 5, 2007; International Preliminary Report dated Mar. 26, 2008.
International Search Report and Written Opinion for PCT/US2009/056513, dated Oct. 30, 2009.
International Search Report and Written Opinion for PCT/US2009/052563 dated Oct. 8, 2009.
International Search Report and Written Opinion for PCT/US2009/056565 dated Nov. 2, 2009.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2011/034704, dated Aug. 18, 2011.
International Search Report for PCT/US2007/019149 dated Feb. 29, 2008.
Jagannathan, et al., "High-Intensity Focused Ultrasound Surgery Of The Brain: Part 1—A Historical Perspective With Modem Applications", *Neurosurgery*, 64(2): 201-211 (2009).
Jasaityte, et al., "Current state of three-dimensional myocardial strain estimation using echocardiography", *J Am Soc Echocardiogr.*, 26(1): 15-28 (2013).
Jensen, et al., "Calculation Of Pressure Fields From Arbitrarily Shaped, Apodized, And Excited Ultrasound Transducers", *IEEE Transactions on Ultrasonics, Ferroelectrics and Frequency Control*, 39(2): 262-267 (1992).
Kallel, et al., "A Least-Squares Strain Estimator For Elastography", *Ultrasonic Imaging*, 19:195-208 (1997).
Kanai, et al. "Propagation of Spontaneously Actuated Pulsive Vibration in Human Heart Wall and In Vivo Viscoelasticity Estimation", *IEEE Transactions on Ultrasonics, Ferroelectrics, and Frequency Control*, 52(11): 1931-1942 (2005).
Kanai, et al., "A New Method for Measuring Small Local Vibrations in the Heart Using Ultrasound", *IEEE Transactions on Biomedical Engineering*, 40(12): 1233-1242 (1993).
Kanai, et al., "Myocardial Rapid Velocity Distribution", *Ultrasound Med Biol.*, 27(4): 481-498 (2001).
Kanai, et al., "Transcutaneous Measurement of Frequency Dispersion in the Regional Pulse Wave Velocity", *2000 IEEE Ultrasonics Symposium*, pp. 1-4 (2000).
Kaufman, et al., "Ultrasound Simulation In Bone," *IEEE Transactions on Ultrasonics Ferroelectrics and Frequency Control*, 55(6): 1205-1218 (2008).
Kawabata, et al., "Chemo-thermal approach for efficient ultrasonic tumor treatment with phase change nano droplet", IEEE Int. Ultrasonics Symp., Oct. 18-21, 2011 Orlando, Florida, pp. 9-12.
Kim, et al., "Multifunctional microbubbles and nanobubbles for photoacoustic and ultrasound imaging", J Biomed Opt., 15(1): 010510-1-010510-3 (Jan./Feb. 2010).
Kimber, et al., "A Comparison Of Unipolar And Bipolar Electrodes During Cardiac Mapping Studies", *Pacing Clin Electro.*, 19:1196-1204 (1996).
Kinoshita, et al., "Noninvasive Localized Delivery Of Herceptin To The Mouse Brain By MRI-Guided Focused Ultrasound-Induced Blood-Brain Barrier Disruption", *Proceedings of the National Academy of Sciences*, 103 (31): 11719-11723 (2006).
Kinoshita, et al., "Targeted Delivery Of Antibodies Through The Blood—Brain Barrier By MRI-Guided Focused Ultrasound", *Biochemical and Biophysical Research Communications*, 340:1085-1090 (2006).
Klein, et al., "Interdependency Of Local Capillary Density, Blood Flow, And Metabolism In Rat Brains", *Amer. J. Physiol.*, 251(6) Pt 2: H1333-H1340 (1986).
Klempner, et al., "Neutrophil Plasma Membranes I. High-Yield Purification Of Human Neutrophil Plasma Membrane Vesicles By Nitrogen Cavitation And Differential Centrifugation", *Journal of Cell Biology*, 86:21-28 (1980).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Konofagou, et al. "Elastographic Imaging of the Strain Distribution at the Anterior Cruciate Ligament and ACL-Bone Insertions", *Proceedings of the 2005 IEEE 27th Annual International Conference of the Engineering In Medicine and Biology Society*, pp. 972-975 (Shanghai, China Sep. 1-4, 2005).
Konofagou, et al., "Ultrasound-Induced Blood-Brain Barrier Opening", Current Pharmaceutical Biotechnology, 13(7):1332-1345 (2012).
Konofagou, et al., "A New Elastographic Method for Estimation and Imaging of Lateral Strains, Corrected Axial Strains and Poison's Ratios in Tissues", *Ultrasound in Medicine and Biology*, 24(8):1183-1199 (1998).
Konofagou, et al., "Mechanism And Safety At The Threshold Of The Blood-Brain Barrier Opening In Vivo", *International Society on Therapeutic Ultrasound (ISTU)*, Aix-en-Provence, France, Sep. 21-24, 2009.
Konofagou, et al., "Myocardial Elastography—Feasibility Study In Vivo", *Ultrasound Med & Biol.*, 28(4):475-482 (2002).
Konofagou, et al., "Noninvasive electromechanical wave imaging and conduction-relevant velocity estimation in vivo", *Ultrasonics*, 50(2):208-215 (2010).
Konofagou, et al., "Noninvasive Electromechanical Wave Imaging And Conduction Velocity Estimation In Vivo", *2007 IEEE Ultrasonics Symposium*, pp. 969-972 (2007).
Konofagou, et al., "Three-Dimensional Motion Estimation in Elastography", *IEEE Proceedings of the Symposium of Ultrasonics, Ferroelectrics and Frequency Control in Sendai, Japan*, pp. 1745-1748 (1998).
Korecka, et al., "Cell-Replacement And Gene-Therapy Strategies For Parkinson's And Alzheimers Disease", Regen. Med., 2(4): 425-446 (2007).
Kremkau, et al., "Ultrasonic Attenuation And Propagation Speed In Normal Human Brain", *The Journal of the Acoustical Society of America*, 70:29 (1981).
Kunz, et al., "The Finite Difference Time Domain Method For Electromagnetics," *CRC Press*, Boca Raton, USA (1993).
Kvale, et al., "Size Fractionation Of Gas-Filled Microspheres By Flotation", *Separations Technol.*, 6(4): 219-226 (1996).
Lai, et al., "Introduction to Continuum Mechanics" (Pergamon Pr). 3rd Ed. (1993).

(56) References Cited

OTHER PUBLICATIONS

Lee, et al., "Improving Stereotactic Surgery Using 3-D Reconstruction", *IEEE Engineering in Medicine and Biology Magazine*, 21:109-116 (2002).
Lee, et al., "Theoretical Quality Assessment Of Myocardial Elastography With In Vivo Validation", *IEEE Transactions, Ultrasonics, Ferroelectrics and Frequency Control*, 54:2233-2245 (2007).
Liu et al., "Opening of the Blood-Brain Barrier By Low-Frequency (28-kHz) Ultrasound: A Novel Pinhole-Assisted Mechanical Scanning Device", Ultrasound in Med & Biol., vol. 36, Issue 2, Feb. 2010, pp. 325-335.
Liu, et al., "Hemorrhage Detection During Focused-Ultrasound Induced Blood-Brain-Barrier Opening By Using Susceptibility-Weighted Magnetic Resonance Imaging", *Ultrasound in Med. & Biol.*, 34(4): 598-606 (2008).
Liu, et al., "Magnetic Resonance Imaging Enhanced By Superparamagnetic Iron Oxide Particles: Usefulness For Distinguishing Between Focused Ultrasound-Induced Blood-Brain Barrier Disruption And Brain Hemorrhage", *J. of Magnetic Resonance Imaging*, 29:31-38 (2009).
Long et al., "An integrated system for therapy planning of high intensity focused ultrasound", Electro/Information Technology, 2008. EIT 2008. IEEE International Conference on May 18-20, 2008, pp. 461-464.
Lu, et al., "Design And Experiment Of 256-Element Ultrasound Phased Array For Noninvasive Focused Ultrasound Surgery", *Ultrasonics*, 44:e325-e330 (2006).
Luo, et al., "A Fast Normalized Cross-Correlation Method For Motion Estimation", *IEEE Transactions, Ultrasonics, Ferroelectrics and Frequency Control*, 57(6): 1347-1357 (2010).
Luo, et al., "High-Frame Rate, Full-View Myocardial Elastography With Automated Contour Tracking In Murine Left Ventricles In Vivo", *IEEE Transactions, Ultrasonics, Ferroelectrics and Frequency Control*, 55(1): 240-248 (2008).
Luo, et al., "Myocardial Elastography At Both High Temporal And Spatial Resolution For The Detection Of Infarcts", *Ultrasound Med. Biol.*, 33(8): 1206-1223 (2007).
Luo, et al., "Pulse Wave Imaging Of Normal And Aneurysmal Abdominal Aortas In Vivo", *IEEE Trans. Med. Imaging*, 28(4): 477-486 (2009).
Maleke, et al., "In Vivo Feasibility Of Real-Time Monitoring Of Focused Ultrasound Surgery (FUS) Using Harmonic Motion Imaging (HMI)", *IEEE Trans. Biomed. Eng.*, 57(1): 7-11 (2010).
Maleke, et al., "Single-Element Focused Ultrasound Transducer Method For Harmonic Motion Imaging", *Ultrasonic Imaging*, 28(3): 144-158 (2006).
Marquet, et al., "Non-Invasive Transcranial Ultrasound Therapy Based On A 3D CT Scan: Protocol Validation And In Vitro Results", *Phys. Med. Biol.*, 54:2597-2613 (2009).
Mazziotta, et al., "A Probabilistic Atlas Of The Human Brain: Theory And Rationale For Its Development The International Consortium For Brain Mapping (ICBM)", *Neuroimage*, 2:89-101 (1995).
McDannold, et al., "Targeted Disruption Of The Blood-Brain Barrier With Focused Ultrasound: Association With Cavitations Activity", *Physics in Medicine and Biology*, 51:793-808 (2006).
McDannold, et al., "Use Of Ultrasound Pulses Combined With Definity For Targeted Blood-Brain Barrier Disruption: A Feasibility Study", *Ultrasound In Medicine & Biology*, 33(4): 584-590 (2007).
McDannold, et al., "Blood-Brain Barrier Disruption Induced by Focused Ultrasound and Circulating Preformed Microbubbles Appears to be Characterized by the Mechanical Index", *Ultrasound Med Biol.*, 34(5):834-840 (2008).
McDannold, et al., "MRI-Guided Targeted Blood-Brain Barrier Disruption With Focused Ultrasound: Histological Findings In Rabbits", *Ultrasound Med. Biol.*, 31(11): 1527-1537 (2005).
McLaughlin, et al., "Piezoelectric Sensor Determination of Arterial Pulse Wave Velocity", *Physiol Meas.*, 24(3): 693-702 (2003).

McNally, et al., "Computer Vision Elastography: Speckle Adaptive Motion Estimation for Elastography Using Ultrasound Sequences", *IEEE Transactions on Medical Imaging*, 24(6):755-766 (2005).
Melodelima, et al., "Thermal Ablation By High-Intensity-Focused Ultrasound Using A Toroid Transducer Increases The Coagulated Volume. Results Of Animal Experiments", *Ultrasound in Medicine & Biology*, 35(3): 425-435 (2009).
Mitri, et al., "Chirp Imaging Vibro-Acoustography For Removing The Ultrasound Standing Wave Artifact", *IEEE Transactions on Medical Imaging*, 24(10): 1249-1255 (2005).
Mychaskiw, et al., "Optison (FS069) Disrupts The Blood-Brain Barrier In Rats", *Anesthesia & Analgesia*, 91:798 (2000).
Nichols, et al., "Vascular Impedance. In McDonald's: Blood Flow in Arteries: Theoretical, Experimental and Clinical Principles", *E. Arnold. London, Oxford University Press*, Table of Contents (1998).
Ohtani, et al., "Transmural Ultrasound-Based Visualization of Patterns of Action Potential Wave Propagation in Cardiac Tissue", Annals Biomedical Engineering, 38(10):3112-3123 (2010).
Ophir, et al., "Elastography: A Quantitative Method For Imaging The Elasticity Of Biological Tissues", *Ultrasonic Imaging*, 3(2): 111-134 (1991).
Otani, "Use of ultrasound imaging to map propagating action potential waves in the heart", *Computers in Cardiology*, 36:617-620 (2009).
Palmeri, et al., "Characterizing acoustic attenuation of homogeneous media using focused impulsive acoustic radiation force", *Ultrason Imaging*, 28(2): 114-128 (2006).
Papadakis, Emmauel P., "Ultrasonic Instruments & Devices", Academic Press, 8 pages (1999).
Pardridge, "Drug Targeting To The Brain", *Pharmaceutical Research*, 24:1733-1744 (2007).
Pardridge, "The Blood-Brain Barrier: Bottleneck In Brain Drug Development", *NeuroRx*, 2:3-14 (2005).
Patel, et al., "GDNF Delivery For Parkinson's Disease", *ACTA Neurochirurgica-Supplementum*, 97(2): 135-154 (2007).
Pernot, et al., "ECG-Gated, Mechanical And Electromechanical Wave Imaging Of Cardiovascular Tissues In Vivo", *Ultrasound in Medicine & Biology*, 33(7):1075-1085 (2007).
Pernot, et al., "Electromechanical Imaging Of The Myocardium At Normal And Pathological States", *2005 IEEE Ultrasonics Symposium*, pp. 1091-1094 (2005).
Philippens, "Non-Human Primate Models For Parkinson's Disease", *Drug Discovery Today: Disease Models*, 5:105-111 (2008).
Pichardo, et al., "Multi Frequency Characterization Of Speed Of Sound For Longitudinal Transmission On Freshly Excised Human Skulls" *9th International Society on Therapeutic Ultrasound*, p. 136 (2009.).
Prinzen, et al., "The Time Sequence Of Electrical And Mechanical Activation During Spontaneous Beating And Ectopic Stimulation", *Eur. Heart J.*, 13:535-543 (1992).
Provost, et al., "Electromechanical Wave Imaging Of Normal And Ischemic Hearts In Vivo", *IEEE Trans. Med. Imaging*, 29:625-635 (2010).
Provost, et al., "Imaging the electromechanical activity of the heart in vivo", *PNAS*, 108(21):8565-8570 (2011).
Provost, et al., "Mapping of cardiac electrical activation with electromechanical wave imaging: An in silico-in vivo reciprocity study", *Heart Rhythm.*, 8(5):752-759 (2011).
Qin, et al., "Acoustic Response of Compilable Microvessels Containing Ultrasound Contrast Agents", *Phys. Med. Biol.*, 51:5065-5088 (2006).
Qin, et al., "The Natural Frequency of Nonlinear Oscillation of Ultrasound Contrast Agents in Microvessels", *Ultrasound in Med. & Biol.*, 33(7):1140-1148 (2007).
Ramanathan, et al., "Activation And Repolarization Of The Normal Human Heart Under Complete Physiological Conditions", *Proceedings of the National Academy of Sciences*, 103:6309-6314 (2006).
Ramanathan, et al., "Noninvasive Electrocardiographic Imaging For Cardiac Electrophysiology And Arrhythmia", *Nat Med.*, 10:422-428 (2004).
Raymond, et al., "Ultrasound Enhanced Delivery Of Molecular Imaging And Therapeutic Agents In Alzheimer's Disease Mouse Models", *PLoS One*, 3(5):e2175 (2008).

(56) References Cited

OTHER PUBLICATIONS

Rice, et al., "Approximate Model Of Cooperative Activation And Crossbridge Cycling In Cardiac Muscle Using Ordinary Differential Equations", *Biophys. J.*, 95:2368-2390 (2008).
Rockenstein, et al., "Transgenic Animal Models Of Neurodegenerative Diseases And Their Application To Treatment Development", *Adv. Drug Del. Rev.*, 59(11):1093-1102 (2007).
Rogers, et al., "Age-Associated Changes in Regional Aortic Pulse Wave Velocity", *J Am Coll Cardiol.*, 38(4):1123-1129 (2001).
Roth, "Influence of a Perfusing Bath on the Foot of the Cardiac Action Potential", *Circulation Research*, 86:E19-E22 (2000).
Sabraoui, et al., "Feedback Loop Process to Control Acoustic Cavitation", *Ultrasonics Sonochemistry*, 18(2):589-594 (2011).
Samuel, et al., "An Ex Vivo Study Of The Correlation Between Acoustic Emission And Microvascular Damage", *Ultrasound Med. Biol.*, 35(9):1574-1586 (2009).
Sanberg, et al., "Brief Communication: Neural Transplants Disrupt The Blood-Brain Barrier And Allow Peripherally Acting Drugs To Exert A Centrally Mediated Behavioral Effect", *Experimental Neurology*, 102:149-152 (1988).
Sandrin, et al., "Time-Resolved Pulsed Elastography with Ultrafast Ultrasonic Imaging", *Ultrason. Imaging*, 21(4): 259-72 (1999).
Sarvazyan, et al., "Shear Wave Elasticity Imaging: A New Ultrasonic Technology of Medical Diagnostics", *Ultrasound Med Biol.*, 24(9): 1419-1435 (1998).
Sassaroli, et al., "Cavitation Threshold of Microbubbles in Gel Tunnels by Focused Ultrasound", *Ultrasound in Med. & Biol.*, 33(10):1651-1660 (2007).
Sassaroli, et al., "Forced Linear Oscillations of Microbubbles in Blood Capillaries", *J. Acoust. Soc. Am.*, 115(6):3235-3243 (2004).
Sassaroli, et al., "Resonance Frequency of Microbubbles in Small Blood Vessels: a Numerical Study", *Phys. Med. Biol.*, 50:5293-5305 (2005).
Schenk, et al., "Immunization With Amyloid-Beta Attenuates Alzheimer-Disease-Like Pathology In The PDAPP Mouse", *Nature*, 400:173-177 (1999).
Scher, et al., "The Pathway Of Ventricular Depolarization In The Dog", *Circ Res.*, 4:461-469 (1956).
Schilling, et al., "Simultaneous Endocardial Mapping In The Human Left Ventricle Using A Noncontact Catheter: Comparison Of Contact And Reconstructed Electrograms During Sinus Rhythm", *Circulation*, 98:887-98 (1998).
Sengupta, et al., "Electromechanical Activation Sequence In Normal Heart", *Heart Fail Clin.*, 4:303-314 (2008).
Sheeran et al., "Formulation and Acoustic Studies of a New Phase-Shift Agent for Diagnostic and Therapeutic Ultrasound," Langmuir 27:10412-10420 (2011).
Shehata, et al., "Myocardial Tissue Tagging With Cardiovascular Magnetic Resonance", *Journal of Cardiovascular Magnetic Resonance*, 11:55 (2009).
Sheikov, et al., "Brain Arterioles Show More Active Vesicular Transport Of Blood-Borne Tracer Molecules Than Capillaries And Venules After Focused Ultrasound-Evoked Opening Of The Blood-Brain Barrier", *Ultrasound Med. Biol.*, 32(9): 1399-1409 (2006).
Sheikov, et al., "Cellular Mechanisms Of The Blood-Brain Barrier Opening Induced By Ultrasound In Presence Of Microbubbles", *Ultrasound Med. Biol.*, 30(7): 979-989 (2004).
Sheikov, et al., "Effect Of Focused Ultrasound Applied With An Ultrasound Contrast Agent On The Tight Junctional Integrity Of The Brain Microvascular Endothelium", *Ultrasound Med. Biol.*, 34(7): 1093-1104 (2008).
Shinna, et al., "Realtime tissue elasticity imaging using the combined autocorrelation method", J. Med. Ultrasonics, 29(autumn):119-128 (2002).
Siegel, et al., "Neurotrophic Factors In Alzheimer's And Parkinson's Disease Brain", *Brain Research Reviews*, 33:199-227 (2000).
Silva, "Nanotechnology Approaches to Crossing the Blood-Brain Barrier and Drug Delivery to the CNS", *BMC Neruosci.*, 9(Suppl 3):S4 (2008).

Sinkus, et al., "High-Resolution Tensor MR Elastography for Breast Tumour Detection", *Phys Med Biol.*, 45(6): 1649-1664 (2000).
Sirsi, et al., "Effect Of Microbubble Size On Fundamental Mode High Frequency Ultrasound Imaging In Mice", *Ultrasound in Med. & Bio.*, 36(6): 935-948 (2010).
Spach, et al., "Extracellular Discontinuities in Cardiac Muscle—Evidence for Capillary Effects on the Action Potential Foot", *Circulation Research*, 83:1144-1164 (1998).
Spalazzi et al., "Elastographic Imaging of Strain Distribution within the Anterior Cruciate Ligament and at the AGL-Bone Insertions," IEEE Ultrasonics Symposium, Sep. 2005, pp. 1755-1758.
Stewart, et al., "Blood-Eye Barriers In The Rat: Correlation Of Ultrastructure With Function", *J. Comp. Neurol.*, 340(4): 566-576 (1994).
Stieger, et al., "Enhancement Of Vascular Permeability With Low-Frequency Contrast-Enhanced Ultrasound In The Chorioallantoic Membrane Model", *Radiology*, 243(1): 112-121 (2007).
Styner, et al., "Automatic Brain Segmentation In Rhesus Monkeys" *2007 Medical Imaging, Proc. of SPIE*, 6512:65122L-1-65122L-8 (2007).
Sutherland, "Color Doppler Myocardial Imaging—Potential Applications in Acquired and Congenital Heart-Disease", *Acta Paediatr.*, 84:40-48 (1995).
Sykova, et al., "Diffusion In Brain Extracellular Space", *Physiol. Rev.*, 88(4): 1277-1340 (2008).
Talu, et al., "Tailoring The Size Distribution Of Ultrasound Contrast Agents: Possible Method For Improving Sensitivity In Molecular Imaging" *Mol. Imag.*, 6(6): 384-392 (2007).
Tang, et al., "Standing-Wave Suppression For Transcranial Ultrasound By Random Modulation", *IEEE transactions on Biomedical Engineering*, 57(1):203-205 (2010).
Tanter, et al., "Focusing And Steering Through Absorbing And Aberrating Layers: Application To Ultrasonic Propagation Through The Skull", *The Journal of the Acoustical Society of America*, 103:2403-2410 (1998).
Tanter, et al., "Ultrafast Compound Imaging for 2-D Motion Vector Estimation: Application to Transient Elastography", *IEEE Trans Ultrason Ferroelectr Freq Control*, 49(10): 1363-74 (2002).
Tavarozzi, et al., "Magnetocardiography: Current Status And Perspectives Part II: Clinical Applications", Ital Heart J., 3:151-165 (2002).
Techavipoo, et al., "Temperature dependence of ultrasonic propagation speed and attenuation in excised canine liver tissue measured using transmitted and reflected pulses", *The Journal of Acoustical Society of America*, 115(6):2859-2865 (2004).
Treat, et al., "Targeted Delivery Of Doxorubicin To The Rat Brain At Therapeutic Levels Using MRI-Guided Focused Ultrasound", *Int. J. Cancer*, 121(4): 901-907 (2007).
Tung, et al., "Feasibility of Noninvasive Cavitation-Guided Blood-Brain Barrier Opening Using Focused Ultrasound and Microbubbles in Nonhuman Primates", *Applied Physics Letters*, 98(16):163704 (2001).
Tung, et al., "Identifying The Inertial Cavitation Threshold And Skull Effects In A Vessel Phantom Using Focused Ultrasound And Microbubbles," *Ultrasound in Medicine & Biology*, 36(5): 840-852 (2010).
Tung, et al., "Identifying The Inertial Cavitation Threshold In A Vessel Phantom Using Focused Ultrasound And Microbubbles," *The Journal of the Acoustical Society of America*, 124:2486 (2008).
Tung, et al., "Noninvasive In Vivo Cavitation Threshold Detection During Blood-Brain Barrier Opening Using Focused Ultrasound and the Contrast Agent and Definity," *Joint 159th Meeting of the Acoustic Society of America*, (Apr. 19, 2010).
Tuszynski, et al., "A Phase 1 Clinical Trial Of Nerve Growth Factor Gene Therapy For Alzheimer Disease," *Nature Medicine*, 11:551-555 (2005).
Tuszynski, et al., "Nerve Growth Factor Gene Therapy In Alzheimer Disease," *Alzheimer Disease & Associated Disorders*, 21:179-189 (2007).
Unger, E.C et al., "Therapeutic Applications of Lipid-Coated Microbubbles", *Advanced Drug Delivery Reviews*, 56(9):1291-1314 (2004).

(56) References Cited

OTHER PUBLICATIONS

Vaezy et al., "Real-time visualization of high-intensity focused ultrasound treatment using ultrasound imaging", Ultrasound Med Biol., Jan. 2001, 27(1), pp. 33-42.
Vappou, et al., "Quantitative Viscoelastic Parameters Measured By Harmonic Motion Imaging", *Phys. Med. Biol.*, 54:3579-3595 (2009).
Walker, et al., "A Fundamental Limit on Delay Estimation Using Partially Correlated Speckle Signals", *IEEE Transactions, Ultrasonics, Ferroelectrics and Frequency Control*, 42(2): 301-308 (1995).
Walker, et al., "A Fundamental Limit On The Performance Of Correlation Based Phase Correction And Flow Estimation Techniques", *IEEE Transactions, Ultrasonics, Ferroelectrics and Frequency Control*, 41(5): 644-654 (1994).
Wang et al., "Qualitative And Quantitative Analysis Of The Molecular Delivery Through The Ultrasound-Enhanced Blood-Brain Barrier Opening In The Murine Brain," presented at the IEEE Symp. Ultrason. Ferroelectr. Freq. Control, Beijing, China, 2008.
Wang, et al., "A Composite Imaging Technique for High Frame-Rate and Full-View Cardiovascular Ultrasound and Elasticity Imaging", *IEEE Transactions, Ultrasonics, Ferroelectrics and Frequency Control*, 55(10): 2221-2233 (2008).
Wang, et al., "A Composite Imaging Technique for High Frame-Rate and Full-View Cardiovascular Ultrasound and Elasticity Imaging", *IEEE International Ultrasonics Symposium*, New York, NY, Oct. 28-31, 2007.
Wang, et al., "Increased Aortic Stiffness Assessed by Pulse Wave Velocity in Apolipoprotein E-Deficient Mice", *Am J Physiol Heart Circ Physiol.*, 278(2): H428-34 (2000).
Wenk, "A Primate Model Of Alzheimer's Disease", *Behavioural Brain Research*, 57:117-122 (1993).
White, et al., "Longitudinal And Shear Mode Ultrasound Propagation In Human Skull Bone", *Ultrasound In Medicine & Biology*, 32:1085-1096 (2006).
Wyman, et al., "Mapping Propagation Of Mechanical Activation In The Paced Heart With MRI Tagging", *Am J Physiol Heart Circ Physiol*, 276:H881-891 (1999).
Xu, et al., "Controllable Gas-Liquid Phase Flow Patterns And Monodisperse Microbubbles In A Microfluidic T-Junction Device", *Appl. Phys. Lett.*, 88(13): 133506-1-133506-3 (2006).
Yin, et al., "A Numerical Study Of Transcranial Focused Ultrasound Beam Propagation At Low Frequency", *Physics in Medicine and Biology*, 50:1821-1836 (2005).
Yuh, et al. "Delivery of Systemic Chemotherapeutic Agent to Tumors by Using Focused Ultrasound: Study in a Murine Model", *Radiology*, 234(2): 431-437 (2005).
Zerhouni, et al., "Human Heart: Tagging with MR Imaging—A Method for Noninvasive Assessment of Myocardial Motion", *Radiology*, 169(1): 59-63 (1988).
Zhang, et al., "Noninvasive Three-Dimensional Electrocardiographic Imaging Of Ventricular Activation Sequence", *Am J Physiol Heart Circ Physiol.*, 289:H2724-32 (2005).
Zheng et al., "A Targeting Method Based on Acoustic Backscatter for Treatment Planning in Tissue Ablation Using Focused Ultrasound", IEEE Trans on Biomed Eng. vol. 57, No. 1, Jan. 2010, pp. 71-79.
Zheng, et al. "High Resolution Ultrasound Elastomicroscopy Imaging of Soft Tissues: System Development and Feasibility; Ultrasound Elastomicroscopy", *Physics in Medicine and Biology*, 49(17):3925-3938 (2004).
Zheng, et al., "Ultrasonic measurement of depth-dependent transient behaviors of articular cartilage under compression", Journal of Biomechanics, 38:1830-1837 (2005).
Zheng, et al., "Ultrasound-Driven Microbubble Oscillation And Translation Within Small Phantom Vessels", *Ultrasound Med. Biol.*, 33(12): 1978-1987 (2007).
Ziadloo et al., "Real-time 3D image-guided HIFU therapy", Conf Proc IEEE Eng Med Biol Soc. 2008, 4459-62.
Zlokovic, "The Blood-Brain Barrier In Health And Chronic Neurodegenerative Disorders", *Neuron*, 57(2): 178-201 (2008).
Zwanenburg, et al., "Timing Of Cardiac Contraction In Humans Mapped By High-Temporal-Resolution MRI Tagging: Early Onset And Late Peak Of Shortening In Lateral Wall", *Am J Physiol Heart Circ Physiol.*, 286:H1872-1880 (2004).

\* cited by examiner

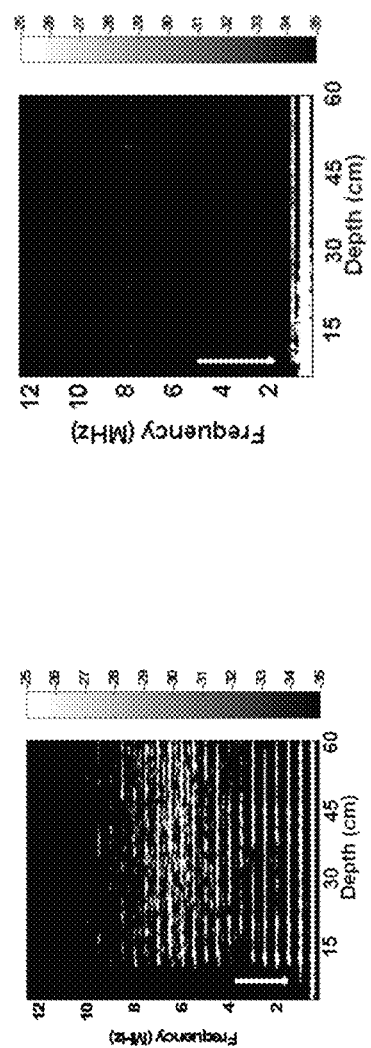

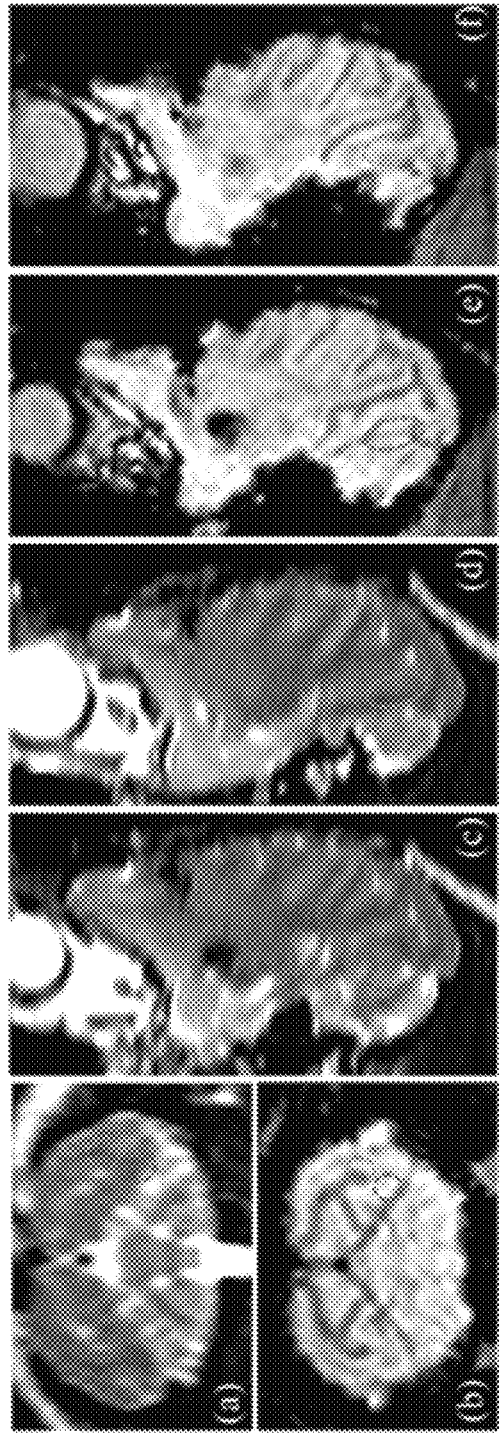

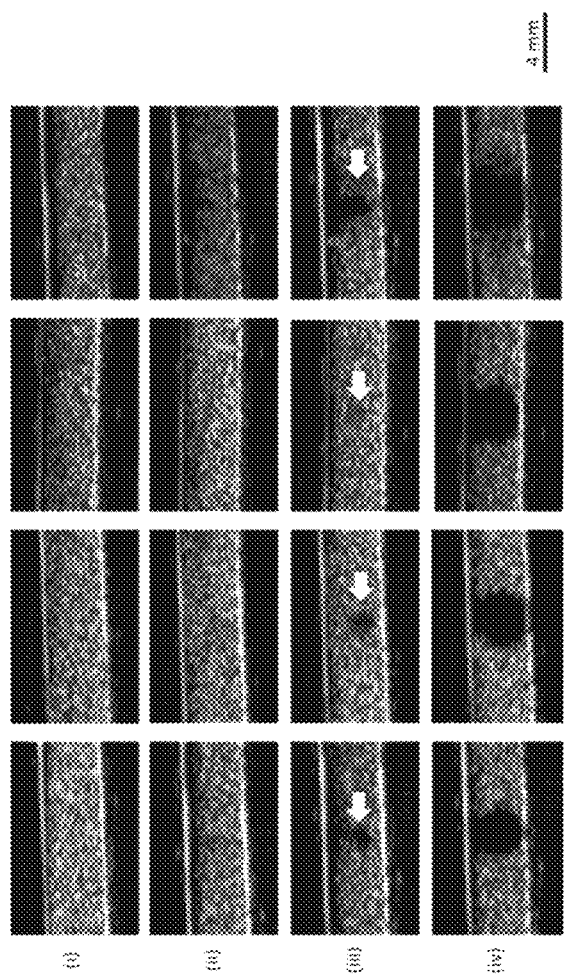

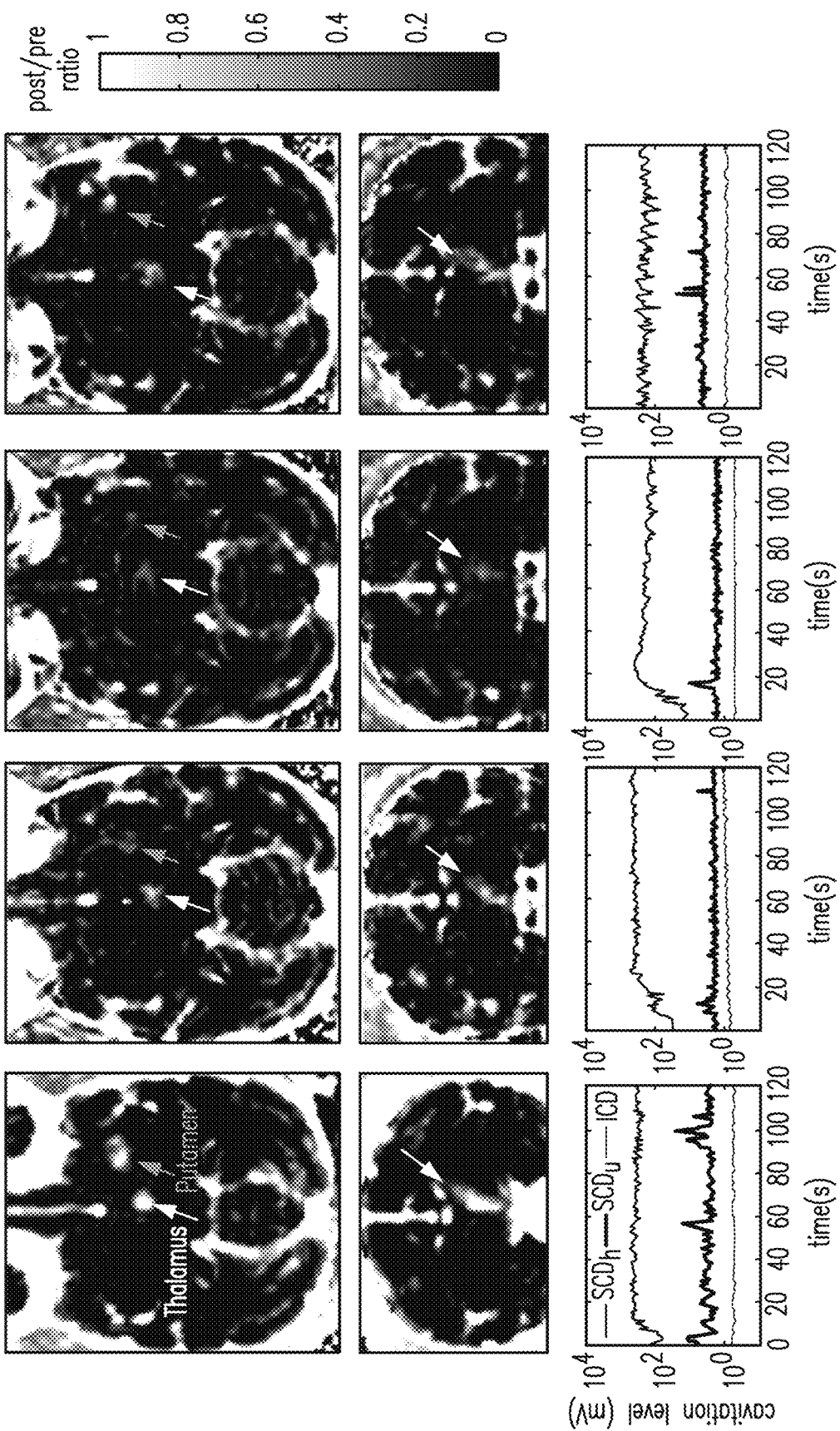

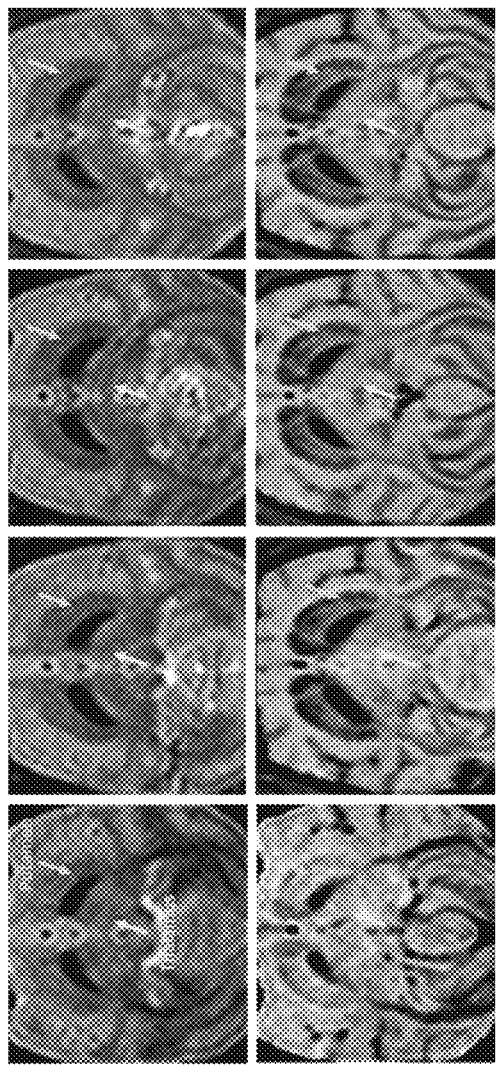

SYSTEMS AND METHODS FOR OPENING OF A TISSUE BARRIER IN PRIMATES

CROSS REFERENCE TO RELATED APPLICATIONS

This application is a continuation of U.S. patent application Ser. No. 14/091,010, filed on Nov. 26, 2013, which is a continuation-in-part of International Patent Application No. PCT/US2012/039708, filed on May 25, 2012, which claims priority to U.S. Provisional Application No. 61/490,440, filed on May 26, 2011, the disclosure of each of which is incorporated by reference herein in its entirety. This application is also related to U.S. patent application Ser. No. 12/077,612, filed Mar. 19, 2008, International Patent Application No. PCT/US2009/056565, filed Sep. 10, 2009, International Patent Application No. PCT/US2010/049681, filed on Sep. 21, 2010, and U.S. patent application Ser. No. 13/426,400, filed on Mar. 21, 2012, the disclosure of each of which is incorporated by reference herein in its entirety.

STATEMENT REGARDING FEDERALLY-SPONSORED RESEARCH

This invention was made with government support under Grant Nos. R01AG038961, R01 EB009041 and R21 EY018505 awarded by the National Institutes of Health and CAREER 0644713 and MH059244 awarded by the National Science Foundation. The government has certain rights in the invention.

BACKGROUND

Certain neurological disorders and neurodegenerative diseases, such as Alzheimer's disease and Parkinson's disease, can be difficult to treat due at least in part to the impermeability of the blood-brain barrier (BBB). Mechanical stress induced by the activation of microbubbles in an acoustic field is one noninvasive technique to temporarily open the BBB, and can be performed without damaging the surrounding tissue. BBB opening with focused ultrasound (FUS) can be performed in some animals, including mice, rabbits, rats, and pigs. However, extending this technique to other species can be difficult due to differences in physiology and anatomy.

A passive cavitation detector (PCD) can be used to transcranially acquire acoustic emissions from interaction between a microbubble and brain tissue during BBB opening in mice. This manner of transcranial cavitation detection in other species, for example monkeys, can be more difficult at least in part because the thickness and attenuation of a monkey skull can be as much as about 2.5 times higher than a murine skull. Thus, improved systems and techniques for opening of a tissue barrier in primates, including systems and techniques for performing in vivo transcranial and noninvasive cavitation detection are needed.

SUMMARY

Systems and methods for cavitation-guided opening of a tissue in a primate are disclosed herein.

In one embodiment of the disclosed subject matter, methods for cavitation-guided opening of a targeted region of tissue within a primate skull are provided. In an example embodiment, a method includes delivering one or more microbubbles to proximate the targeted region, applying an ultrasound beam, using a transducer, through the skull of the primate to the targeted region to open the tissue, transcranially acquiring acoustic emissions produced from an interaction between the one or more microbubbles and the tissue, and determining a cavitation spectrum from the acquired acoustic emissions.

In some embodiments, the method can be performed in vivo. The method can include determining the distance between the skull and the transducer based on the acoustic emissions, and the method can include determining a focal depth of the transducer based on the acoustic emissions.

In some embodiments, the method can include determining an obstruction of the opening of the tissue based on the cavitation spectrum, and determining the obstruction can include detecting a vessel between the ultrasound beam and the targeted region or proximate to the targeted region. The method can include adjusting the targeted region based on the obstruction, and in some embodiments, the adjusting can include adjusting the targeted region by avoiding the vessel or shielding by the vessel.

In some embodiments, the method can include determining the presence of inertial cavitation during opening, and/or adjusting one or more parameters to prevent the inertial cavitation. The one or more parameters can be a size of the one or more microbubbles and/or an acoustic pressure of the ultrasound beam. Adjusting the one or more parameters can include selecting the one or more microbubbles having a size within a range of between about 1 to 10 microns, or in some embodiments, between about 4 to 5 microns. Additionally or alternatively, adjusting the one or more parameters can include adjusting the acoustic pressure of the ultrasound to be within a range between about 0.10 to 0.45 MPa at the targeted region.

In another embodiment of the disclosed subject matter, systems for in vivo, cavitation-guided opening of a targeted region of tissue within a primate skull are provided. In an example embodiment, a system includes an introducer to deliver one or more microbubbles to proximate the targeted region Such a system also includes a transducer, coupled to the targeting assembly, to apply an ultrasound beam through the skull of the primate to the targeted region to open the tissue, a cavitation detector, adapted for coupling to the skull and for transcranial acquisition of acoustic emissions produced from an interaction between the one or more microbubbles and the tissue, and a processor, coupled to the cavitation detector, configured to determine a cavitation spectrum from the acquired acoustic emissions.

In some embodiments, the processor can be further configured to determine the distance between the skull and the transducer based on the acoustic emissions. Additionally or alternatively, the processor can be further configured to determine a focal depth of the transducer based on the acoustic emissions.

In some embodiments, the processor can be further configured to determine an obstruction of the opening of the tissue based on the cavitation spectrum. The obstruction can include a vessel between the ultrasound beam and the targeted region and/or proximate to the targeted region. The processor can be further configured to adjust the targeted region based on the obstruction. Additionally or alternatively, the processor can be further configured to adjust the targeted region based on the obstruction to avoid the vessel and/or shielding by the vessel.

In some embodiments, the processor can be further configured to determine the presence of inertial cavitation during opening, and adjust one or more parameters to prevent the inertial cavitation. The one or more parameters can be a size of the one or more microbubbles and/or an acoustic pressure of the ultrasound beam. The size of the one or more microbubbles can be adjusted to within a range of between about 1 to 10 microns, or in some embodiments, between about 4 to 5 microns. The acoustic pressure can be adjusted to within a range between about 0.10 to 0.45 MPa at the targeted region.

BRIEF DESCRIPTION OF THE DRAWINGS

The accompanying drawings, which are incorporated and constitute part of this disclosure, illustrate some embodiments of the disclosed subject matter.

FIGS. 7a-7j are images illustrating further features of the method of FIG. 4.

FIGS. 8a-8f are images illustrating further features of the method of FIG. 4.

FIGS. 17A-17D are images illustrating exemplary results for in vitro cavitation monitoring according to the disclosed subject matter.

FIGS. 22A-22D are diagrams illustrating exemplary in vivo BBB opening at 275 kPa, 350 kPa, 450 kPa and 600 kPa, respectively, according to the disclosed subject matter.

FIGS. 23A-23D are images illustrating exemplary safety assessments according to the disclosed subject matter.

Throughout the figures and specification the same reference numerals are used to indicate similar features and/or structures.

DETAILED DESCRIPTION

The systems and methods described herein are useful for in vivo transcranial, noninvasive cavitation detection and opening of a tissue with microbubbles and allow for real-time monitoring. Although the description provides as an example opening the blood-brain barrier (BBB), the systems and methods herein are useful for opening other tissues, such as muscular tissue, liver tissue or tumorous tissue, among others.

The subject matter disclosed herein include methods and systems for cavitation-guided opening of a tissue in a primate. Accordingly, the techniques described herein make use of transcranially-acquired acoustic emissions produced from an interaction between the one or more microbubbles and the tissue, and determine a cavitation spectrum from the acquired acoustic emissions. The cavitation spectrum can be used, for example, to determine an obstruction of the opening of the tissue, and/or to adjust targeting of the tissue to avoid the obstruction. Thus, the disclosed subject matter can be utilized to perform a cavitation-guided BBB opening to improve monitoring of the target of sonication.

Figure 1C:
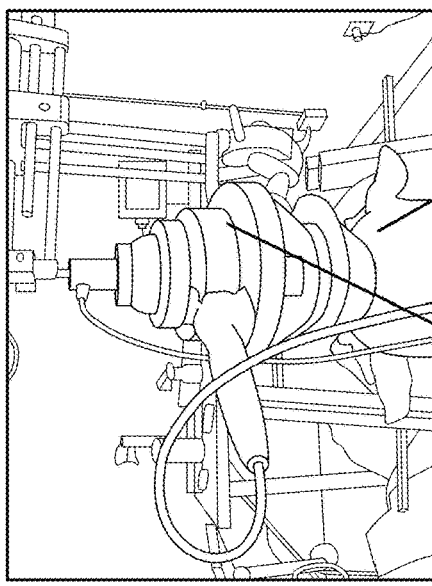
FIGS. 1a-1d are diagrams illustrating an exemplary system for cavitation-guided opening of a tissue in a primate in accordance with an exemplary embodiment of the disclosed subject matter.
Figure 1B:
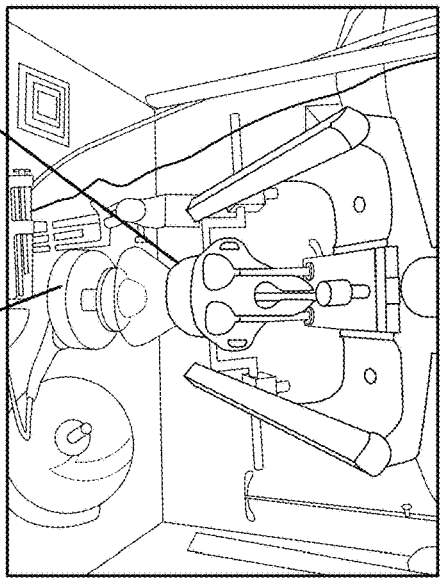
Figure 1A:
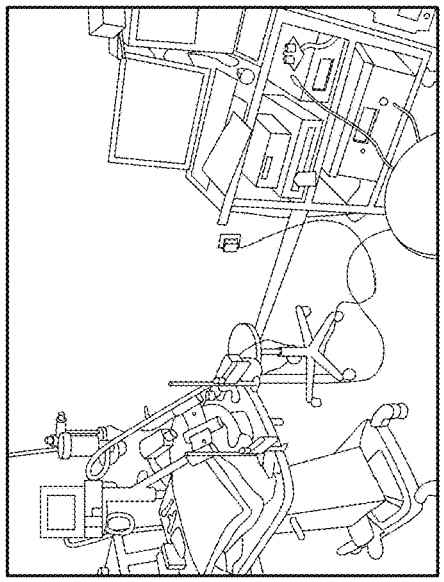
Figure 1D:
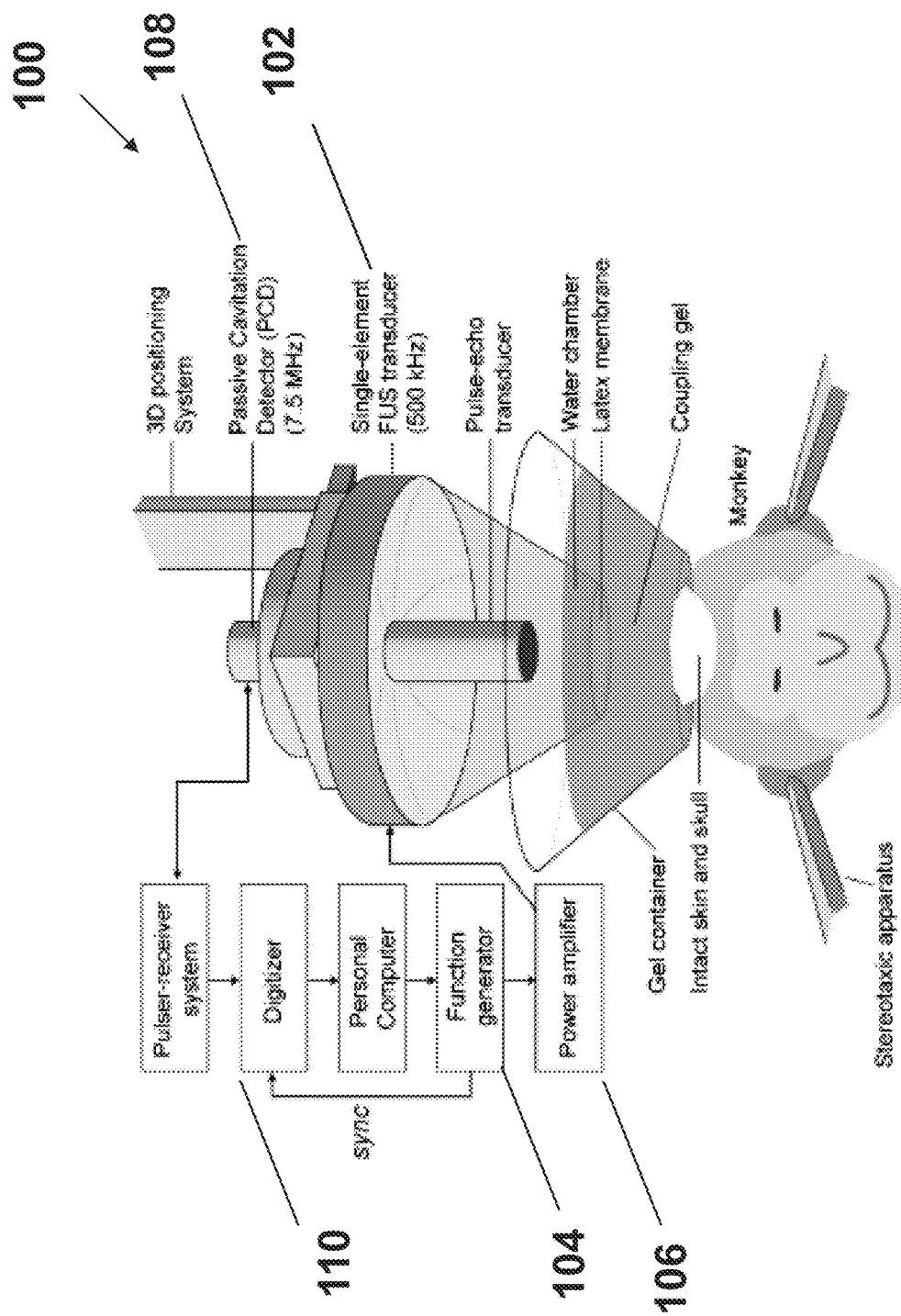

FIGS. 1a-1d show an exemplary system for in vivo FUS-induced BBB opening according to the disclosed subject matter. FIG. 1d illustrates an exemplary embodiment of a system 100 for in vivo cavitation-guided opening of a tissue in a primate according to the disclosed subject matter. A single-element, circular FUS transducer 102 which can have a hole in its center and be driven by a function generator 104 (for example, obtained from Agilent Technologies, Palo Alto, Calif., USA) through a 50 dB power amplifier 106 (for example, obtained from ENI Inc., Rochester, N.Y., USA). The FUS transducer 102 can be mounted on a standard monkey stereotaxic frame for improved positioning accuracy, as shown for example in FIGS. 2a-2c. As shown in FIG. 1d, the FUS transducer 102 can be further coupled to the scalp and/or skull of the primate using a coupling medium, which can be for example a coupling gel as used in standard ultrasound imaging. The center frequency, focal depth, outer radius and inner radius of the FUS transducer can be within a range of 200-900 kHz, 40-120 mm, 10-40 mm, and 5-12 mm, respectively, and in some embodiments can be 500 kHz, 90 mm, 30 mm, and 11.2 mm, respectively. A single-element PCD 108 (as embodied herein with a center frequency: 7.5 MHz, focal length: 60 mm, Olympus NDT, Waltham, Mass., USA) can be configured through the center hole of the FUS transducer 102. The FUS transducer 102 and the PCD 108 can be aligned so that their focal regions overlap within the confocal volume. The PCD 108 can be connected to a digitizer 110 (for example, obtained from Gage Applied Technologies, Inc., Lachine, QC, Canada) through a 20 dB preamplifier (for example, model no. 5800 obtained from Olympus NDT, Waltham, Mass., USA), and can be used to passively acquire acoustic emissions from microbubbles.

Figure 2C:
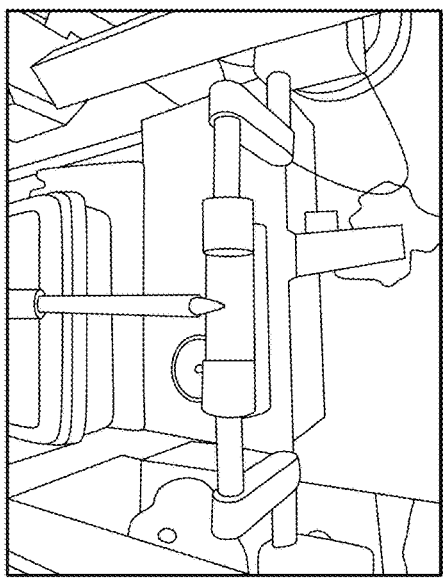
FIGS. 2a-2c are diagrams illustrating an exemplary targeting method for use with a method for cavitation-guided opening of a tissue in a primate in accordance with an exemplary embodiment of the disclosed subject matter.
Figure 2B:
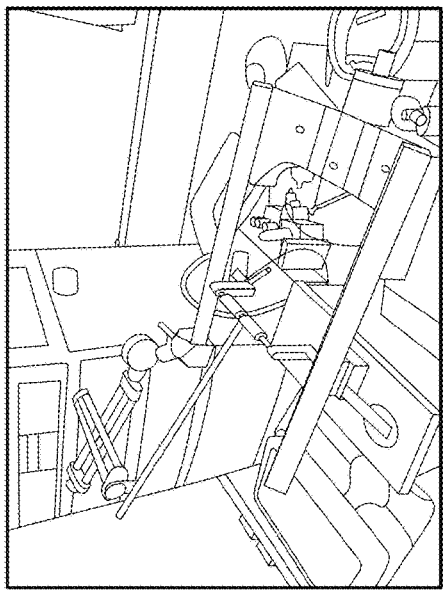
Figure 2A:
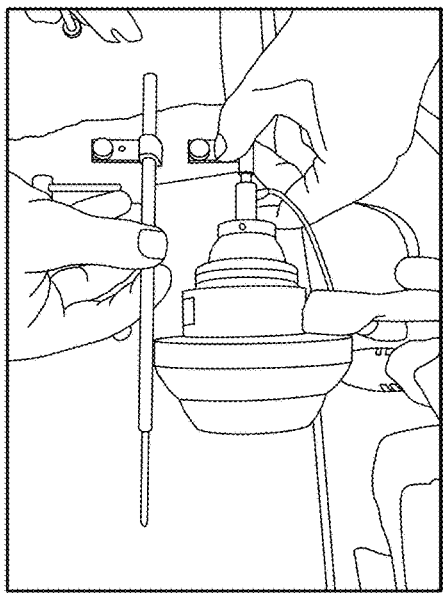

FIGS. 2a-2c illustrate an exemplary targeting system for in vivo FUS-induced BBB opening according to the disclosed subject matter. As shown in FIG. 2a, a positioning rod indicating the position of the focus (for example, 5 cm away from the edge of the transducer) can be used to target. In FIG. 2b, the positioning rod can be mounted on the manipulator to locate the origin of the stereotactic coordinates. In FIG. 2c, the origin of the stereotactic coordinates, which can be indicated by an engraved cross on a metal piece between ear-bars, can be targeted with the tip of the positioning rod.

Figure 3:
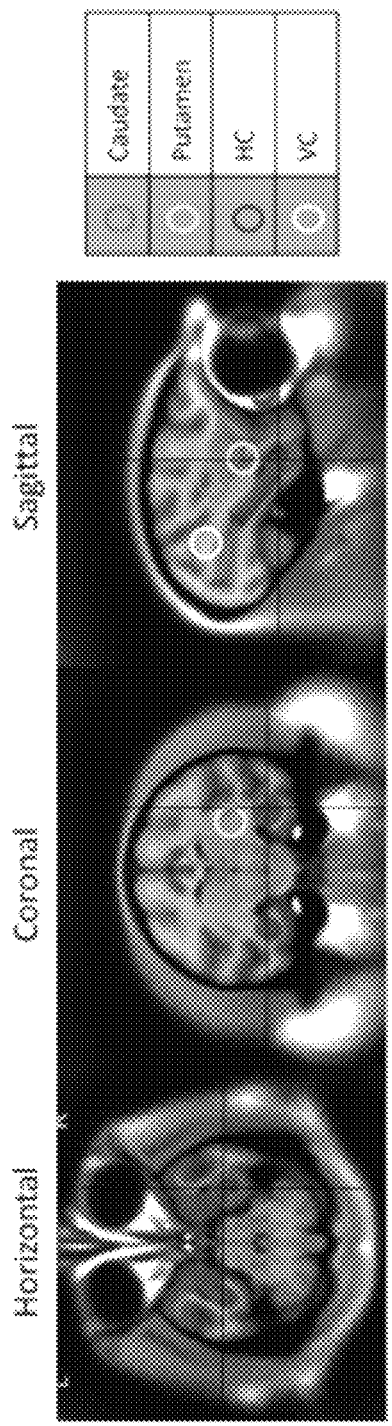
FIG. 3 are images illustrating targeting regions in a brain for cavitation-guided opening of a tissue in a primate in accordance with an exemplary embodiment of the disclosed subject matter.

An exemplary method according to the disclosed subject matter was performed on five male rhesus macaques over the course of 12 sessions (a total of 25 sonications), with two different protocols (A and B) implemented as shown in Table 1 and described further below. The acoustic parameters of each protocol, such as the pulse length (PL), pulse repetition frequency (PRF), microbubbles used, and peak rarefractional pressure (PRP) are provided. A corresponding targeting region and number (#) denotes the number of sonications performed in a region, such as the Visual Cortex (VC), Hippocampus (HC), Caudate (Ca), and Putamen (Pu). N denotes the number of monkeys. The corresponding targeting regions are illustrated in FIG. 3, in horizontal, coronal and sagittal views of the brain.

As embodied herein and shown in Table 1, in some protocols, 4-5 μm microbubbles were utilized, which were manufactured in-house and size-isolated using differential centrifugation. In some protocols, polydispersed Definity® microbubbles (from Lantheus Medical Imaging, MA, USA) were utilized. Sonication was performed after intravenous (IV) injection of 500 μL microbubbles for all monkeys.

TABLE 1

| Protocol | PL | PRF (Hz) | microbubble | PNP (MPa) | Targeting (#) | N |
|---|---|---|---|---|---|---|
| A | 100 cycles | 10 | Definity ® | 0.20 | VC (1) | 1 |
|   |   |   |   | 0.25 | VC (1) | 1 |
|   |   |   |   | 0.30 | VC (1) | 1 |
| B | 5000 cycles | 2 | Definity ® | 0.30 | HC (3) | 2 |
|   |   |   |   | 0.45 | HC (3) | 2 |
|   |   |   |   | 0.60 | HC (1) | 1 |
|   |   |   | 4-5 μm | 0.30 | VC (2), Ca (2), Pu (1) | 4 |
|   |   |   |   | 0.45 | VC (4), Ca (1), HC (1) | 4 |
|   |   |   |   | 0.30 | VC (2), HC (2) | 1 |

Figure 4:
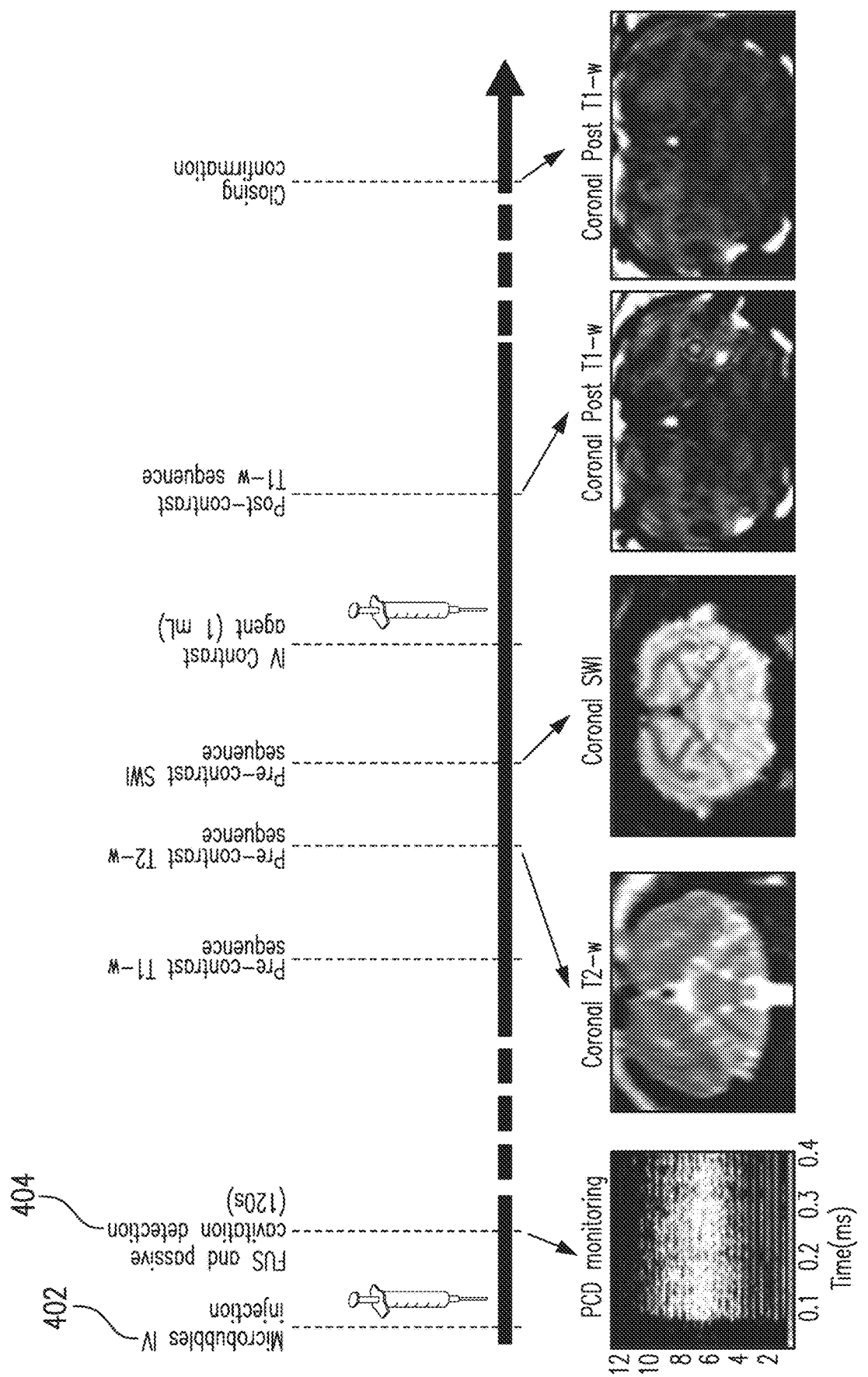
FIG. 4 is a diagram illustrating an exemplary method for cavitation-guided opening of a tissue in a primate in accordance with an exemplary embodiment of the disclosed subject matter.

An exemplary method according to the disclosed subject matter is illustrated in FIG. 4. Two exemplary targets at 0.30 MPa (indicated with the dark circle) and 0.45 MPa (indicated with the light circle) are also illustrated. As described above, at 402, microbubbles can be intravenously injected into the monkey. At 404, FUS and passive cavitation detection are performed. As embodied herein, for application of the FUS, all animals were anesthetized with 2% isoflurane (carrier gas: oxygen). The heart rate was held at approximately 120 beats per minute and the respiratory rate at around 60 breaths per minute. Prior to sonication, the scalp hair was removed with a depilatory cream to improve acoustic transmission. The animal's head was then placed in a stereotactic frame to facilitate targeting of the ultrasound. The sonication was performed after intravenous (IV) injection of a 500-μL microbubble bolus in all experiments ($5 \times 10^9$ numbers/mL for customized microbubbles and $1.2 \times 10^{10}$ numbers/mL for Definity®). Targeting was further improved using a manipulator and a positioning rod indicating the position of the focus relative to the stereotaxic coordinates (as shown in FIG. 2).

Magnetic resonance imaging (MRI) at 3.0 T (Philips Medical Systems, Andover, Mass., USA) was used to confirm and quantify the BBB opening following the opening. Three-dimensional (3D) spoiled gradient T1-weighted sequences (TR/TE=20/1.4 ms; flip angle: 30°; NEX=2; spatial resolution: 500×500 μm; slice thickness: 1 mm with no interslice gap) were applied after intravenous (IV) injection of gadodiamide (from Omniscan®, GE Healthcare, Princeton, N.J., USA) about 1 hour after sonication. Gadodiamide presence in the brain parenchyma was induced by the BBB opening. 3D T2-weighted sequence (TR/TE=3000/80; flip angle: 90°; NEX=3; spatial resolution: 400×400 $\mu m^2$; slice thickness: 2 mm with no interslice gap) and 3D Susceptibility-Weighted Image (SWI) sequence were applied (TR/TE=19/27 ms; flip angle: 15°; NEX=1; spatial resolution: 400×400 $\mu m^2$; slice thickness: 1 mm with no interslice gap) and were used to assess brain damage. In the session of closing timeline and accuracy, FSL, a library of analysis tools for MRI brain imaging data, was used to perform the image registration to keep the brain orientation at the same location for the closing timeline determination, and the focal shift identification.

Figure 5C:
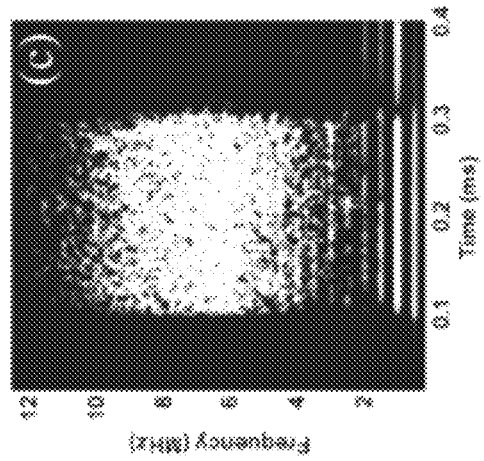
FIGS. 5a-5f are images illustrating further features of the method of FIG. 4.
Figure 5B:
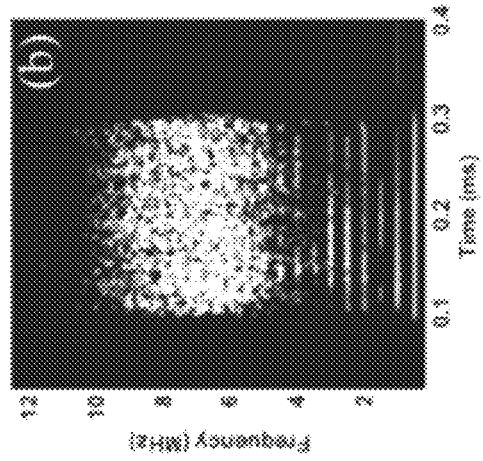
Figure 5A:
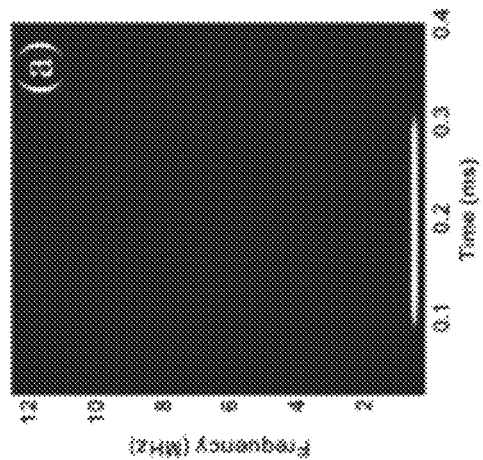
Figure 5F:
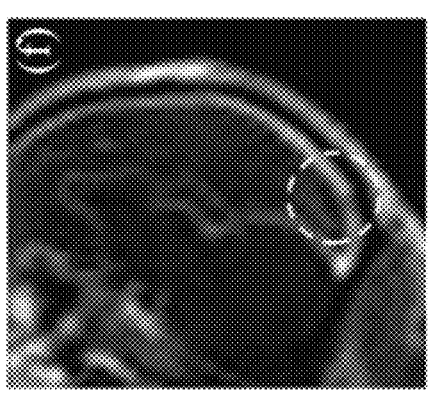
Figure 5E:
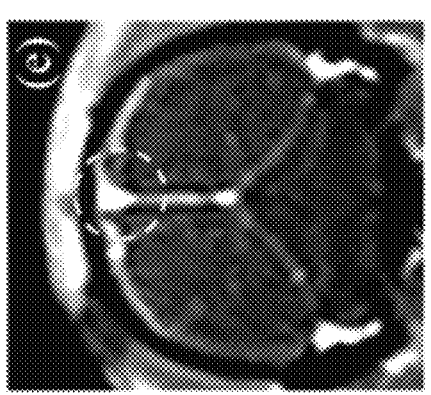
Figure 5D:
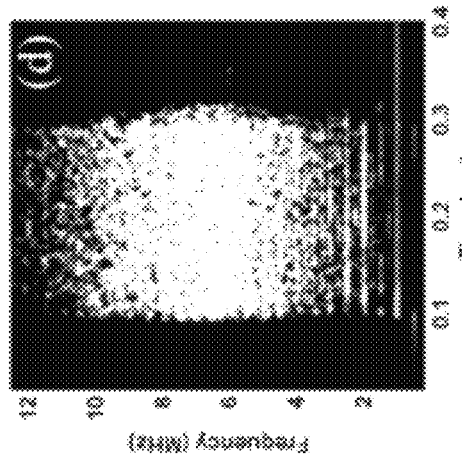

As discussed above, two exemplary protocols were implemented herein. In protocol A in Table 1, Definity® microbubbles were utilized with relatively short PL (for example, 100 cycles) at 0.20-0.30 MPa. The results are illustrated in FIGS. 5a-5f. FIG. 5a shows a spectrogram without microbubble administration as a baseline. Spectrograms during FUS sonication of a monkey at 0.20 MPa (FIG. 5b), 0.25 MPa (FIG. 5c) and 0.30 MPa (FIG. 5d), and magnetic resonance (MR) images with coronal (FIG. 5e) and sagittal planes (FIG. 5f) are also shown. FIGS. 5a-5f illustrate that no BBB opening was induced with protocol A, for example in the region indicated with the dashed circle, although inertial cavitation, i.e., broadband response, was shown in each case. Thus, microbubble response was detected through the monkey skull.

Figure 6A:
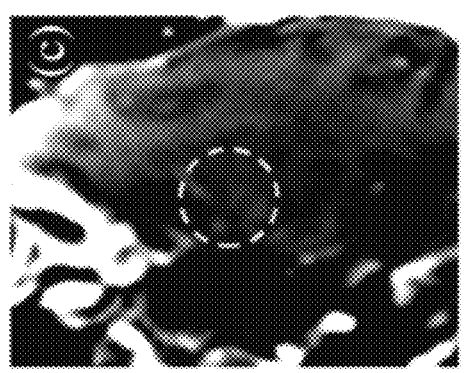
FIGS. 6a-6c are images illustrating further features of the method of FIG. 4.
Figure 6B:
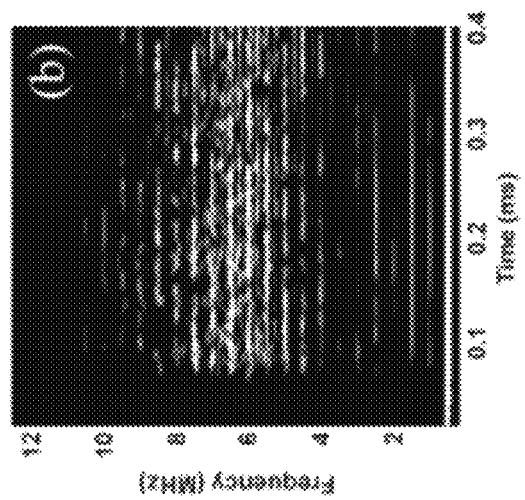
Figure 6C:
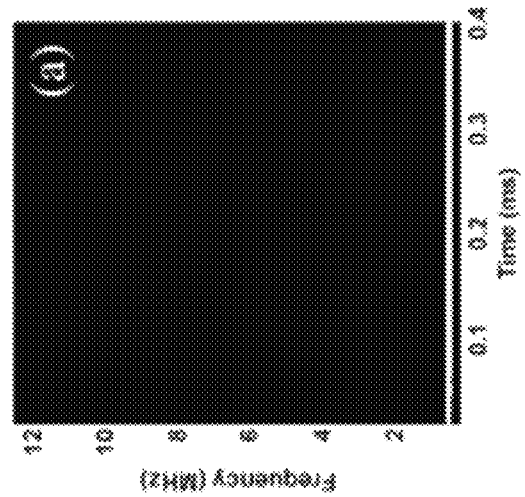

In protocol B in Table 1, relatively long PL (for example, 5000 cycles) and higher pressure (0.30-0.60 MPa) were applied with Definity® or 4-5-μm diameter bubbles. FIG. 6a shows a spectrogram without microbubble administration as a baseline. FIG. 6b shows a spectrogram during FUS sonication of a monkey at 0.45 MPa and indicates a broadband response. FIG. 6c shows an MR image of the sagittal plane, and indicates that no BBB opening was induced, for example in the region of the dashed circle. Thus, as shown in FIG. 6, no BBB opening was induced at 0.45 MPa using Definity®, but a broadband response was detected.

Figures 7A, 7B, 7C:
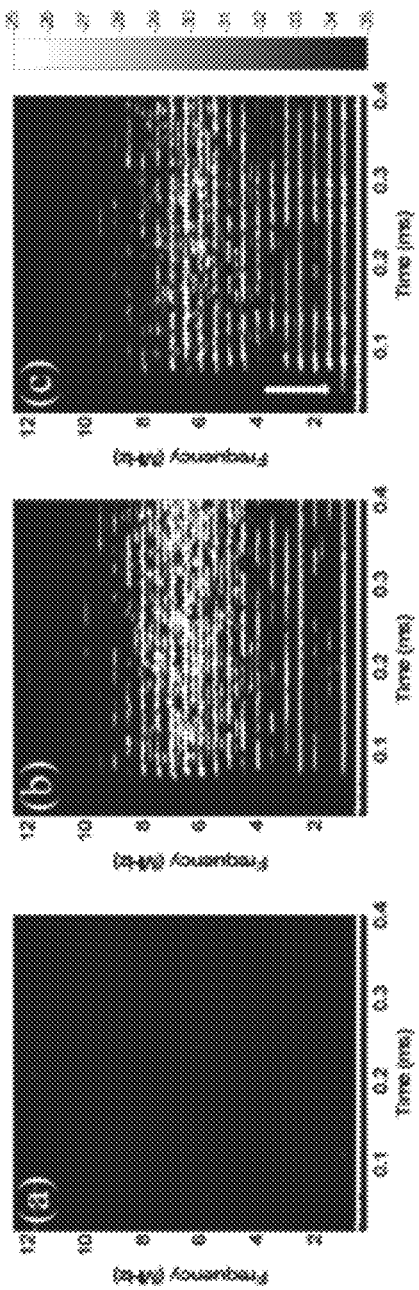
Figures 7F, 7H:
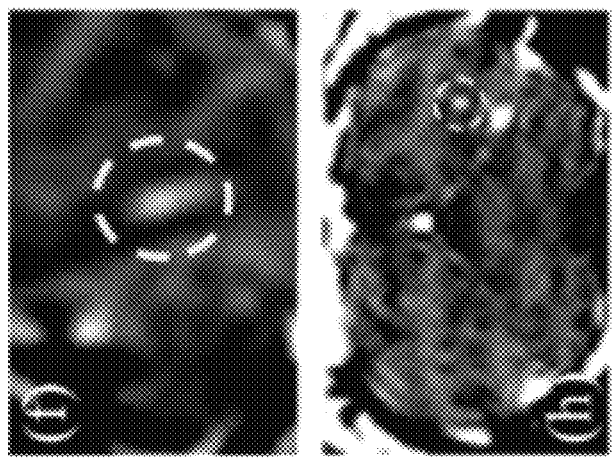
Figures 7E, 7G:
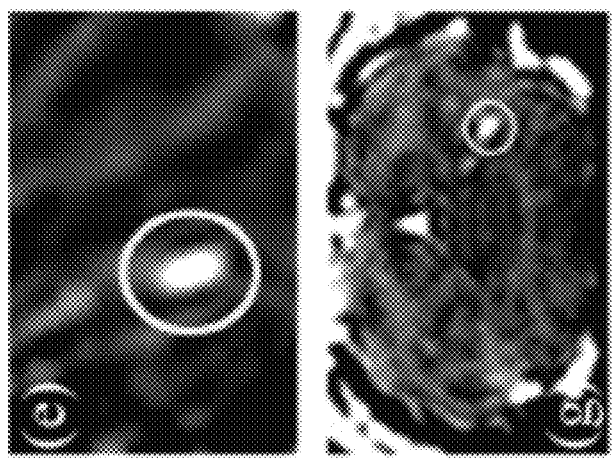
Figure 7D:
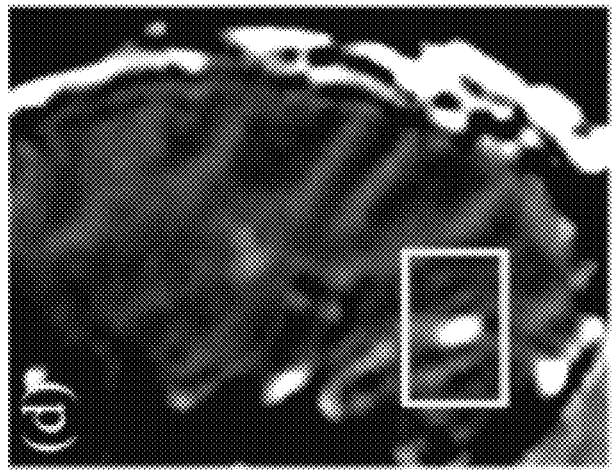

In protocol B using the 4-5-μm microbubbles, however, the BBB was opened at 0.30 and 0.45 MPa. FIG. 7a is the baseline image showing no higher harmonics or broadband response present. The spectrogram corresponding to the first pulse with microbubbles administered shows that broadband acoustic emissions, i.e., inertial cavitation, are detected at 0.30 MPa (FIG. 7b) and 0.45 MPa (FIG. 7c). The white arrow in FIG. 7c indicates that the time-point of occurrence of the second harmonic coincides with the travel distance to the skull. Therefore, harmonics higher than the 3rd harmonic and any broadband response in FIGS. 7b and 7c can be considered to be due to microbubble effects. MR images in FIGS. 7d-7h confirm opening of the BBB. Deposition of the MRI contrast agent in the brain tissue after ultrasound exposure detected in the MR images indicate that the BBB was opened at 0.30 MPa (shown in FIGS. 7d, 7e, and 7g) and 0.45 MPa (shown in FIGS. 7f and 7h) using the 4-5-μm bubbles. At least the white matter can be observed to be opened in FIGS. 7d-7h in the circled region. The peak MR intensity enhancement at the BBB-opened region relative to the average value in the parenchyma was increased by 119% and 48% at 0.3 MPa and 0.45 MPa, respectively. The volume of the BBB disruption was 24.6 mm$^3$ and 30.5 mm$^3$, respectively. The two distinct opened sites were separated by a distance of 4.74 mm.

The spectrograms obtained during treatment can also provide targeting guidance. The different time of flight for each harmonic can allow the depth at which different phenomena occurs to be determined. For example, FIG. 7i shows the spectrogram of FIG. 7c, providing the depth corresponding to the time of flight for each harmonic. In FIG. 7i, bubble activity at the focus and non-linear effects induced by the skull (as indicated by the white arrow) can be distinguished. As such, bubble activity can be measured to occur about 4.5 cm below the skull, which is in agreement with the initial MR-atlas planning.

The skull can be used as a reference point to quantify the depth of the transducer focus. Due to the amount of pressure applied during treatment, certain non-linear effects induced by the bone interface are not necessarily detected during sonication. To avoid this, the pressure can be increased during the control acquisition until the appearance of the second harmonic (as shown in FIG. 7j). The pressure can be safely increased because, at this point of the procedure, bubbles generally are not present in the system. Thus, based on the acoustic emissions shown in FIG. 7j, the skull depth can be determined, and the result can be displayed, for example on a real-time PCD monitoring, to provide treatment guidance.

Figure 9:
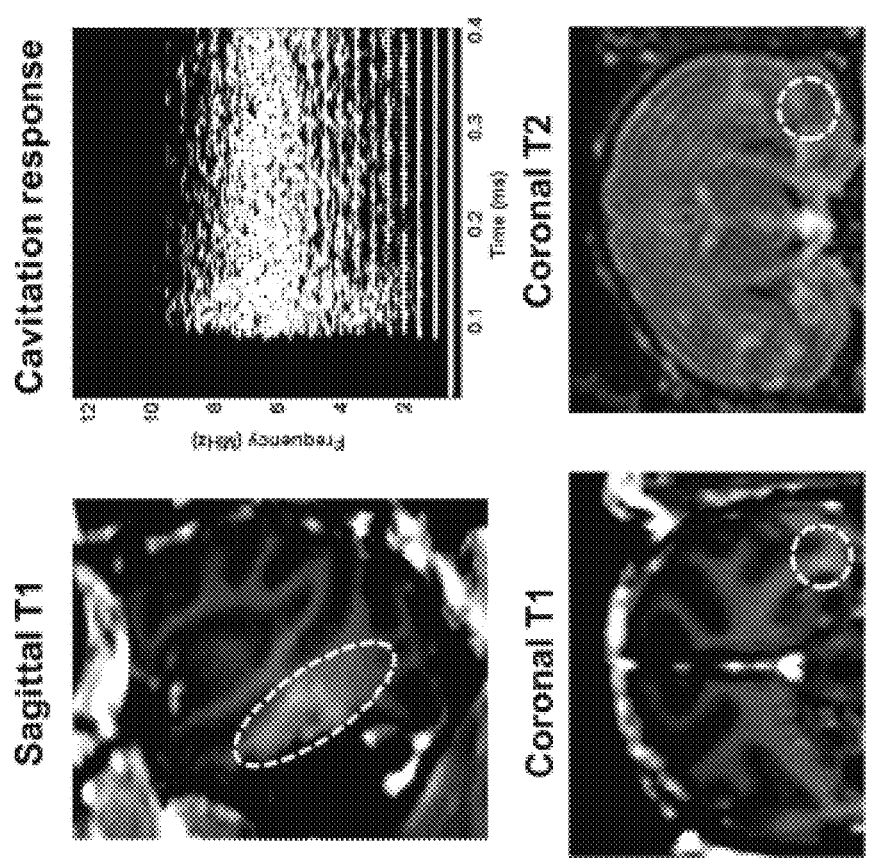
FIG. 9 includes images illustrating further features of the method of FIG. 4.
Figure 10:
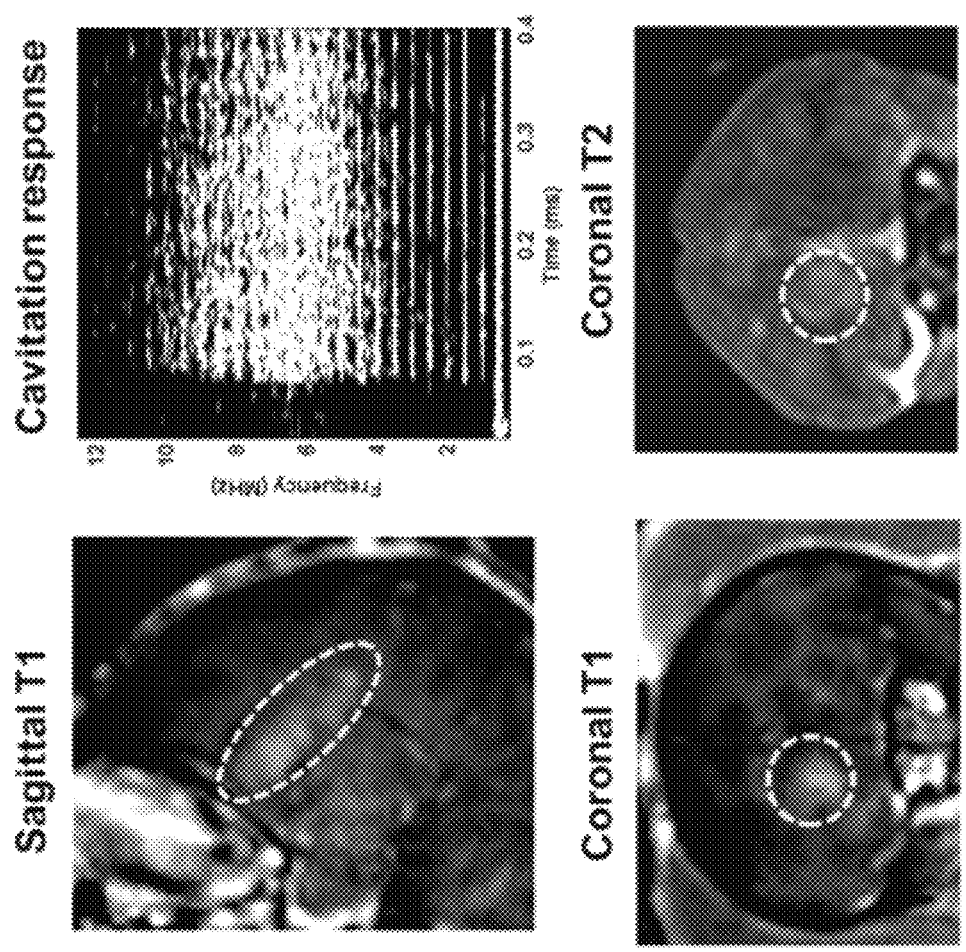
FIG. 10 includes images illustrating further features of the method of FIG. 4.

The MRI sequence described above and an IV contrast agent injection were repeated six days after BBB opening. No intensity enhancement was observed indicating that the BBB was closed or reinstated. T2-weighted and susceptibility-weighted MRI sequences were used to assess potential brain damage after ME-FUS. FIGS. 8a, 8c and 8d show the 3D T2-weighted sequence. FIGS. 8b, 8e and 8f show susceptibility-weighted image (SWI) sequence. The sonicated regions are highlighted in dashed circles. No edemas or hemorrhages can be seen in the sonicated regions. The same protocol described above was repeated for the two following sessions applying 0.6 MPa and two different kinds of microbubbles. The results are shown in FIGS. 9 and 10. FIG. 9 shows images from sonication performed using the Definity® microbubbles and applying 0.6 MPa to the targeted region (indicated by the dashed circles). The 3D Spoiled Gradient-Echo (SPGR) T1-weighted sequence was applied after intravenous injection of gadodiamide about 1 hour after sonication. No damage is shown in the T2-weighted sequence. FIG. 10 shows images from sonication performed using the customized microbubbles and applying 0.6 MPa to the targeted region (indicated by the dashed circles). The 3D SPGR T1-weighted sequence was applied after intravenous injection of gadodiamide about 1 hour after sonication. An edema is indicated in the T2-weighted sequence.

The T1-weighted MR sequences were used to track the diffusion of gadodiamide. The peak MR intensity enhancement at the BBB-opened region relative to the average value in the parenchyma was increased by 68% and 41% using the customized and Definity® microbubbles, respectively. The volume of the BBB disruption was equal to 285.5 mm$^3$ and 116.3 mm$^3$, respectively. The BBB opening regions at the caudate and the hippocampus were shifted from the targeted location by respectively 0.6 mm and 0.9 mm laterally and 6.5 mm and 7.2 mm axially. T2-weighted MR sequences were also used to assess potential damage in the brain. An edematous region was detected on the T2-weighted MRI in one case using the custom-made microbubbles while no damage was detected using Definity® with the same acoustic parameters. A subsequent qualitative assessment of basic animal behavior has been performed. Normal cognitive behavior has been noted following ME-FUS procedures at moderate pressures and using Definity®. In the case of the 0.6 MPa application of the customized microbubbles, the animal showing the edema exhibited a weakness in the contra-lateral arm over four days after treatment, but then showed a recovery after the four days. The corresponding spectrogram showed that a large broadband signal was recorded for both the customized and Definity® microbubbles.

Figure 11:
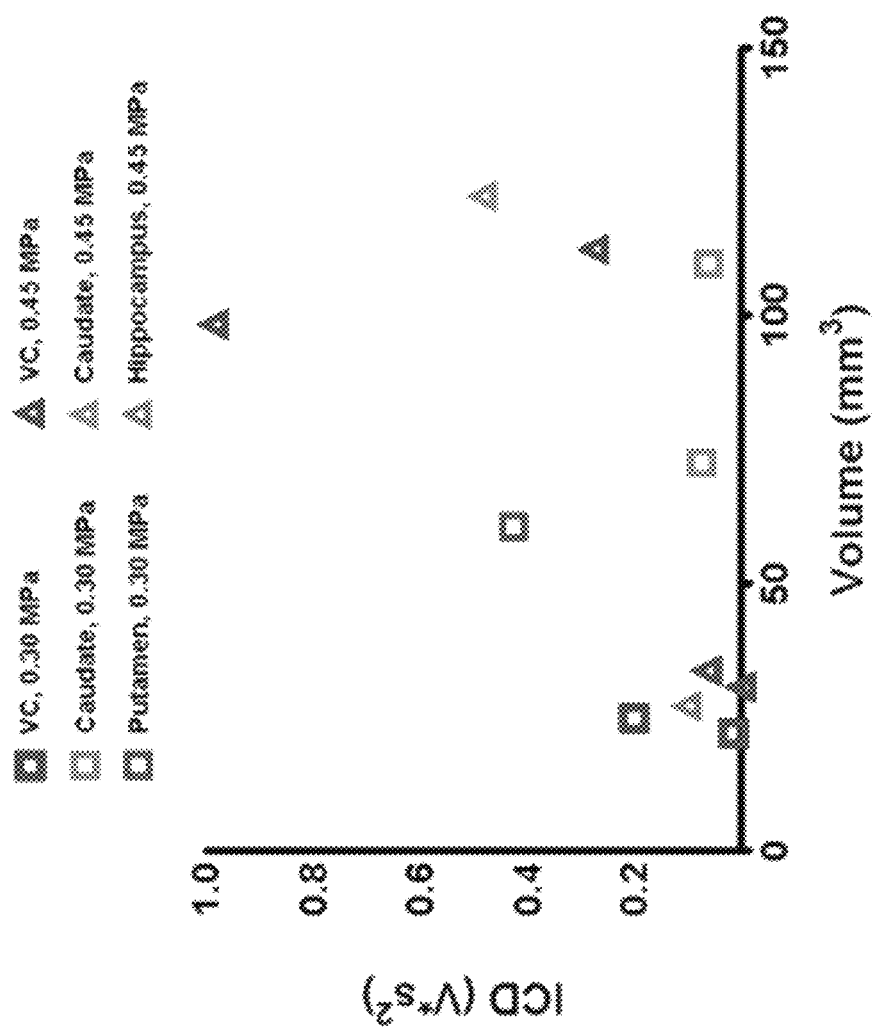
FIG. 11 is a graph illustrating further features of the method of FIG. 4.
Figure 12:
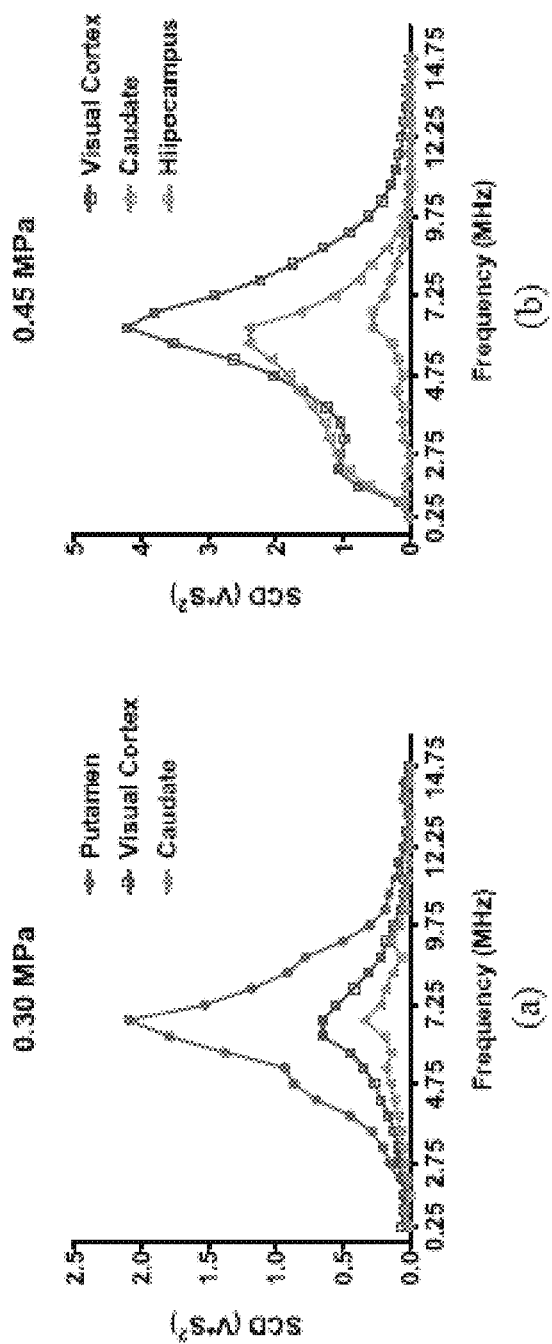
FIG. 12 is a graph illustrating further features of the method of FIG. 4.

As shown in Table 1, a total of 11 BBB openings were induced at 0.30 and 0.45 MPa using 4-5-µm diameter bubbles. A correlation between the inertial cavitation dose (ICD) and the BBB opening volume is shown in FIG. 11. At 0.60 MPa, because the BBB opening volume was due to the combination of four sonications (two in the visual cortex and two in the hippocampus), this opening volume (285.5 mm3) is not included in FIG. 11. The stable cavitation dose (SCD) at all ultra-harmonics of difference regions at 0.30 and 0.45 MPa is shown in FIG. 12. At 0.30 MPa, the amplitude at ultra-harmonics was the largest in the putamen and the lowest in the visual cortex. At 0.45 MPa, the amplitude in the visual cortex was higher than in the caudate and the hippocampus.

Figure 13:
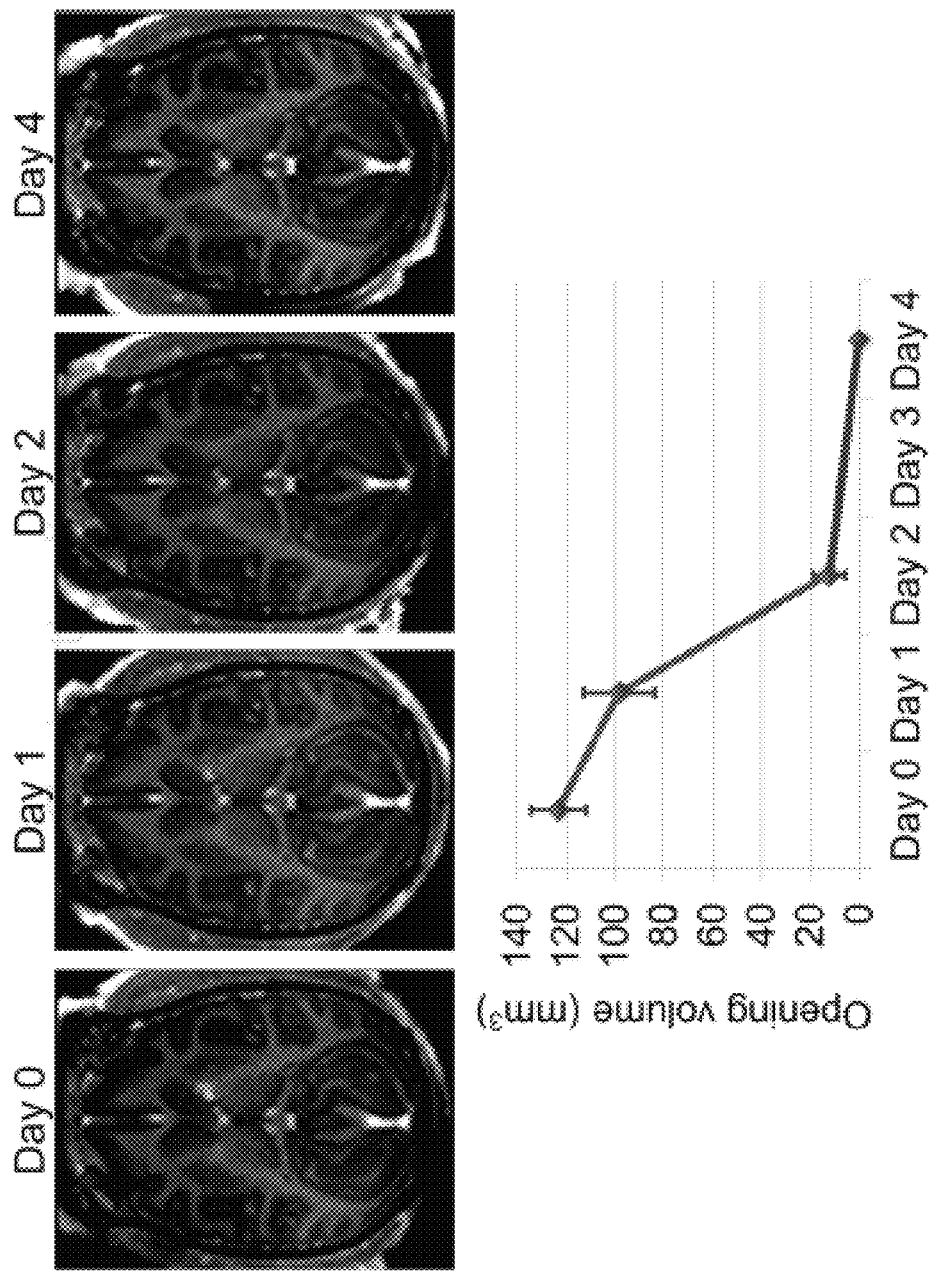
FIG. 13 includes images illustrating further features of the method of FIG. 4.

The duration of BBB opening and the corresponding opening volume of each scan are illustrated in FIG. 13. BBB opening was performed in a monkey caudate using 0.30 MPa and 4-5 µm microbubbles. The highlighted region in the images illustrates the opening region, which is no longer visible in day 4. The corresponding quantification of BBB opening volume in the graph indicates that the BBB is nearly closed on day 2. The error bar illustrates the standard deviation of the MR intensity of the BBB opening area. Thus, at 0.30 MPa, the BBB was opened in the caudate, and the opening was reinstated after two days. On day 4, the opened BBB was completely recovered. The targeting precision was also investigated. An axial shift of the focus was found to be about 3.4 mm for the Caudate region and about 6.9 mm for the Visual Cortex region. The corresponding spectrograms over the 2 min duration are also shown. The focal shift, BBB opening volume, and MRI contrast enhancement of the visual cortex and caudate are quantified in Table 2.

TABLE 2

| Region | Caudate | Visual cortex |
| --- | --- | --- |
| Pressure (MPa) | 0.30 | 0.45 |
| Axial focal shift (mm) | 3.4 | 6.9 |
| Volume (mm$^3$) | 72.5 | 112.3 |
| MR Enhancement | 52% | 63% |

Accordingly, FUS-induced BBB opening, along with transcranial cavitation detection, in non-human primates is provided according to an embodiment of the disclosed subject matter. As discussed above with respect to Table 1, sonication in four locations were performed in five animals according to the embodiments discussed herein. Pressures ranging from 0.3 MPa to 0.6 MPa were utilized. Increased pressure can result in a larger BBB opening extent and higher BBB permeability, while a "safety window" can be considered to be within the pressure range of 0.30 MPa and 0.60 MPa. In the exemplary embodiments, T1-weighted MRI at 3.0 T was used to confirm the results of the disclosed subject matter, confirming BBB disruption by tracking the diffusion of IV-injected gadodiamide in the brain. The cavitation response can be used to estimate the BBB opening volume and predict the occurrence of BBB opening.

To illustrate the effectiveness and determine further applications of the disclosed subject matter, the results of BBB opening in primates according to the disclosed subject matter can be compared to known methods for opening the BBB in other animals, such as mice. In the embodiments herein, except for the case of sonication performed at 0.60 MPa, no BBB opening was induced using Definity® microbubbles and 10-ms pulse length, despite the occurrence of inertial cavitation (as shown and described with respect to FIGS. 5 and 6). Accordingly, relatively lower pressures (for example, 0.20-0.30 MPa) and shorter pulse length (for example, 0.2 ms) utilized in protocol A can be ineffective to induce BBB opening. However, using techniques for BBB opening in mice, the BBB was opened at 0.45 MPa and PLs of 0.1, 0.2, 1, 2, and 10 ms, using comparable microbubbles. Thus, relatively higher pressures (for example, 0.30-0.60 MPa) can be necessary to open the BBB in monkeys using Definity®.

Further, the medial areas were targeted as shown in FIG. 5, and thus the focus included the superior sagittal sinus that, due to the relatively large volume of microbubbles circulating, resulted in larger amplitude of the cavitation spectrum. Measuring the cavitation spectrum can, therefore, be utilized to determine whether a large vessel is in the path of the FUS beam, and thus predict or avoid its effects on inducing BBB opening. The exact location of the focus in the brain can be difficult to predict, and further, the exact location of large vessels in the brain relative to the beam is generally not known in advance. Hence, the relationship between the amplitude of the cavitation spectrum, the area of BBB opening, and the BBB opening threshold can provide useful additional information regarding the presence of large vessels close to the focus. This information can thus be used to predict whether opening of the BBB is obstructed due to the focal spot proximity to a large vessel resulting in subsequent shielding and/or adjust the targeting accordingly to achieve BBB opening, i.e., by avoiding shielding by large vessels.

The results according to the disclosed subject matter can also be utilized to determine the dependence of the BBB opening on the microbubble types. In protocol B, at 0.30 and 0.45 MPa, BBB opening was only observed with the 4-5 m bubbles, as illustrated in FIGS. 7 and 8. At 0.60 MPa, a larger BBB opening area was obtained with the 4-5 µm bubbles, as illustrated in FIGS. 9 and 10. This can be due, at least in part, to a larger portion of the brain reaching the disruption threshold when peak pressure increases. The 4-5 µm bubbles can result in a larger BBB opening region in mice. Thus, the results disclosed herein are in qualitative agreement that the bubble size can affect the BBB opening in primates according to the disclosed subject matter.

The BBB can be opened at 0.3 MPa and inertial cavitation can occur at 0.45 MPa using 1.5-MHz FUS and 4-5 µm diameter bubbles. In the embodiments described herein, the BBB was also opened at 0.30, 0.45, and 0.60 MPa with the presence of inertial cavitation. The mechanical index was 0.25, 0.37, and 0.49 at 1.5 MHz, as well as 0.42, 0.64 and 1.02 at 500 kHz for 0.3 MPa, 0.45 MPa and 0.6 MPa, respectively. The MI threshold of the broadband response was about 0.451 and the broadband response was observed in most cases of BBB opening, and thus lower pressures can be applied and the stable cavitation dose can be quantified to determine whether the BBB can be opened with stable cavitation, and without inertial cavitation, using 4-5-µm diameter bubbles, and thus avoid the potential for damage to the subject that can be caused by inertial cavitation.

The cavitation response can be utilized to estimate the BBB opening volume. Statistical analysis of cavitation responses during BBB opening in mice indicates that the ICDs and BBB opening volume can be both pressure and bubble-size dependent. Regression analysis shows a linear correlation can occur between the ICD and the BBB opening volume at various bubble diameters. Thus, by analyzing the 11 openings performed with the 4-5-µm bubbles as embodied herein, volume prediction using the ICD can be performed, for example as illustrated in FIG. 11. In one embodiment of the disclosed subject matter, BBB opening can be performed and the corresponding opening volume can be predicted using the PCD system without the use of MRI for monitoring BBB opening during sonication. In this manner, FUS according to the disclosed subject matter can be applied while further reducing costs and improving real-time capability in clinical applications.

Figures 14A, 14B, 14C:
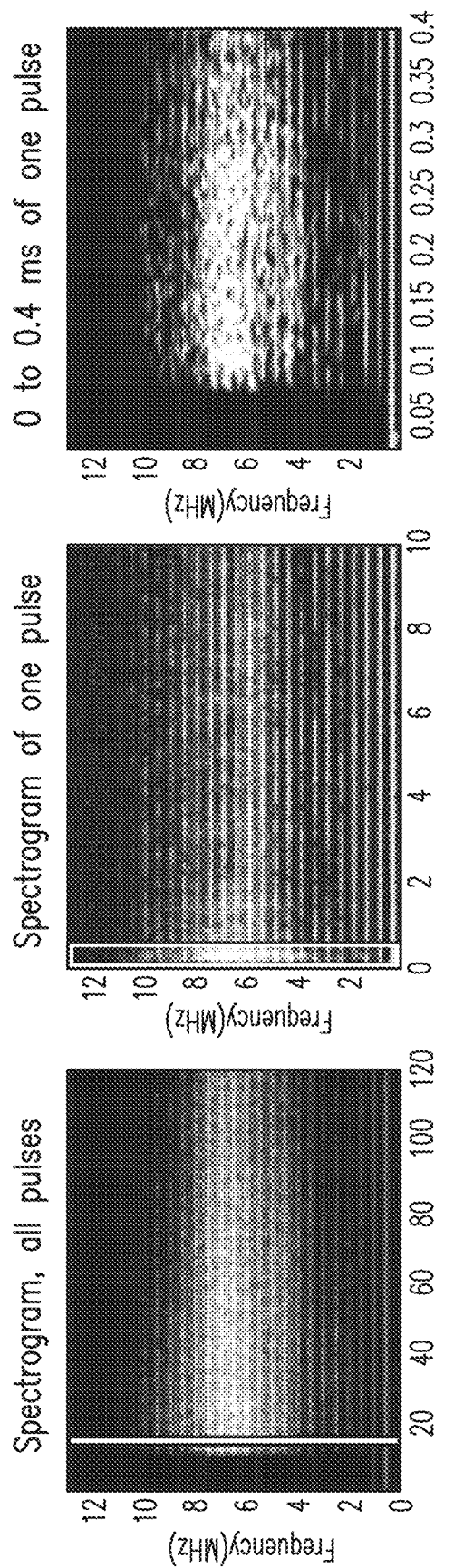
FIGS. 14a-14c are images illustrating further features of the method of FIG. 4.

From the cavitation response, in addition to the ICD, the spectrogram can be used to analyze microbubble behavior in real-time. In FIG. 14a, a spectrogram of total duration (i.e., 120 seconds or 2 minutes) indicate the duration for microbubbles to reach the brain after the IV-injection. For example, FIG. 14a shows a duration of 10 seconds for Definity® microbubbles to reach the brain. Thus, the spectrogram of total duration can be used, for example in a clinical application, to identify if a patient has a circulation problem affecting the movement of the microbubbles. The persistence of the microbubbles can also be identified.

In FIG. 14b, the spectrogram of one pulse (identified with the vertical line in FIG. 14a), shows a pulse length of 10 ms, and can be utilized to determine the duration of inertial cavitation. The duration can be microbubble dependent and correlated to the ICD. If insufficient microbubbles are sonicated at each pulse, the duration of inertial cavitation can be shorter such that lower ICD and BBB opening volume are induced.

In FIG. 14c, the first few hundred microseconds of one pulse (identified with the box in FIG. 14b), are shown and can indicate the location of the focus based on the starting point of harmonics and broadband response. This spectrogram can be utilized to estimate the actual focus, and thus determine the axial shift between the actual focus and the desired targeting region.

Since the primate brain is generally inhomogeneous, the BBB opening properties can be distinct among different areas of the brain. As shown for example in FIG. 7, the intensities of MRI contrast enhancement in the BBB opening region at 0.30 MPa was 2.3 times higher than at 0.45 MPa. These differences can be due, at least in part, to a higher concentration of microbubbles in the sonicated region during the 0.30 MPa stimulation such than MRI contrast is enhanced and the broadband response is stronger.

Likewise, the cavitation response can also be region dependent. As discussed above, the SCD at distinct regions at 0.30 and 0.45 MPa is shown in FIG. 11. The relatively higher sensitivity is shown near the center frequency of the PCD (i.e., at about 7.5 MHz). Four different locations were shown, each having a distinct cavitation response. For example, as shown in FIG. 11, at 0.30 MPa, the amplitude level is largest in the putamen and smallest in the visual cortex. Further, comparing the caudate shown in FIG. 12 and the visual cortex shown in FIG. 13, the visual cortex is deeper than the caudate such that lower amplitudes are detected in the visual cortex. A comparison between the caudate and putamen can be made from FIG. 3. As shown, the putamen is deeper than caudate in the sagittal view, but is roughly the same depth in the coronal view. Further sonications can be performed in the putamen to determine the region dependent cavitation response. A further comparison between the visual cortex and hippocampus can be made from FIG. 3. As shown, the hippocampus is deeper than visual cortex from the sagittal and coronal view such that the amplitude detected was lower in the hippocampus. Although the depth of the targeting regions can affect the PCD amplitude, the region dependent cavitation can further characterize the BBB opening properties in different locations in primates.

Accordingly, noninvasive and transcranial cavitation detection during BBB opening in nonhuman primates are provided herein. Further, the MRI contrast enhancement and cavitation response can be considered to be region and/or microbubble-size dependent. Inertial cavitation can fail to induce BBB opening, for example when the focus overlaps with large vessels such as the superior sagittal sinus, and thus the systems and methods according to the disclosed subject matter can be utilized to perform a cavitation-guided BBB opening to improve monitoring of the target of sonication.

According to another aspect of the disclosed subject matter, FUS-induced BBB opening can be performed in vitro in macaque and human primate skulls. Furthermore, skull effects and real-time monitoring of FUS-induced BBB opening of primate skulls can be performed in vivo.

At least three types of cavitation doses and cavitation SNR can be quantified and used to address the characteristics of cavitation, skull attenuation, and detection limit. The stable cavitation dose (SCD) representing the overall extent of stable cavitation can be represented as the cumulative harmonic or ultraharmonic emission. The inertial cavitation dose (ICD) can represent the overall extent of inertial cavitation, and can be represented as the cumulative broadband acoustic emission. The cavitation SNR can be represented as the ratio of post- to pre-microbubble administration cavitation doses.

Figure 15:
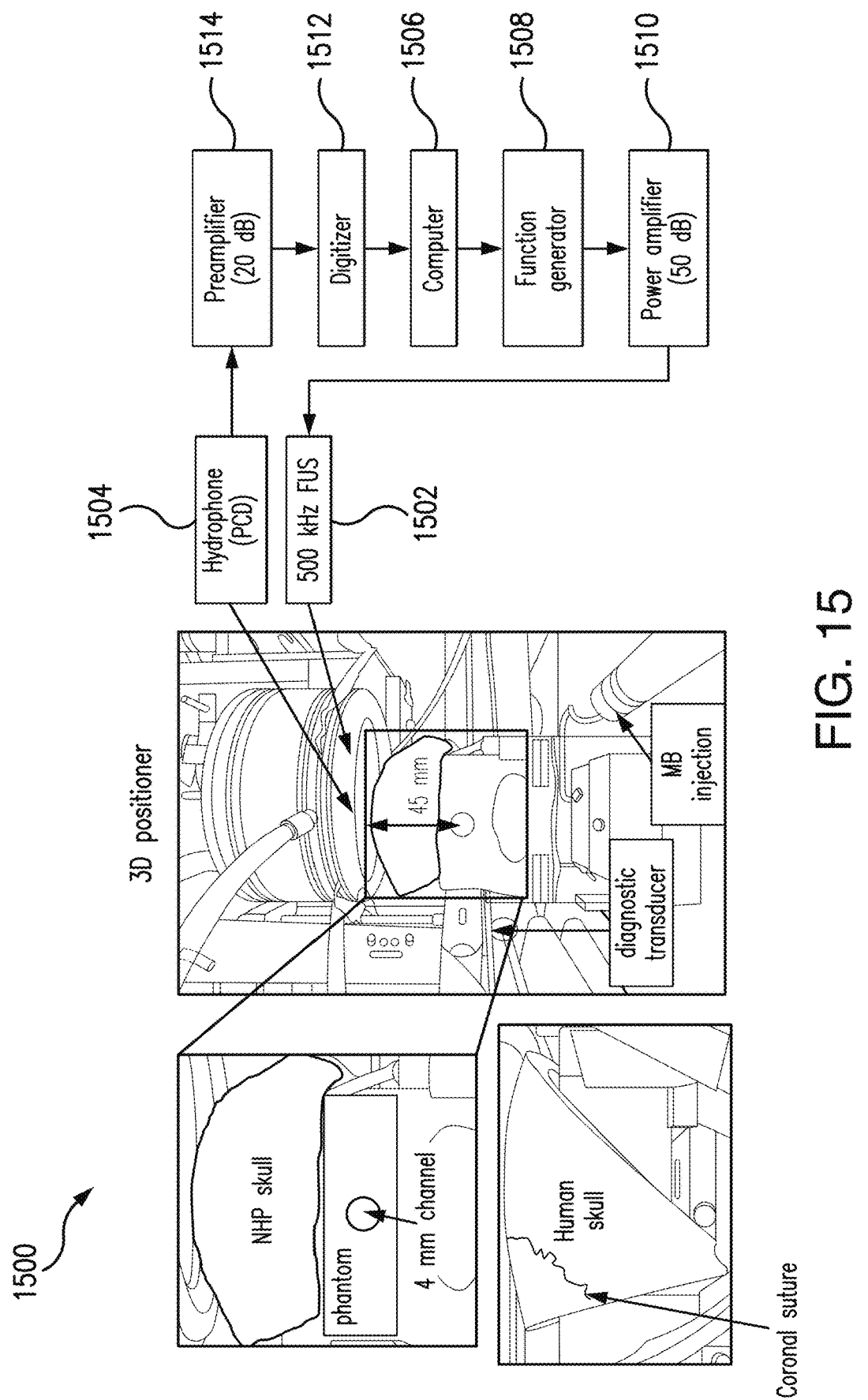
FIG. 15 is a diagram illustrating an exemplary system for in vitro cavitation-guided opening and monitoring of a tissue in a primate in accordance with an exemplary embodiment of the disclosed subject matter.
Figures 16A, 16B, 16C, 16D:
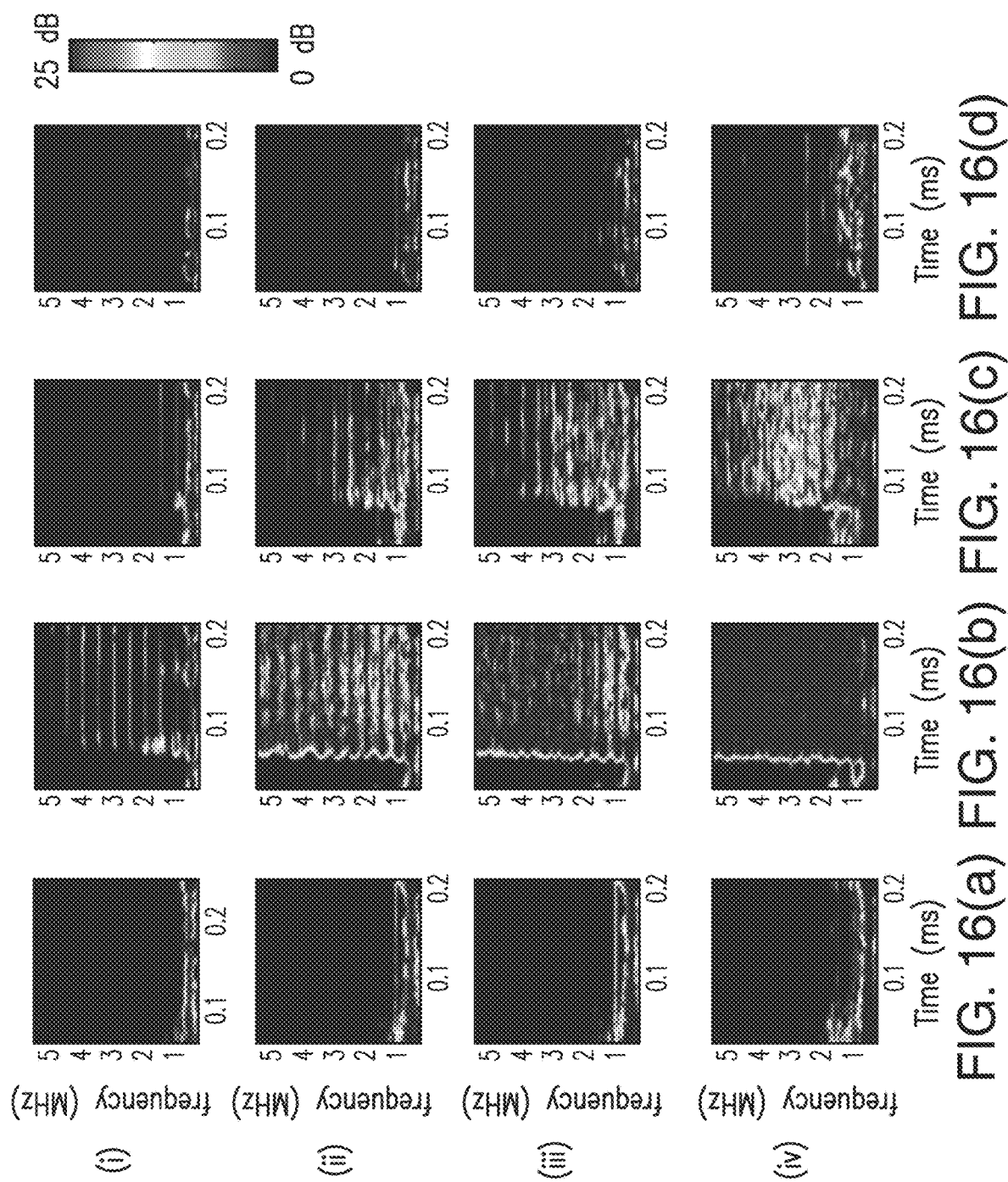
FIGS. 16A-16D are diagrams illustrating exemplary results for in vitro cavitation monitoring according to the disclosed subject matter.

FIG. 15 shows an exemplary system 1500 for in vitro FUS-induced BBB opening according to the disclosed subject matter. With reference to FIG. 15, system 1500 can include a single-element FUS transducer 1502 (for example and as embodied herein, H-107, Sonic Concepts, WA, USA), which can be operated at 0.5 MHz with a −6-dB focal width by length equals to 5.85 mm by 34 mm and a geometric focal depth of 62.6 mm for sonication. A spherically focused, flatband hydrophone 1504 (for example and as embodied herein, Y-107, Sonic Concepts, WA, USA; −6-dB sensitivity: 10 kHz-15 MHz) can be coaxially and confocally aligned with the transducer 1502 and can be utilized as the passive cavitation detector. For example, and as embodied herein, a PC work station 1506 (for example and as embodied herein, model T7600, Dell) with MATLAB® (Mathworks, MA, USA) can be configured and utilized to automatically control the sonication through a function generator 1508 (for example and as embodied herein, model 33220A, Agilent Technologies, CA, USA) followed by a 50-dB amplifier 1510 (for example and as embodied herein, A075, ENI, NY, USA). An exemplary controller to control the sonication through the function generator 1508 can be implemented using the exemplary computer program module in the Computer Program Listing Appendix hereto. PCD signal acquisition can be performed using a 14-bit analog-to-digital converter 1512 (for example and as embodied herein, Gage Applied Technologies, QC, Canada, at sampling rate: 100 MHz and 50 MHz in vitro and in vivo, respectively). A 20-dB amplification can be applied during opening of the macaque skull, for example using preamplifier 1514. By comparison, 10 dB can be applied using preamplifier 1514 for the human skull, which can be suitable due at least in part to increased reflection in the human skull. PCD signals in vivo, including the frequency spectra and cavitation doses can be monitored in real time as described herein.

In one embodiment, a desiccated macaque skull can be provided and can be sectioned to retain the cranial part (including, for example, frontal bone, parietal bones, and occipital bone), as shown for example in FIG. 15. The averaged thickness of the skull in the ultrasound beam path can 3.09 mm using a caliper at five points of the skull lined in a cross below the transducer 1502, and can be degassed for 24 hours prior to BBB opening.

In an alternative embodiment, a desiccated human skull can be provided and can be sectioned to retain the frontal and the parietal bones, as shown for example in FIG. 15, with an averaged thickness of 4.65 mm using the same measuring method described above. The human skull can be degassed for 48 hours prior to BBB opening. The pressures at the focus of the FUS transducer with and without the skulls can be calibrated using bullet hydrophone 1504.

A number of sonications can be performed, as summarized in Table 3. In-house, lipid-shell, monodisperse microbubbles (for example, embodied herein having median diameter: 4-5 μm) can be diluted to 2×105 bubbles/mL and injected to the 4-mm-in-diameter channel in the acrylamide phantom before and after placing the skull. The channel can be approximately 45 mm and 25 mm below the macaque and the human skull, respectively. The PCD with the hydrophone and the diagnostic B-mode imaging system (as embodied herein from Terason, MA, USA) can be used, separately or in combination, to monitor the sonication (for example and as embodied herein having peak negative pressure (PNP): 50-450 kPa, pulse length: 100 cycles (0.2 ms) and 5000 cycles (10 ms), pulse repetition frequency (PRF): 10 Hz, duration: 2 s), and thus can be configured to avoid interference with the PCD. B-mode images of bubble disruption can be acquired to support the FUS focusing at the channel, which can be performed through a linear array transducer (for example and embodied herein as 10L5, Terason, MA, USA; having center frequency: 5.1 MHz) and can be placed transversely to the FUS beam.

TABLE 3

Number of in vitro sonications.

| | | | Without microbubbles | With microbubbles |
|---|---|---|---|---|
| Skull effect (100 cycles) | Macaque | No skull | 41 | 49 |
| | | Skull | 33 | 46 |
| | Human | No skull | 60 | 60 |
| | | Skull | 70 | 81 |
| Pulse length effect (5000 cycles) | | No skull | 20 | 20 |

The in vitro system can be configured to mimic the in vivo conditions for targeting through the skull. For example and as embodied herein, FUS can be applied through the parietal bone proximate the sagittal suture, which can correspond to the position for targeting the thalamus, putamen, and caudate nucleus. Additionally or alternatively, the 4-mm channel can be utilized to accommodate the area of bubble disruption at the increased pressure (for example, 450 kPa). The reduced microbubble concentration can be utilized at least in part to reduce or minimize the bubble-bubble interaction (for example providing a mean distance between bubbles of 58.5 mm) while still capable of being captured for B-mode visualization. The sonication parameters (for example, pulse length, PRF, duration) can be set at described herein, which can modify the detection threshold. Sonication using 5000-cycle pulses without the skull in place can be performed in accordance with the in vivo techniques described herein.

In exemplary embodiments, in vivo FUS-inducement and BBB opening techniques can be performed. In one example, in vivo skull effects from FUS-inducement can be examined. In another example, BBB opening in primates can be performed. For each example, a number of sonications performed is summarized in Table 4. In each example, microbubbles were intravenously injected, and the total number of microbubbles administered was calculated based on the subject's weight. For purpose of illustration, and as embodied herein, for BBB opening a bolus of microbubbles (for example, $2.5 \times 10^8$ bubbles/kg) was injected and the sonication (for example, PNP: 250-600 kPa, pulse length: 10 ms, PRF: 2 Hz, duration: 2 min) started at the beginning of injection. For purpose of illustration, and as embodied herein, for examining the in vivo skull effect, a bolus of microbubbles (for example, $1.25 \times 10^8$ bubbles/kg) were injected after the BBB opening sonication. Ten seconds after the injection, the microbubbles perfused to the brain, and a consecutive sonication at ramp-up pressures was started (for example, PNP: 50-700 kPa, pulse length: 100 cycles (0.2 ms) or 5000 cycles (10 ms), PRF: 2 Hz, duration: 10 s). The thalamus and putamen were targeted as described herein.

TABLE 4

Number of in vivo sonications.

| | Pulse length | Without microbubbles | With microbubbles |
| --- | --- | --- | --- |
| Skull effect | 100 cycles | 8* | 8* |
| | 5000 cycles | 14** | 14** |
| BBB opening | 5000 cycles | 40 | 40 |

*6 at 700 kPa.
**12 at 700 kPa.

For example, and as embodied herein, Magnetic Resonance Imaging (for example, using 3T, Philips Medical Systems, MA, USA) was performed one-half hour after the sonication to confirm BBB opening and assess safety. Spoiled Gradient-Echo T1-weighted sequence (for example, TR/TE=20/1.4 ms; flip angle=30°; NEX=2; spatial resolution: 500×500 µm$^2$, slice thickness: 1 mm with no interslice gap) before and 40 min after intravenously injecting the contrast agent gadodiamide (for example, Omniscan®, GE Healthcare, NJ, USA; dosage: 0.2 mL/kg), was used to visualize the opening, as described further herein. T2-weighted sequence (for example, TR/TE=3000/80 ms; flip angle=90°; NEX=3; spatial resolution: 400×400 µm$^2$, slice thickness: 2 mm with no interslice gap) was performed for detecting edema. Susceptibility-weighted imaging (for example, SWI, TR/TE=19/27 ms; flip angle=15°; NEX=1; spatial resolution: 400×400 µm$^2$, slice thickness: 1 mm with no interslice gap) was performed for detecting hemorrhage.

Analysis for the opening volume across the targeted regions included image re-alignment, enhancement evaluation, and volume calculation. The pre-contrast and post-contrast images were aligned to the individual stereotactically aligned T1-weighted images acquired using FSL's FLIRT program to determine suitable alignment of the pre- to post-contrast images. The ratio of the post- to the pre-contrast images were taken and normalized by setting 0 and 1 to the mean of the contralateral region opposed to the sonicated region (for example, and as embodied herein, a circle of 6.25 mm in diameter in the horizontal slice) and the anterior cerebral artery (for example, and as embodied herein, a circle of 1.75 mm in diameter in the horizontal slice), respectively, and the opening region was thresholded by three times standard deviation of the contralateral (unsonicated) region. The volume was the accumulated voxels over the threshold in the sonicated region times the voxel size.

The PCD signals, frequency spectra, and spectrograms (for example, and as embodied herein, using an 8-cycle Chebyshev window, 98% overlap, 4096-point Fast Fourier Transform) were used to monitor the cavitation using MATLAB®. The cavitation level-time derivative of the cavitation dose can be quantified, and as such the harmonic, ultraharmonic, and the broadband signals in the spectra for each pulse can be separately filtered. The stable cavitation level based on harmonics only ($dSCD_h$) can be represented as the root-mean squared amplitude of the harmonic signals in a single pulse, with the harmonic signals represented as the maxima in the 20-kHz (−6-dB width) range around the harmonic frequency (0.5f*n) in the frequency spectrum. The stable cavitation level based on ultraharmonics only ($dSCD_u$) can be represented as the root-mean squared amplitude of the ultraharmonic signals in a single pulse, with the ultraharmonic signals represented as the maxima in 20 kHz around the ultraharmonic frequency (0.5f*n+0.25f) in the frequency spectrum. The inertial cavitation level (dICD) can be represented as the root-mean squared amplitude of the frequency spectrum after excluding the harmonics (360 kHz around the harmonic frequency) and ultraharmonics (100 kHz around the ultraharmonic frequency).

The cavitation dose for each sonication can be represented as the cumulative sum of the cavitation level in 1.25-5.00 MHz for every pulse; the cavitation SNR, can be represented as the ratio of post- to pre-microbubble administration cavitation doses.

Cavitation dose (CD)=$\Sigma_{t=0-T}dCD_t=\Sigma_{t=0-T}\sqrt{S^2}_t$

Cavitation SNR=20 log($CD_{post}/CD_{pre}$)  (1)

where t can represent the time for each pulse; T can represent the sonication duration; CD can represent the cavitation dose ($SCD_h$, $SCD_u$, and ICD for harmonics, ultraharmonics, and broadband emissions, respectively); $dCD_t$ can represent the cavitation level for the pulse at time t ($dSCD_h$, $dSCD_u$, and dICD for harmonics, ultraharmonics, and broadband emissions, respectively); $\sqrt{S^2}_t$ can represent the root-mean squared amplitude of the harmonic/ultraharmonic/broadband signals in the frequency spectrum for the pulse at time t; $CD_{post}$ can represent the post-microbubble administration cavitation dose; $CD_{pre}$ can represent the pre-microbubble administration cavitation dose.

For purpose of illustration, and as embodied herein, the frequency range used to quantify the cavitation level can be 1.25-5.00 MHz, which can be suitable to cover the strong harmonics, ultraharmonics, and broadband emission, while suppressing the linear and nonlinear scattering from the tissue and the skull. The quantification of the $SCD_h$ and the $SCD_u$ can be based on the acoustic emissions generated by the stable cavitation, including harmonics and ultraharmonics. The harmonics and ultraharmonics can be quantified separately due to the large difference of the spectral amplitudes. Such physical mechanisms can be considered to be different: the harmonics can be the result of volumetric oscillation, while the ultraharmonics and subharmonics can relate to the nonspherical bubble oscillation. Regarding quantifying the ICD, the width of the spectral window for the broadband signals can be chosen to reduce or minimize both the electronic noise and the increase due at least in part to the harmonic peaks. That is, the window width can be large enough to reduce or minimize the electronic noise by averaging and to not cover the broadening part of harmonic peaks.

The SCD based on subharmonics (SCDs) can be excluded due at least in part to the intrinsic low-frequency noise. The excitation frequency used can be relatively low, and as such the subharmonics can be overlapping with the linear scattering, whose amplitude can increase further with the scattering of the skull.

For purpose of illustration and not limitation, and as embodied herein, in the in vitro technique, an unpaired two-tailed Student's t-test can be used to determine if the treatment (post-microbubble administration) was significantly higher than the control (pre-microbubble administration) for each pressure. Additionally or alternatively, in the in vivo skull effect analysis, a paired two-tailed Student's t-test can be used to determine if the treatment (post-microbubble administration) was significantly higher than the control (pre-microbubble administration) for each pressure in each subject. The results of the exemplary statistical analysis is described further herein.

FIGS. 16A-16D illustrate the PCD spectrograms before and after placing the skull. Before placing the skull, the amplitude of harmonics, ultraharmonics as well as the broadband signals increased significantly with pressure after microbubble administration, as shown for example in FIG. 16B with comparison to the control of FIG. 16A, in which the second harmonic became significant at and above 150 kPa. The broadband signals increased mostly within the range of 3-5 MHz according to the results at 150 kPa and 200 kPa in FIG. 16B. After placing the macaque skull, as shown for example in FIG. 16C, the high frequency components were attenuated, while the signals remained detectable at the lowest pressure (for example, 50 kPa). After placing the human skull, as shown for example in FIG. 16D, the frequency components below 3 MHz were detected at and above 100 kPa.

For purpose of illustration and not limitation, and as embodied herein, B-mode cine-loops were also used to monitor the cavitation separately. FIGS. 17A-17D illustrate the images of the microbubbles in the channel phantom after sonication. The microbubbles were found to collapse at and above 200 kPa evidenced by the loss of echogenicity in the focal region in cases without the skull, as shown for example in FIG. 17A, with the macaque skull, as shown for example in FIG. 17B, with the human skull, as shown for example in FIG. 17C, and using longer pulses without the skull (for example, 5000 cycles as shown in FIG. 17D. The mean diameter of the hypoechogenic area at 200 kPa and 450 kPa was 1.3 mm and 4 mm, respectively.

FIGS. 18A-18I illustrate cavitation doses with and without the skull in place using 100-cycle pulses. Using the macaque skull, as shown for example in FIGS. 18A-18C, the $SCD_h$, the $SCD_u$, and the ICD, respectively, without placing the skull, were significantly higher (p<0.05) than the control at and above 50 kPa, which also increased monotonically with pressure. After placing the macaque skull, the $SCD_h$ was detectable (p<0.05) at all pressures, whereas the detection pressure threshold for both the $SCD_u$ and the ICD increased to 150 kPa. Using the human skull, as shown for example in FIGS. 18D-18F, the $SCD_h$ was detectable at and above 100 kPa after placing the skull. For the $SCD_u$, the detection pressure threshold increased to 250 kPa. For the ICD, the detection pressure threshold became 350 kPa. The $SCD_h$ at and above 400 kPa was undetected at least in part because the control signal with the human skull was strong. While the detection pressure threshold slightly changed after placing the macaque and the human skull, the sensitivity of cavitation doses to pressure changes remained the same.

Figure 18A:
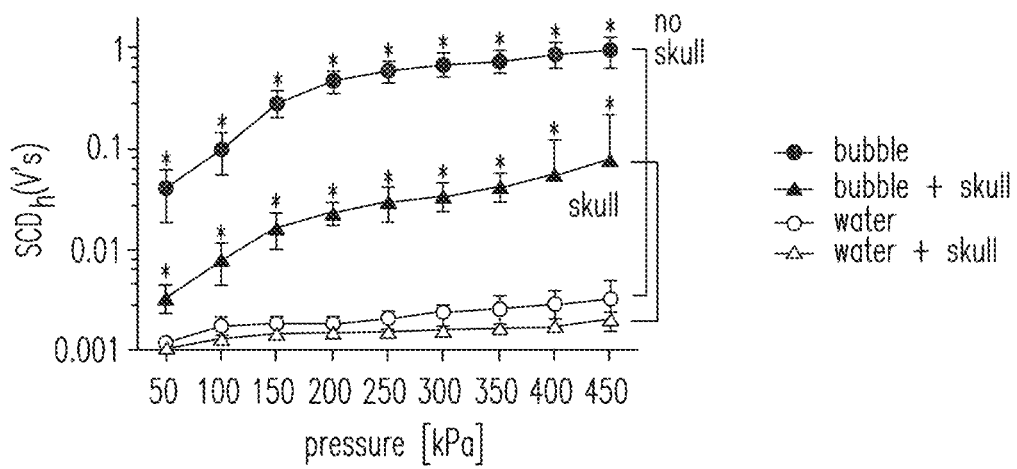
FIGS. 18A-18I are diagrams illustrating exemplary in vitro cavitation doses according to the disclosed subject matter.
Figure 18B:
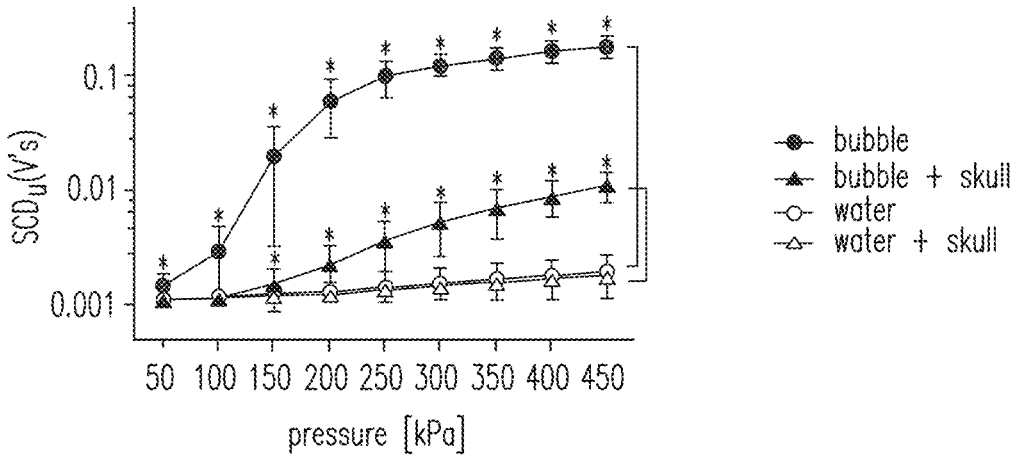
Figure 18C:
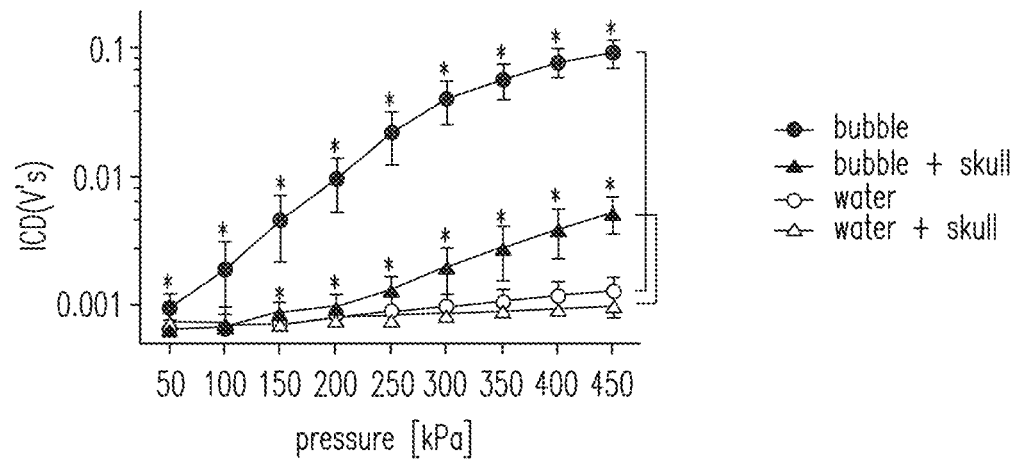
Figure 18D:
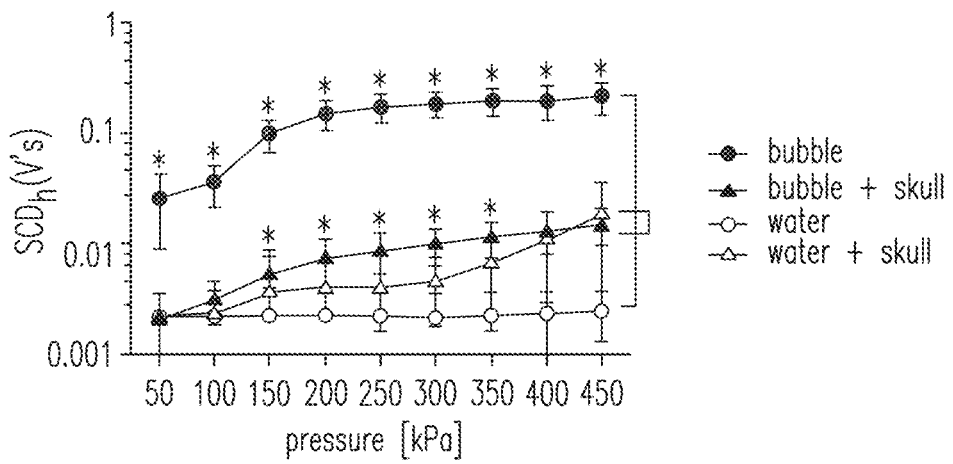
Figure 18E:
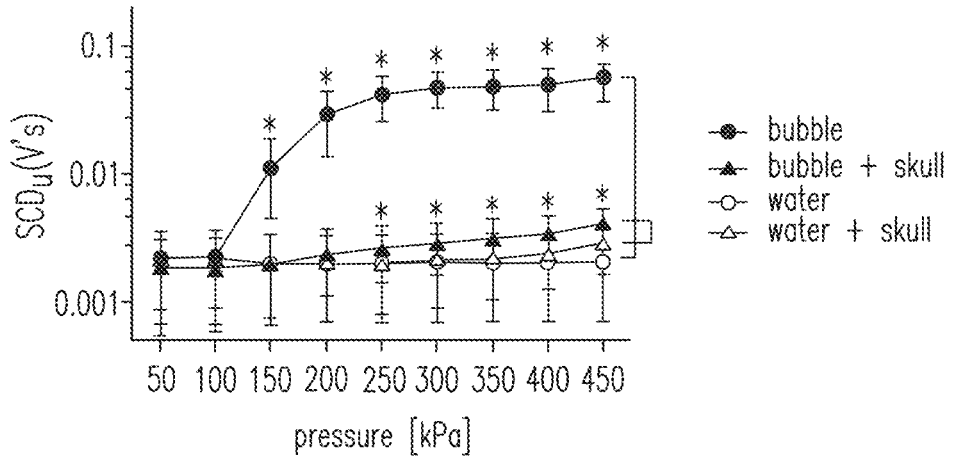
Figure 18F:
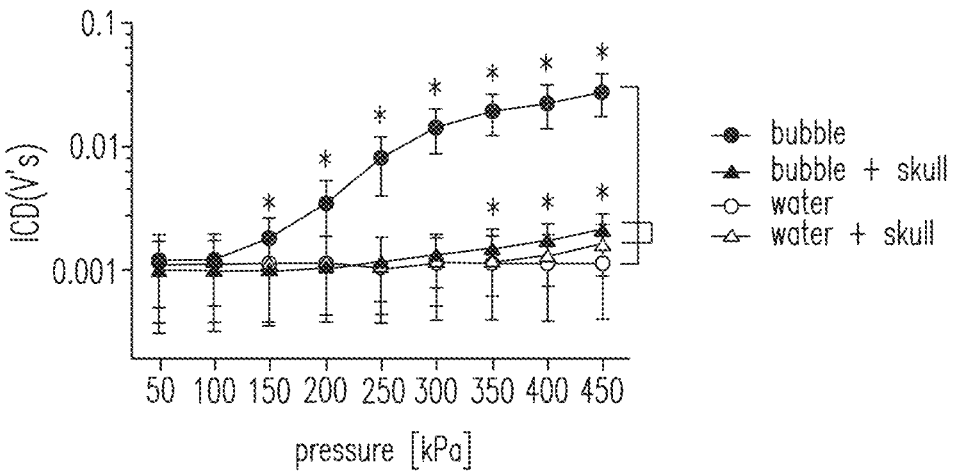
Figure 18G:
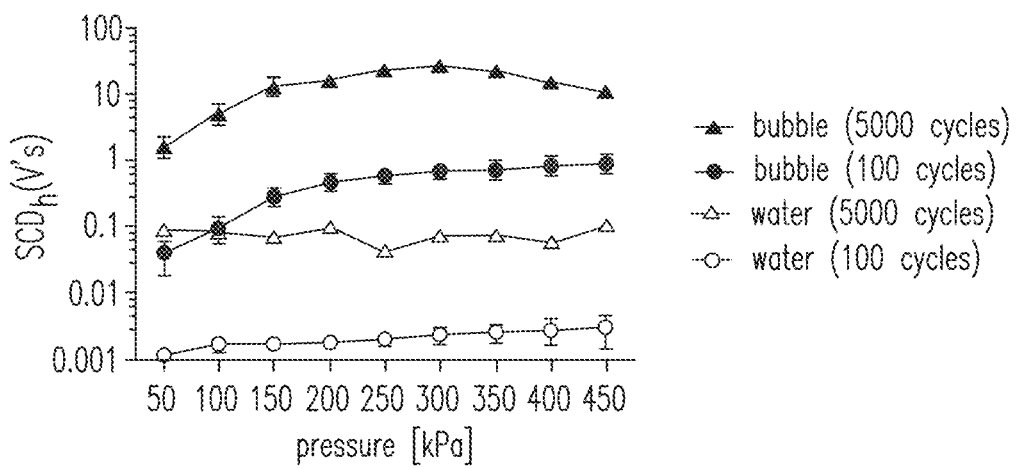
Figure 18H:
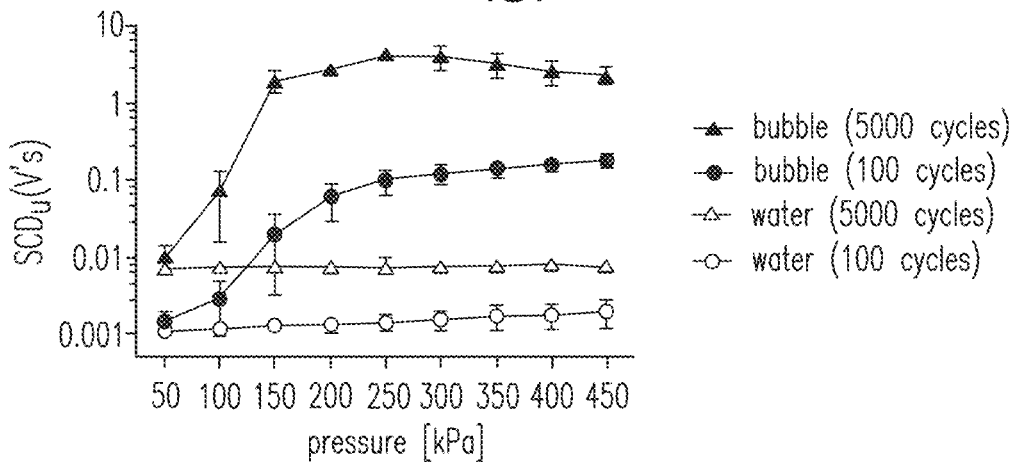
Figure 18I:
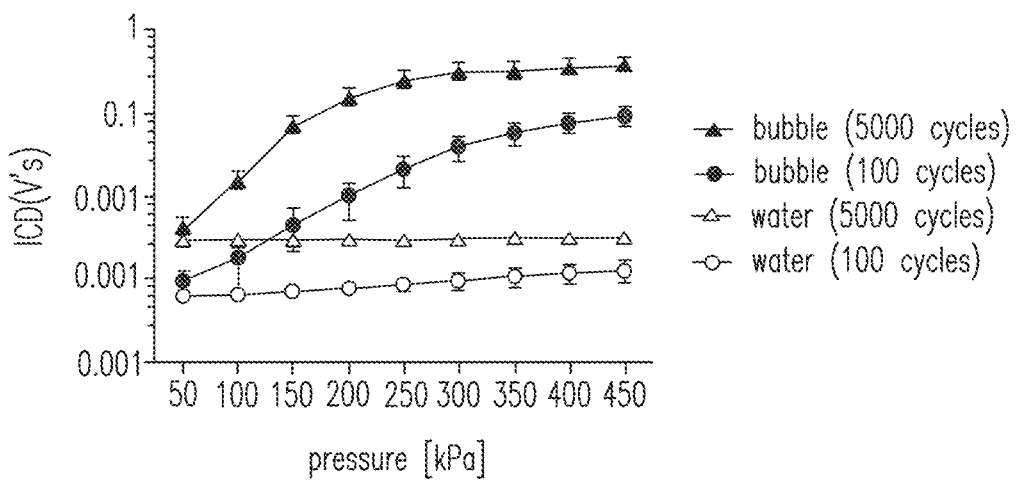

The pulse length effect on the cavitation dose was also analyzed. FIGS. 18G-18I illustrate the cavitation doses with 100-cycles and 5000-cycle pulse lengths. The $SCD_h$ using 100-cycle pulses increased monotonically with pressure increase, whereas the $SCD_h$ with 5000-cycle pulses reached a maximum at 300 kPa and started to decrease at pressures above 300 kPa. Similar to the $SCD_h$, the $SCD_u$ using 100-cycle pulses increased monotonically with pressure, while the $SCD_u$ using 5000-cycle pulses reached a plateau at 250 kPa and started to decrease at higher pressures. The ICD using 100-cycle and 5000-cycle pulses both increased monotonically with pressure increase, and the latter increased at a faster rate. As shown, the cavitation doses of 5000-cycle pulses were higher than that of 100-cycle pulses.

FIGS. 19A-19D illustrate the cavitation SNR, which can be used to analyze the sensitivity of PCD using pulse lengths, the detection limit, and skull attenuation. Before placing the skull, as shown for example in FIG. 19A, the cavitation SNR for the $SCD_h$, $SCD_u$, and ICD using 100-cycle pulses ranged within 28.6-49.1 dB, 2.1-38.9 dB, and 3.1-37.0 dB, respectively. As shown, followed by the $SCD_u$ and the ICD, the cavitation SNR for the $SCD_h$ was the highest. The cavitation SNR for the $SCD_h$, $SCD_u$, and ICD using 5000-cycle pulses, as shown for example in FIG. 19B, ranged within 24.8-54.6 dB, 2.2-54.8 dB, and 2.9-41.9 dB, respectively. Both the cavitation SNR for the $SCD_h$, $SCD_u$ reached a plateau at 250 kPa, while the cavitation SNR increased monotonically for the ICD.

Figure 19B:
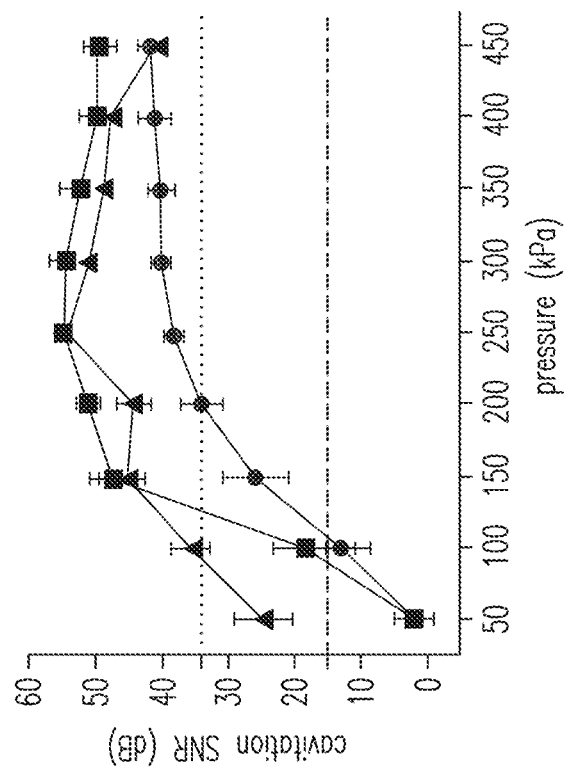
FIGS. 19A-19D are diagrams illustrating exemplary in vitro cavitation SNR according to the disclosed subject matter.
Figure 19A:
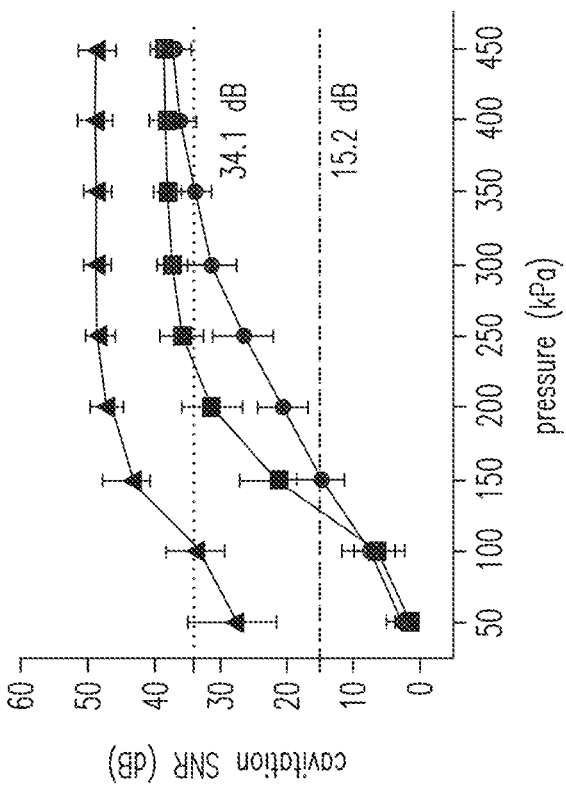
Figure 19D:
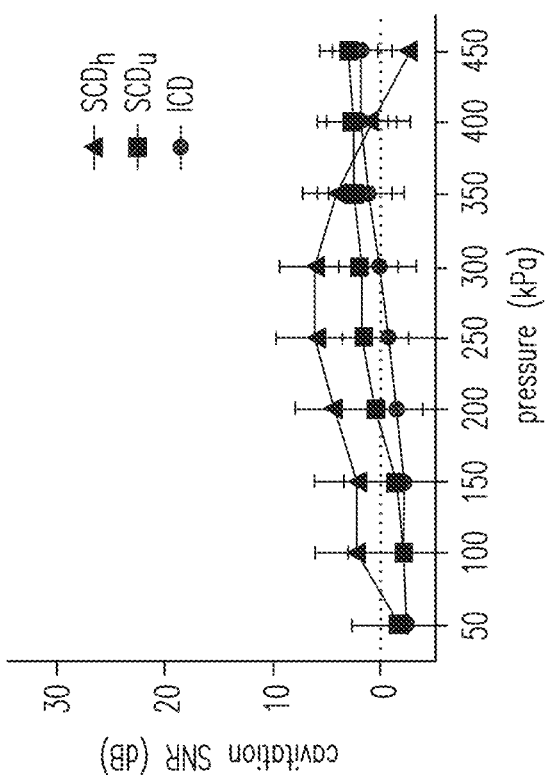
Figure 19C:
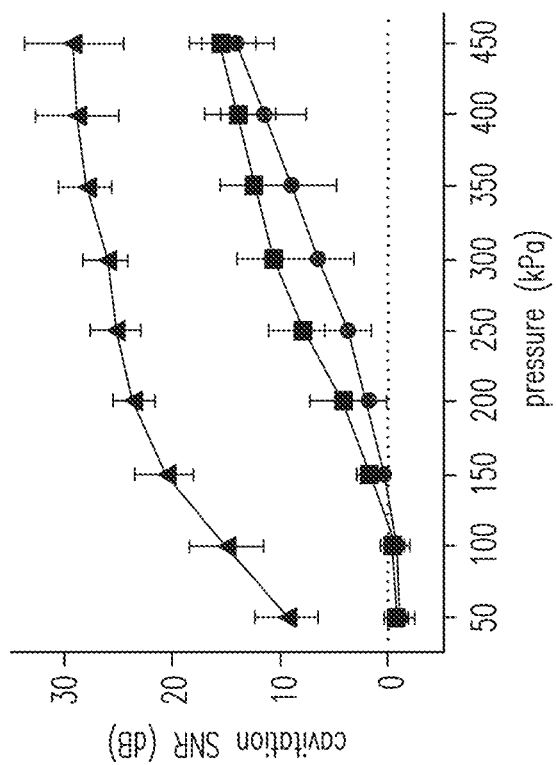

FIGS. 19C-19D show the cavitation SNR using 100-cycle pulses through the skull. The cavitation SNR through the macaque skull, as shown for example in FIG. 19C, corresponded to the statistically significant $SCD_h$, $SCD_u$, and ICD through the macaque skull, as shown for example in FIGS. 18A-18C, and ranged within 9.7-29.4 dB, 1.6-15.6 dB, and 1.1-14.1 dB, respectively. The cavitation SNR through the human skull, as shown for example in FIG. 19D, corresponded to the statistically significant $SCD_h$, $SCD_u$, and ICD through the human skull, as shown for example in FIGS. 18D-18F, and ranged within 2.4-6.2 dB, 1.4-3.0 dB, and 1.2-1.9 dB, respectively. For the cavitation SNR with the skull lower than 1 dB, the corresponding cavitation doses were shown to not reach statistical significance. As such, the PCD signals were suitable for analysis when the cavitation SNR exceeded 1 dB.

As described herein, the cavitation SNR with the skull, as shown for example in FIGS. 19C-19D can be correlated to the cavitation doses with the skull, as shown for example in FIGS. 18A-18F. As shown, when the cavitation SNR exceeded 1 dB, the transcranially acquired cavitation doses were statistically significant. The skull attenuation can be assessed. For example and as embodied herein, the cavitation SNR without the skull, as shown for example in FIG. 19A, can be compared with the cases with the skull surpassing the 1-dB SNR limit, as shown for example in FIGS. 19C-19D. As shown, the SNR without the skull was above 15.2 dB and 34.1 dB to be detected through the macaque and the human skull, respectively. The skull attenuation can be calculated by dividing by the skull thickness: for example and as embodied herein, 4.92 dB/mm and 7.33 dB/mm for the macaque and human, respectively.

Figure 20A:
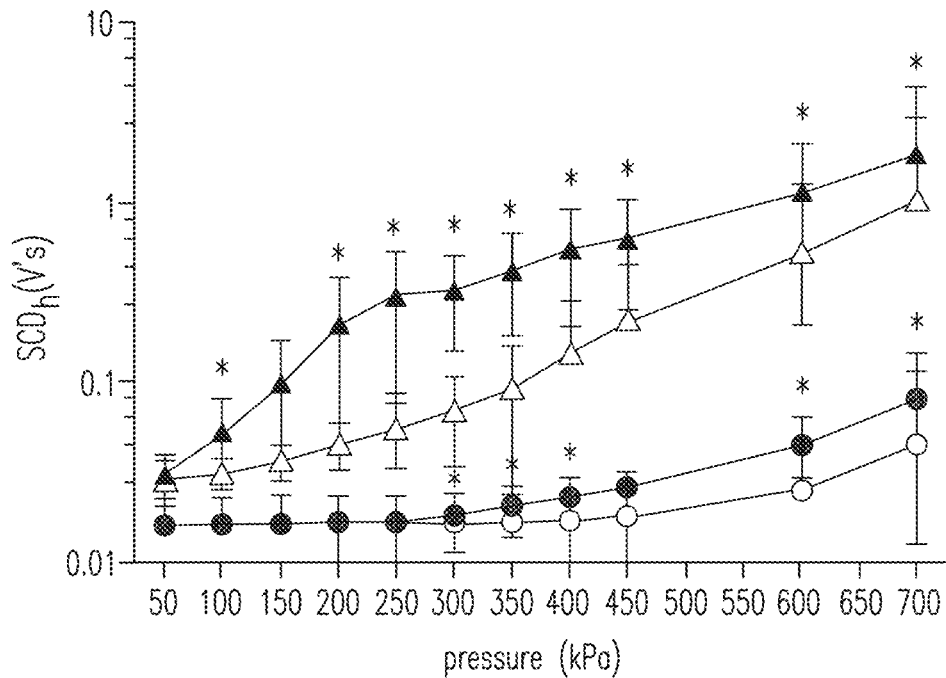
FIGS. 20A-20C are diagrams illustrating exemplary in vivo cavitation doses using 100 and 5000 cycles according to the disclosed subject matter.
Figure 20B:
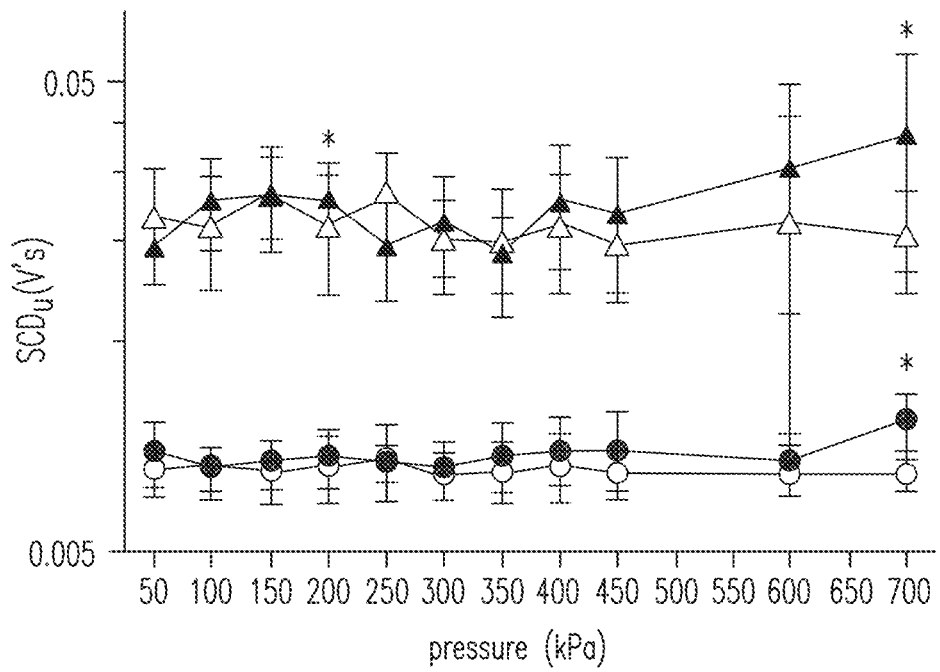
Figure 20C:
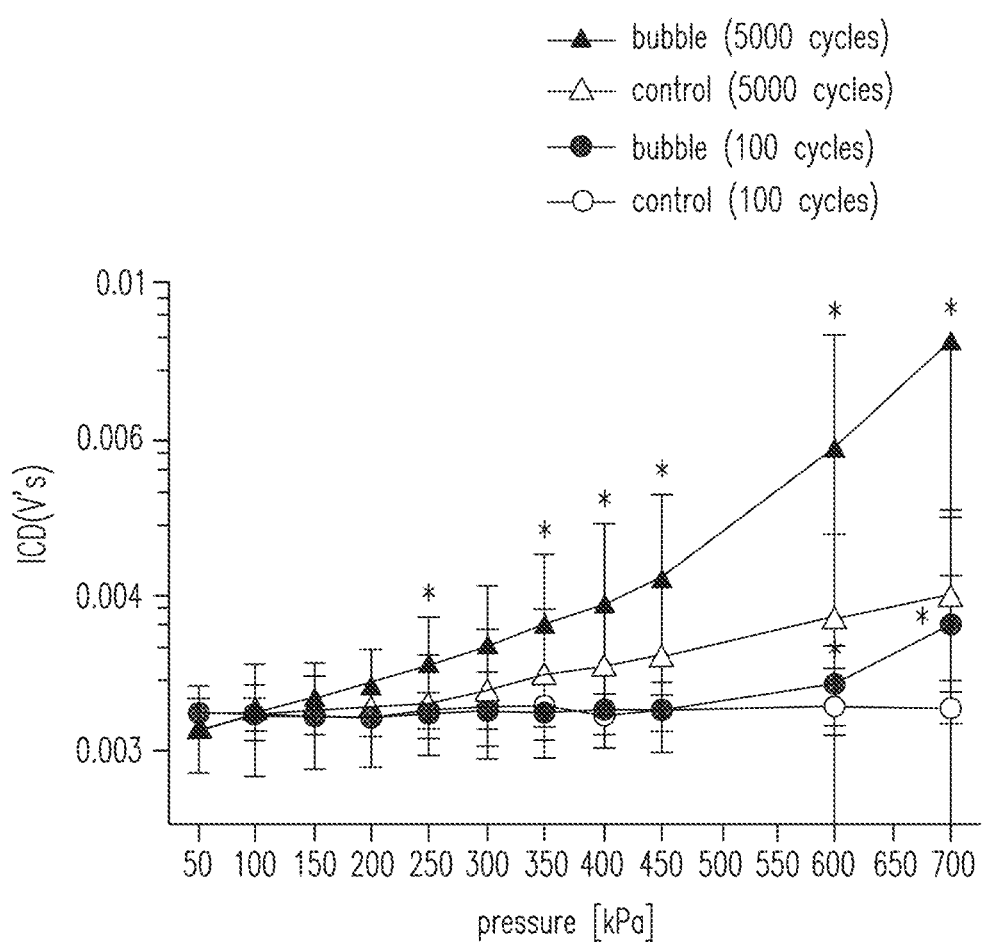

For example, and as embodied herein, in vivo skull effects at different pressures and different pulse lengths were analyzed and compared with the results of the in vitro techniques. FIGS. 20A-20C illustrate the cavitation doses using 100- and 5000-cycle pulses. When applying 100-cycle pulses, as shown for example in FIGS. 20A-20C, the $SCD_h$, $SCD_u$, and ICD, respectively, were significantly higher than the control at and/or above 300 kPa, 700 kPa, and 600 kPa, respectively. Furthermore, when applying 5000-cycle pulses, the $SCD_h$, $SCD_u$, and ICD were significant at pressure lower than that for the 100-cycle pulses: at and above 100 kPa, at 200 kPa and 700 kPa, and at and above 250 kPa, respectively. The cavitation dose when applying 5000-cycle pulses was higher than that with 100-cycle pulses. In either case, the cavitation doses increased monotonically with pressure increase. Besides, the $SCD_h$ using 100-cycle pulses at 450 kPa, the $SCD_h$ using 5000-cycle pulses at 150 kPa, and the ICD using 5000-cycle pulses at 300 kPa showed no significance ($0.05<p<0.06$) due to their higher variability.

Figure 21A:
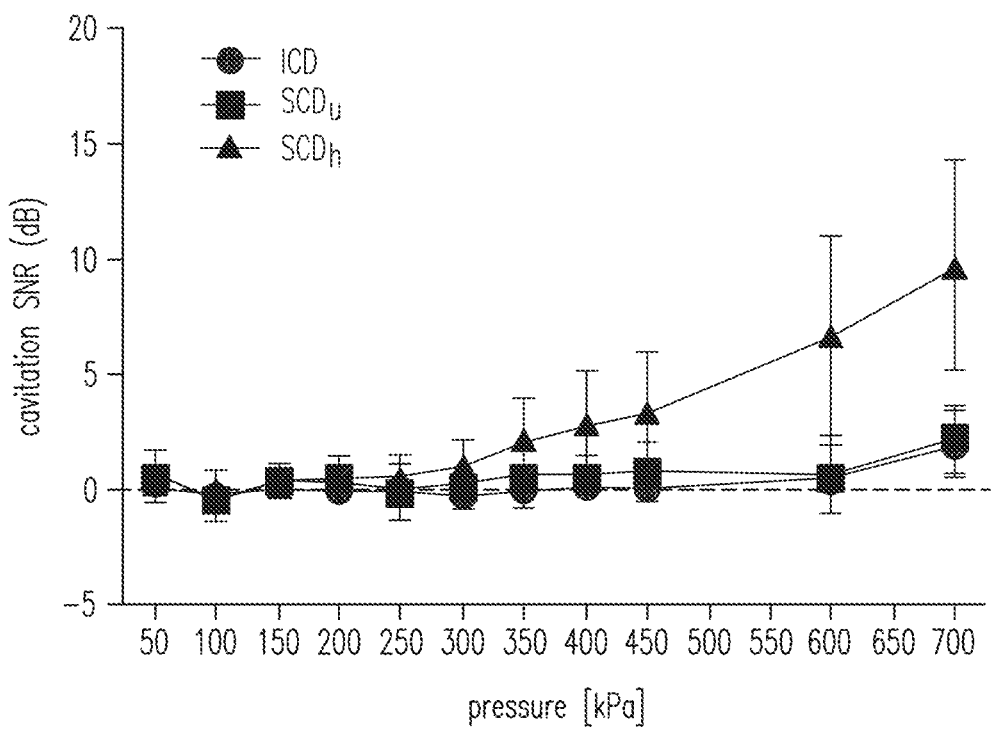
FIGS. 21A-21B are diagrams illustrating exemplary in vivo cavitation SNR according to the disclosed subject matter.
Figure 21B:
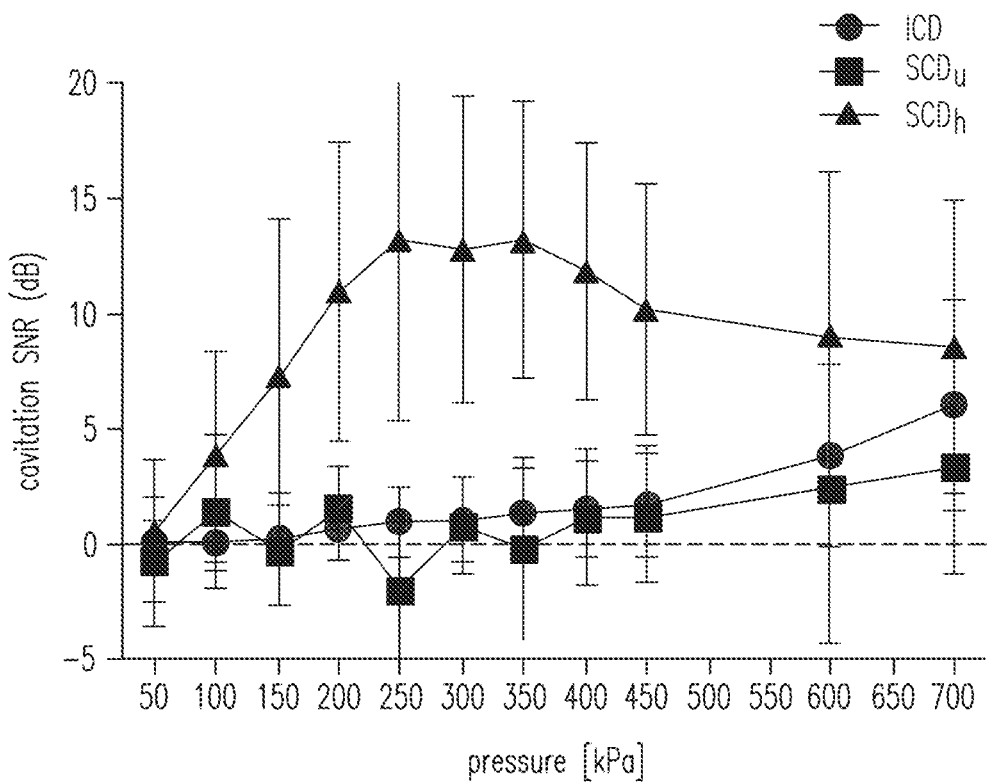

FIGS. 21A-21B illustrate the cavitation SNR for the skull effect using 100- and 5000-cycle pulses. When applying 100-cycle pulses, as shown for example in FIG. 21A, the cavitation SNR for the statistically significant $SCD_h$, $SCD_u$, and ICD ranged within 1.2-9.8 dB, 2.3 dB, and 0.7-2.1 dB, respectively. As shown, the cavitation SNR increased monotonically for the $SCD_h$ and ICD, and fluctuated for the $SCD_u$. When applying 5000-cycle pulses, as shown for example in FIG. 21B, the cavitation SNR for the $SCD_h$, $SCD_u$, and ICD ranged within 3.8-13.3 dB, 1.4-3.5 dB, and 1.0-6.1 dB, respectively. As shown, the cavitation SNR reached a plateau for the $SCD_h$ at 250 kPa and started to decrease at 400 kPa. For the $SCD_h$, the cavitation SNR fluctuated at low pressures and increased monotonically at and above 400 kPa. For the ICD, the cavitation SNR increased monotonically without fluctuating or reaching a plateau. The cavitation SNRs for pressures where significant cavitation signals were detected were all above the 1-dB SNR limit, with an exception for $SCD_u$, in which 57% of the measurements passing the detection limit were statistically insignificant. Such results were consistent with the corresponding in vitro results.

Realtime PCD monitoring during BBB opening is illustrated herein according to the disclosed subject matter. FIGS. 22A-22D each illustrate one of four examples, respectively, of PCD monitoring and the corresponding opening results in MRI at different pressures. The MRI showed BBB opening in two macaques in the thalamus and the putamen at pressures ranging from 250 kPa to 600 kPa, with opening volumes of 338.6, 223.8, 213.4, and 262.5 mm$^3$, respectively. The volume increased with pressures in the same macaque, as shown for example in FIGS. 22B-22D, in general, and the volume range varied among subjects. The $dSCD_h$ reached a plateau in 10-30 seconds after injecting microbubbles and was kept at the same level for the rest of sonication duration. The $dSCD_u$ remained mostly undetected. The dICD increased by 3.18 dB at 350 kPa and 0.19 dB at 450 kPa as compared the end of the sonication to the beginning, while it remained unchanged at 275 kPa and 600 kPa.

FIGS. 23A-23D illustrate the safety assessment using T2-weighted MRI and SWI corresponding to the four BBB opening cases in FIGS. 22A-22D. In each example, no edema or hemorrhage was detected, which corresponded to the PCD monitoring results for which minimum or no ICD increase was seen during sonication.

For purpose of illustration, and as embodied herein, the sensitivity, reliability, and the transcranial cavitation detection limit in macaques and humans were investigated, using both in vitro macaque and human skull techniques as well as in vivo techniques for the skull effect and BBB opening in macaques as described herein. The in vitro techniques allowed for precise control to investigate cavitation characteristics and the skull effects, while the in vivo techniques confirmed the in vitro findings using realtime PCD monitoring. The transcranial PCD was found sensitive to detect cavitation signals at pressures as low as 50 kPa. The transcranial detection limit (for example and as embodied herein as 1-dB SNR limit) served as a criterion to determine reliable detection. Realtime PCD monitoring was performed during BBB opening, in which safe opening and reliable detection was achieved using long pulses.

B-mode imaging was used to visualize the cavitation, to achieve suitable focal alignment to the channel and the pressure in situ. B-mode imaging visualized cavitation by the maintenance or loss of echogenicity, representing stable or inertial cavitation, respectively. B-mode imaging also confirmed suitable focal alignment to the channel before and after placing the skull by detecting the bubble collapse at the center of the channel. Furthermore, suitable pressure in the channel was achieved after placing the skull at least in part because the loss of echogenicity became detectable at 200 kPa.

In contrast to the active visualization of B-mode imaging, the PCD served as an indirect monitoring tool. The PCD was shown to be more sensitive than B-mode imaging at least in part because it detected inertial cavitation at 50 kPa, lower than the lowest pressure losing echogenicity (e.g., 200 kPa). Detecting bubble destruction in B-mode imaging can be inhibited by its spatial and contrast resolution, which generally did not detect a smaller amount of bubble destruction at pressures lower than 200 kPa. As such, B-mode imaging was used to supplement to the PCD results rather than to determine the inertial cavitation threshold. As shown, the inertial cavitation occurred at 50 kPa as described herein, due at least in part to low excitation frequency, long pulse lengths, and low stiffness of the in-house microbubbles with a 4-5 μm diameter.

For purpose of illustration and not limitation, with reference to FIGS. 18A-18I, the pulse length was shown to affect the characteristics of the cavitation doses. Using 100-cycle pulses, the cavitation doses increased monotonically with pressure increase as the magnitude of bubble oscillation increased. Furthermore, using long pulses (e.g., 5000 cycles) was found to be more effective in generating higher cavitation doses. In this manner, the ICD still increased monotonically with pressure increase, while the $SCD_h$ and the $SCD_u$ reached a plateau at 250 kPa. As such, under a long-pulse excitation, a larger number of microbubbles underwent stable and inertial cavitation, and stable cavitation reached a plateau and started to decrease when most microbubbles were undergoing inertial cavitation and collapse immediately without contributing to stable cavitation. Furthermore, the microbubbles undergoing stable cavitation diffused faster using longer pulses and failed to enhance the $SCD_h$.

With continued reference to FIGS. 18A-18I, through the skull the change of cavitation doses to pressure change remained the same, while the pressure threshold for the cavitation doses becoming detectable varied depending on the type of cavitation doses and the skull. The monotonical increase of cavitation doses to pressure increase remained the same after placing the macaque and the human skull for signals surpassed the skull attenuation. By comparison, the pressure threshold to detect the $SCD_h$ through the macaque skull was unchanged, while it increased for the $SCD_h$ and ICD; for the human skull, the threshold increased for the three types of cavitation doses. For each type of cavitation doses, the pressure threshold for the $SCD_h$ was the lowest, followed by the $SCD_u$ and ICD. The $SCD_h$ remained detectable through the skull at 50 kPa and 100 kPa for macaques and humans, respectively. For the $SCD_u$ and ICD, the pressure threshold increased to 150 kPa and 350 kPa for macaques and human respectively due at least in part to low signal intensity, while the ultraharmonics and the broadband emissions occurred at 50 kPa.

Referring now to FIGS. 20A-20C, the in vivo skull effect was supported by the in vitro results, except that the in vivo $SCD_u$ was less reliable. Using 100-cycle and 5000-cycle pulses, the $SCD_h$ as well as the ICD increased monotonically with pressure as in the in vitro cases, with the exception that the $SCD_h$ for the 5000-cycle pulse did not reach a plateau, which can be due at least in part to the nonlinear scattering from the skull and air trapped between the transducer and the subject's skin. By comparison, the $SCD_u$ can be less reliable due at least in part to the less frequent ultraharmonics and can be attributed to the biological environment such as blood, capillary, and blood vessel. Furthermore, the varying blood pressure can contribute to variation the $SCD_u$. Additionally, the inertial cavitation was detected at and above 250 kPa, although microbubble collapse can occur at lower pressures.

For purpose of illustration and not limitation, and as embodied herein, the cavitation SNR was defined and used to investigate the sensitivity and reliability of PCD under different conditions, such as varied pressures and pulse lengths, and the skull effects thereon. Such techniques can provide a quantitative way to find the transcranial detection limit (for example, embodied herein as a 1-dB SNR limit), the skull attenuation, as well as techniques to improve the detection. To achieve improved PCD, the cavitation SNR can be increased, for example and without limitation, by increasing the pressure, the pulse length, and/or the number of microbubbles injected. As shown herein, using longer pulse lengths (e.g., 5000 cycles) was effective in increasing the cavitation SNR at low pressures (e.g., less than 250 kPa, while the cavitation SNR for the $SCD_h$ decreased at high pressures (e.g., above 250 kPa) due at least in part to the cavitation characteristics and nonlinear skull scattering. Increasing the number of microbubbles injected can also improve the cavitation SNR, at least in part because the inertial cavitation can be detected at lower pressures (e.g., 250 kPa) in the in vivo skull effect analysis techniques after a second bolus injection of microbubbles.

The cavitation signals were considered reliable through the skull with a cavitation SNR above 1 dB. That is, the signals were strong enough to surpass skull attenuation. The 1-dB SNR level was determined using the in vitro technique and confirmed using the in vivo technique. Using each technique, the cavitation doses showed statistical significance when satisfying this criterion with the only exception in $SCD_u$. In this manner, the transcranial detection level provides an indication of inertial cavitation detected using the macaque subjects. Furthermore, such a determination can provide an indication of reliable PCD for all types of cavitation doses.

The skull attenuation for macaque was measured as 4.92 dB/mm and for human was measured as 7.33 dB/mm. As such, the attenuation by the human skull is higher than that for macaque, which can be due to at least in part to increased skull density, increased nonlinear ultrasound transmission, increased reflections and different extents of mode conversion. The cavitation SNR can be increased to surpass the 1-dB SNR level by increasing the pressure, the pulse length, and/or the number of microbubbles injected as discussed above. Furthermore, the in situ cavitation strength can be determined by combining the transcranial PCD measurements (for example, above the 1-dB SNR level) with the skull attenuation acquiring from simulation and/or ex vivo measurement to assess the treatment outcome.

Additionally, the inherent skull attenuation, nonlinear ultrasound scattering due at least in part to the skull can inhibit or prevent the detection of harmonics. As shown for example in FIG. 18D, nonlinear scattering from the human skull can become apparent at and above 450 kPa, inhibiting or preventing the detection of the harmonics ($SCD_h$) generated by the microbubble cavitation. Such a result can be due at least in part to higher pressure applied to compensate for the 80% of pressure attenuation through the human skull, which can introduce nonlinear scattering. Furthermore, as embodied herein, the FUS focus was 25 mm below the human skull, which can introduce increased nonlinear effects compared to deeper focus. In addition, trapped air can be present, which can inhibit or prevent detection. As shown for example in FIG. 20A, such a result occurred in the in vivo macaque results, in which nonlinear scattering was introduced using a 5000-cycle pulse. Such nonlinear effects can thus inhibit or prevent the detection of the $SCD_h$ and can lead to overtreatment due at least in part to the monitoring.

Additionally, and as embodied herein, realtime monitoring of the cavitation doses was performed during BBB opening using 5000-cycle pulses, providing information related to bubble perfusion and the cavitation level. Furthermore, and as embodied herein, the use of such long pulses can provide reliable PCD monitoring and facilitate opening at low pressures. The $SCD_h$ can be monitored as described herein, and the time for microbubbles perfuse to the sonicated region as well as the microbubble persistence during the entire treatment can be monitored at pressures as low as 250 kPa. The ICD can be monitored as described herein, and the safety of the treatment can be assumed in real time at least in part because low or no inertial cavitation was detected in the examples of safe BBB opening. Low or no ICD obtained during BBB opening experiments, as shown for example in FIGS. 22A-22D, compared to the in vivo skull effect analysis, as shown for example in FIGS. 20A-20C, can be due at least in part to lower numbers of microbubbles circulating during BBB opening, at least in part because an increase of ICD was obtained in the same subject after a second bolus injection of microbubbles during the in vivo skull effect analysis.

As shown for example in FIGS. 22A-22D, safe BBB opening was achieved at low pressures (e.g., 250-600 kPa) in both the putamen and the thalamus. No differences were observed in the putamen and the thalamus in terms of cavitation doses or opening threshold in this study. The opening volume varied across subjects, but increased with pressure in the same macaque, as illustrated by comparison of the 350-kPa example shown in FIG. 22B with the 600-kPa example shown in FIG. 22D. The 450-kPa example shown in FIG. 22C had smaller opening volume than the 350-kPa example, as indicated at least in part by the slightly decreasing $SCD_h$, which can be due at least in part to the subject's physiological effect to the circulating microbubbles. Furthermore, the average SCD$_h$ at different pressures was at the same level, owing to the cavitation characteristics using long pulses and the high variation between examples, as shown for example in FIGS. 20A-20C.

Correlating the cavitation doses to the opening volume based on single-element PCD can be performed using the ICD instead of the SCD$_h$. This can be performed at least in part because the positive correlation of the ICD to pressure can be independent of the pulse length, which can affect the cavitation characteristics. Additionally, the ICD typically is not affected by the nonlinear ultrasound scattering due to the skull (as illustrated for example by the human skull results in FIGS. 18D-18F). Furthermore, the ICD can also provide a safety assessment, as described herein. Reliable ICD detection can be achieved by increasing the cavitation SNR. In addition, passive cavitation mapping, including spatial information of cavitation can provide more precise estimation of opening volume and safety assessment using both the SCD$_h$ and ICD.

For purpose of illustration, and as described herein, in vitro macaque and human skull techniques as well as in vivo macaque techniques to analyze the skull effect and BBB opening are provided. As shown, through the macaque skull the pressure threshold for detecting the SCD$_h$ remained the same, while it increased for the SCD$_u$ and ICD. Through the human skull, the pressure threshold increased for each type of cavitation dose. The pressure threshold for detection the SCD$_h$ was the lowest, followed by the SCD$_u$ and ICD. The change of cavitation doses to pressure increase remained the same through the skull where the signal intensity surpassed the skull attenuation (for example, and as embodied herein 4.92 dB/mm for the macaque and 7.33 dB/mm for the human). The transcranial PCD was found to be suitable when the cavitation SNR exceeded the 1-dB SNR level in both in vitro and in vivo examples. Using long pulses can allow for reliable PCD monitoring and facilitates BBB opening at low pressures. The in vivo results illustrated that the SCD$_h$ was detected at pressures as low as 100 kPa; the ICD, at 250 kPa and can occur at lower pressures; the SCD$_u$, at 700 kPa and was less reliable at lower pressures. Realtime monitoring of PCD was performed in vivo in macaques during BBB opening, and safe opening has been achieved at 250-600 kPa in both the thalamus and the putamen, with minimum or no inertial cavitation detected. Furthermore, transcranial PCD in macaques in vitro and in vivo as well as humans in vitro can be considered reliable, for example by improving the cavitation SNR to surpass the 1-dB detection level.

COMPUTER PROGRAM LISTING APPENDIX

```
%%---Initialize the function generator-----------------------------------
%    PARAMETERS           EXAMPLE
%    frequency [MHz]      1.5
%    voltage [Vppk]       0.050
%    voltage offset [V]   0
%    burst count          30000 = 20 ms
%    burst period [s]     0.1 = 1/PRF
global fgen;
fgen = visa('agilent','USB0::2391::1031::MY44038421::0::INSTR');
fopen(fgen);
fprintf(fgen,'OUTPut OFF');
fprintf(fgen,'*RST');
```

COMPUTER PROGRAM LISTING APPENDIX

```
fprintf(fgen, 'FUNCtion SINusoid');
fprintf(fgen, sprintf('FREQuency %3g MHz', freq));
fprintf(fgen, sprintf('VOLTage %3g VPP', volt));
fprintf(fgen, sprintf('VOLTage:OFFSet %g V', volt_offset));
fprintf(fgen, 'BURSt:MODE TRIGgered');
fprintf(fgen, 'TRIGger:SOURce IMMediate');
fprintf(fgen, sprintf('BURSt:NCYCles %g',bm_count));
fprintf(fgen, sprintf('BURSt:INTernal:PERiod %g',bm_period));
fprintf(fgen, 'BURSt:STAT ON');
fprintf(fgen,'OUTPut ON');
%%%%
fprintf(fgen,'OUTPut OFF');
fclose(instrfind)
fclose(fgen);
```

We claim:

1. A method for opening a targeted region of a tissue, comprising:
   delivering one or more microbubbles to a region of tissue proximate to the targeted region;
   applying an ultrasound beam using a transducer to the targeted region to open the tissue;
   acquiring acoustic emissions produced from an interaction between the one or more microbubbles and the tissue;
   determining a cavitation spectrum from the acquired acoustic emissions;
   determining whether a vessel is located between the ultrasound beam and the targeted region or proximate to the targeted region based on the cavitation spectrum; and
   determining a cavitation signal-to-noise ratio (SNR) from the acquired acoustic emissions, wherein the cavitation SNR is a ratio of post- to pre-microbubble cavitation doses.

2. The method of claim 1, wherein the method is performed in vivo.

3. The method of claim 1, further comprising determining a focal depth of the transducer based on the acoustic emissions.

4. The method of claim 1, further comprising adjusting the targeted region based on the vessel.

5. The method of claim 1, further comprising adjusting the targeted region based on the vessel, wherein the adjusting comprises avoiding the vessel or shielding by the vessel.

6. The method of claim 1, further comprising determining a presence of inertial cavitation during opening and adjusting one or more parameters to prevent the inertial cavitation.

7. The method of claim 6, wherein the one or more parameters is selected from the group consisting of a size of the one or more microbubbles and an acoustic pressure of the ultrasound beam.

8. The method of claim 7, wherein the one or more microbubbles is adjusted to a size within a range of between 1 to 10 microns.

9. The method of claim 7, wherein the acoustic pressure of the ultrasound beam is adjusted to within a range between 0.3 to 0.45 MPa at the targeted region.

10. The method of claim 1, wherein the ultrasound beam has a center frequency from 0.5 to 1.5 MHz and a pressure from 0.3 MPa to 0.6 MPa.

* * * * *

UNITED STATES PATENT AND TRADEMARK OFFICE
CERTIFICATE OF CORRECTION

PATENT NO. : 11,273,329 B2
APPLICATION NO. : 16/575044
DATED : March 15, 2022
INVENTOR(S) : Elisa E. Konofagou, Fabrice Marquet and Yao-Sheng Tung It is certified that error appears in the above-identified patent and that said Letters Patent is hereby corrected as shown below:

In the Specification

In Column 1, Lines 25-30, under the heading, STATEMENT REGARDING FEDERALLY-SPONSORED RESEARCH please correct:
"This invention was made with government support under Grant Nos. R01AG038961, R01 EB009041 and R21EY018505 awarded by the National Institutes of Health and CAREER 0644713 and MH059244 awarded by the National Science Foundation. The government has certain rights in the invention."

To read:
-- This invention was made with government support under MH059244, EB009041, EY018505, and AG038961 awarded by the National Institutes of Health, and 0644713 awarded by the National Science Foundation. The government has certain rights in the invention. --

Signed and Sealed this
Seventh Day of May, 2024

Katherine Kelly Vidal
*Director of the United States Patent and Trademark Office*